United States Patent
Walter et al.

(10) Patent No.: US 12,279,892 B2
(45) Date of Patent: Apr. 22, 2025

(54) METHODS AND APPARATUS FOR DETECTING MOTION VIA OPTOMECHANICS

(71) Applicant: YUKKA MAGIC LLC, Wilmington, DE (US)

(72) Inventors: Jonathan T. Walter, Wake Forest, NC (US); Steven Matthew Just, Cary, NC (US); Wolfgang Wagner, Chapel Hill, NC (US); Steven Francis LeBoeuf, Raleigh, NC (US); Jesse Berkley Tucker, Youngsville, NC (US); Michael Edward Aumer, Raleigh, NC (US); Lawrence Christopher Eschbach, Louisburg, NC (US); Seth Long, Raleigh, NC (US)

(73) Assignee: Yukka Magic LLC, Wilmington, DE (US)

( * ) Notice: Subject to any disclaimer, the term of this patent is extended or adjusted under 35 U.S.C. 154(b) by 774 days.

(21) Appl. No.: 16/995,127

(22) Filed: Aug. 17, 2020

(65) Prior Publication Data

US 2020/0375547 A1    Dec. 3, 2020

Related U.S. Application Data

(63) Continuation of application No. 15/751,733, filed as application No. PCT/US2016/046273 on Aug. 10, 2016, now Pat. No. 10,856,812.
(Continued)

(51) Int. Cl.
| | |
|---|---|
| *A61B 5/1455* | (2006.01) |
| *A61B 5/00* | (2006.01) |
| *A61B 5/024* | (2006.01) |

(52) U.S. Cl.
CPC .......... *A61B 5/721* (2013.01); *A61B 5/02416* (2013.01); *A61B 5/14551* (2013.01);
(Continued)

(58) Field of Classification Search
CPC ... A61B 5/1455; A61B 5/721; A61B 5/02416; A61B 5/02; A61B 5/14552
See application file for complete search history.

(56) References Cited

U.S. PATENT DOCUMENTS

| | | |
|---|---|---|
| 5,158,082 A | 10/1992 | Jones |
| 6,466,808 B1 | 10/2002 | Chin et al. |

(Continued)

FOREIGN PATENT DOCUMENTS

| | | |
|---|---|---|
| CN | 1692874 A | 11/2005 |
| CN | 101803925 A | 8/2010 |

(Continued)

OTHER PUBLICATIONS

"First Office Action and English language translation", CN Application No. 201680047372.7, Jul. 9, 2020, 17 pp.
(Continued)

*Primary Examiner* — Marjan Fardanesh
(74) *Attorney, Agent, or Firm* — Brownstein Hyatt Farber Schreck, LLP

(57) ABSTRACT

Methods and apparatus are described for facilitating the extraction of cleaner biometric signals from biometric monitors. A motion reference signal is generated independently from a biometric signal and then the motion reference signal is used to remove motion artifacts from the biometric signal.

9 Claims, 34 Drawing Sheets

Related U.S. Application Data

(60) Provisional application No. 62/345,579, filed on Jun. 3, 2016, provisional application No. 62/257,502, filed on Nov. 19, 2015, provisional application No. 62/204,214, filed on Aug. 12, 2015.

(52) U.S. Cl.
CPC ........ *A61B 5/14552* (2013.01); *A61B 5/6804* (2013.01); *A61B 5/6817* (2013.01); *A61B 5/6843* (2013.01); *A61B 5/7214* (2013.01); *A61B 5/6802* (2013.01); *A61B 2562/146* (2013.01); *A61B 2562/185* (2013.01)

(56) References Cited

U.S. PATENT DOCUMENTS

| | | | |
|---|---|---|---|
| 7,702,374 | B2 | 4/2010 | Ishizuka et al. |
| 7,736,311 | B2 | 6/2010 | Bartnik et al. |
| 8,647,270 | B2 | 2/2014 | LeBoeuf et al. |
| 8,652,040 | B2 | 2/2014 | LeBoeuf et al. |
| 8,700,111 | B2 | 4/2014 | LeBoeuf et al. |
| 8,788,002 | B2 | 7/2014 | LeBoeuf et al. |
| 8,886,269 | B2 | 11/2014 | LeBoeuf et al. |
| 8,929,965 | B2 | 1/2015 | LeBoeuf et al. |
| 9,794,653 | B2 | 10/2017 | Aumer et al. |
| 2007/0280329 | A1 | 12/2007 | Kawauchi et al. |
| 2009/0227853 | A1 | 9/2009 | Wijesiriwardana |
| 2009/0286571 | A1 | 11/2009 | Liu |
| 2010/0217098 | A1 | 8/2010 | LeBoeuf et al. |
| 2012/0150052 | A1 | 6/2012 | Buchheim et al. |
| 2013/0267854 | A1 | 10/2013 | Johnson et al. |
| 2014/0058217 | A1* | 2/2014 | Giovangrandi ........ A61B 5/721 600/301 |
| 2014/0114147 | A1 | 4/2014 | Romesburg |
| 2014/0213863 | A1 | 7/2014 | Loseu et al. |
| 2014/0275852 | A1 | 9/2014 | Hong et al. |
| 2014/0288436 | A1 | 9/2014 | Venkatraman et al. |
| 2015/0011898 | A1 | 1/2015 | Romesburg |
| 2015/0118636 | A1 | 1/2015 | Romesburg |

FOREIGN PATENT DOCUMENTS

| | | |
|---|---|---|
| CN | 104684459 A | 6/2015 |
| EP | 2680217 A1 | 1/2014 |
| KR | 101033472 B1 | 5/2011 |
| KR | 20130129743 A | 11/2013 |
| WO | WO 2007/023426 A2 | 3/2007 |
| WO | WO 2007/038432 A2 | 4/2007 |
| WO | 2012134395 A1 | 10/2012 |
| WO | WO 2013/132147 A2 | 9/2013 |
| WO | 2014020484 A2 | 2/2014 |
| WO | 2015001434 A1 | 1/2015 |
| WO | 2015032006 A1 | 3/2015 |
| WO | 2015084376 A1 | 6/2015 |
| WO | WO 2016/140835 A1 | 9/2016 |

OTHER PUBLICATIONS

"Communication with European Search Report", EP Application No. 21181292.0, Apr. 4, 2022, 17 pp.
International Search Report, International Application No. PCT/US2016/046273, Nov. 25, 2016, 5 pp.
Written Opinion of the International Searching Authority, International Application No. PCT/US2016/046273, Nov. 25, 2016, 17 pp.
Communication with Supplementary European Search Report, EP Application No. 16835810.9, Jul. 3, 2018, 8 pp.
"Communication with Partial European Search Report", EP Application No. 21181292.0, Nov. 18, 2021, 11 pp.
"Second Office Action and English language translation", CN Application No. 201680047372.7, May 8, 2021, 22 pp.
"Decision on Rejection and English language translation", CN Application No. 201680047372.7, Nov. 3, 2021, 21 pp.

* cited by examiner

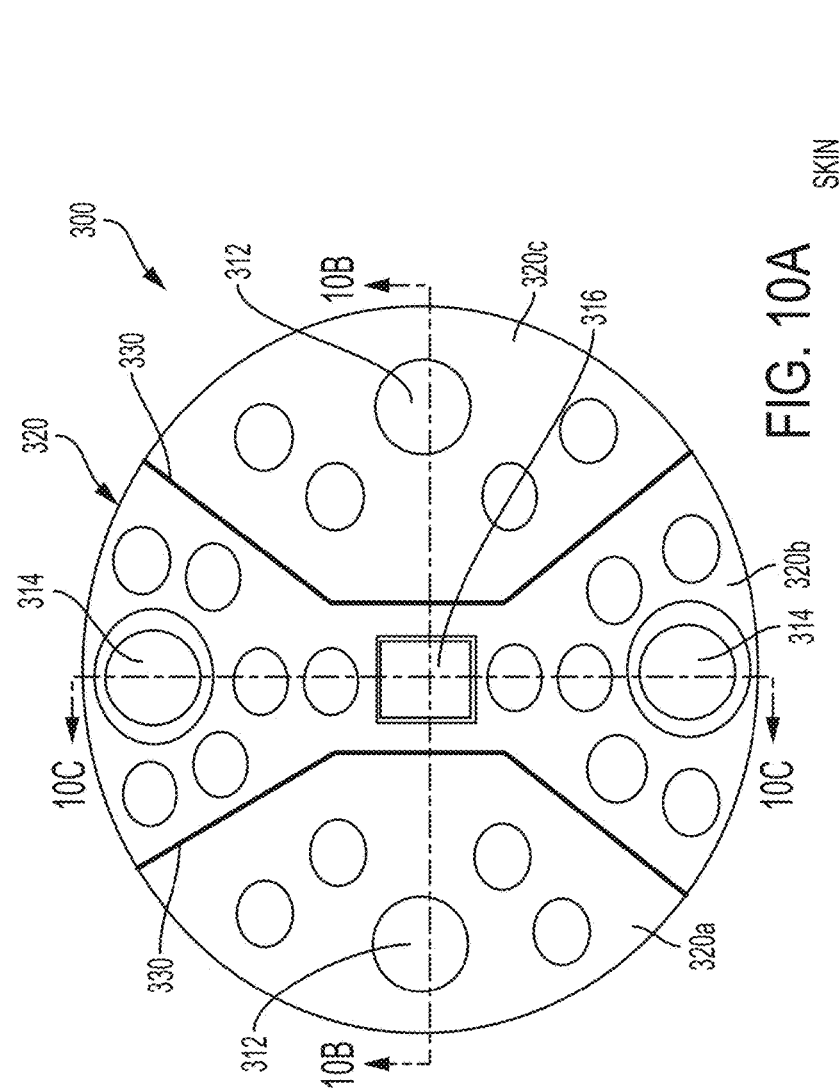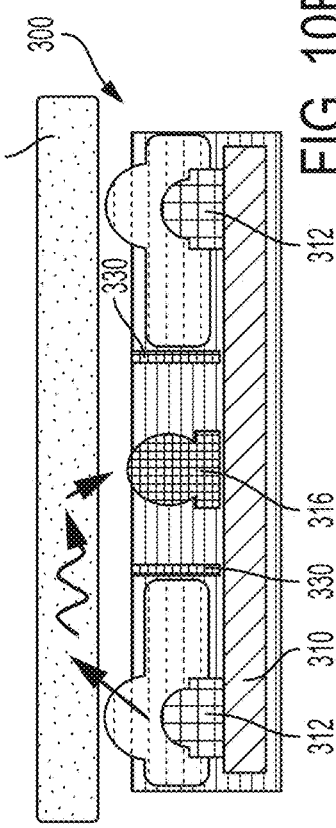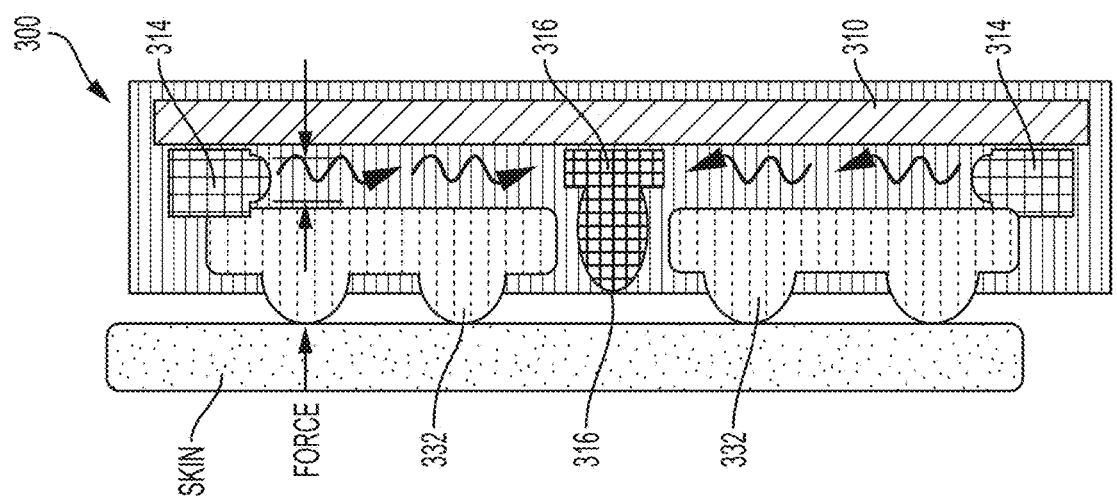

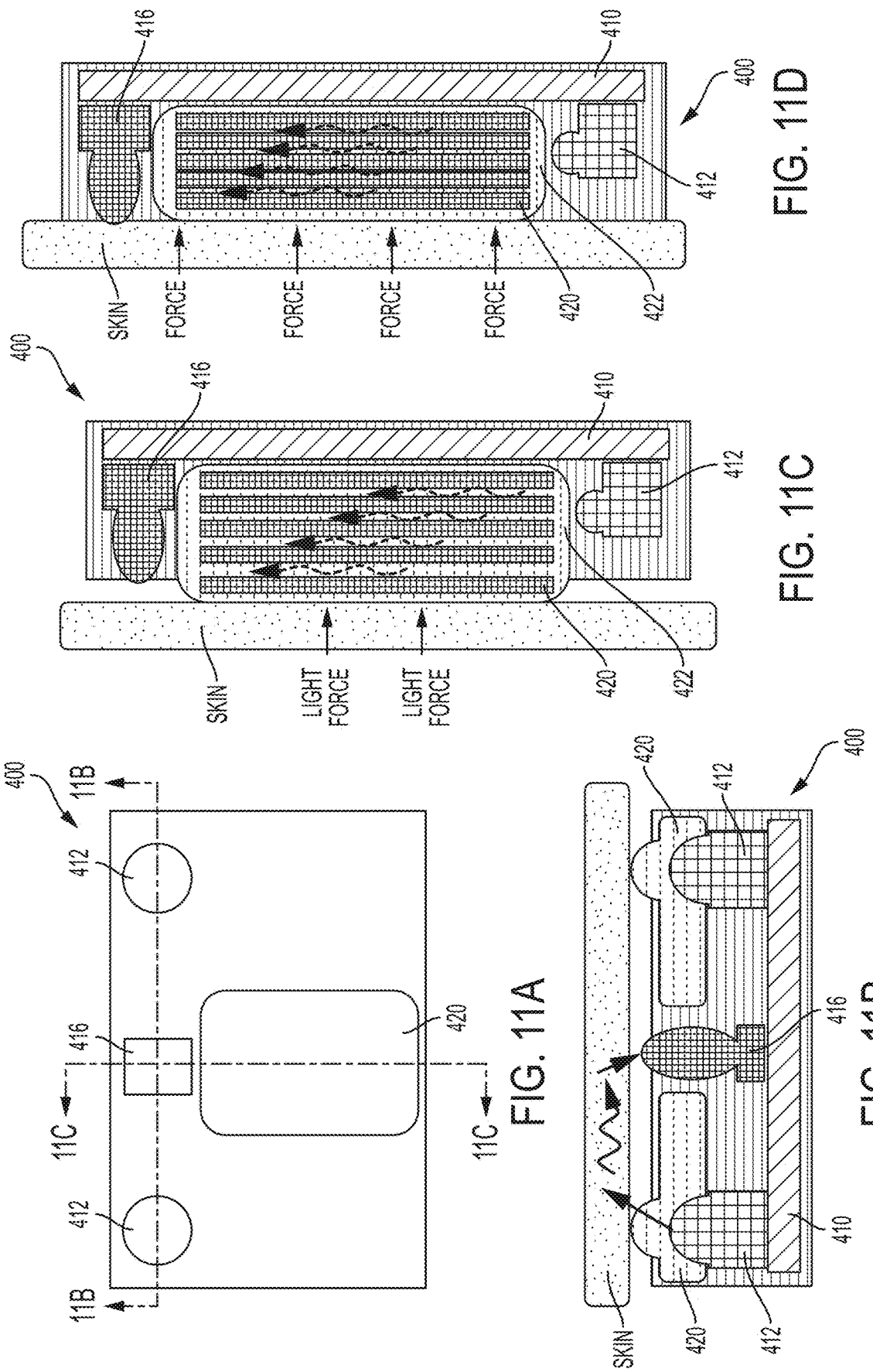

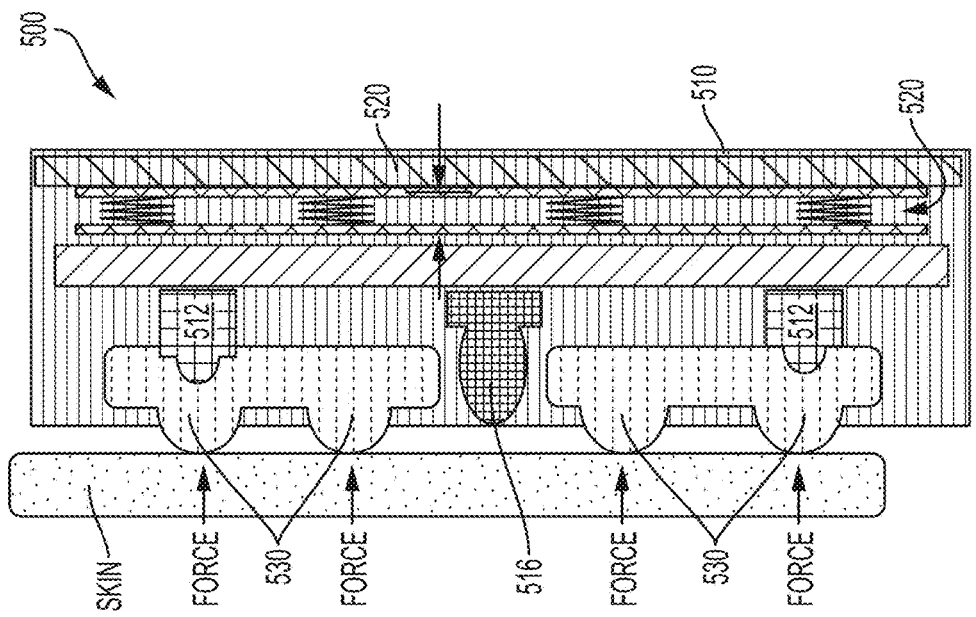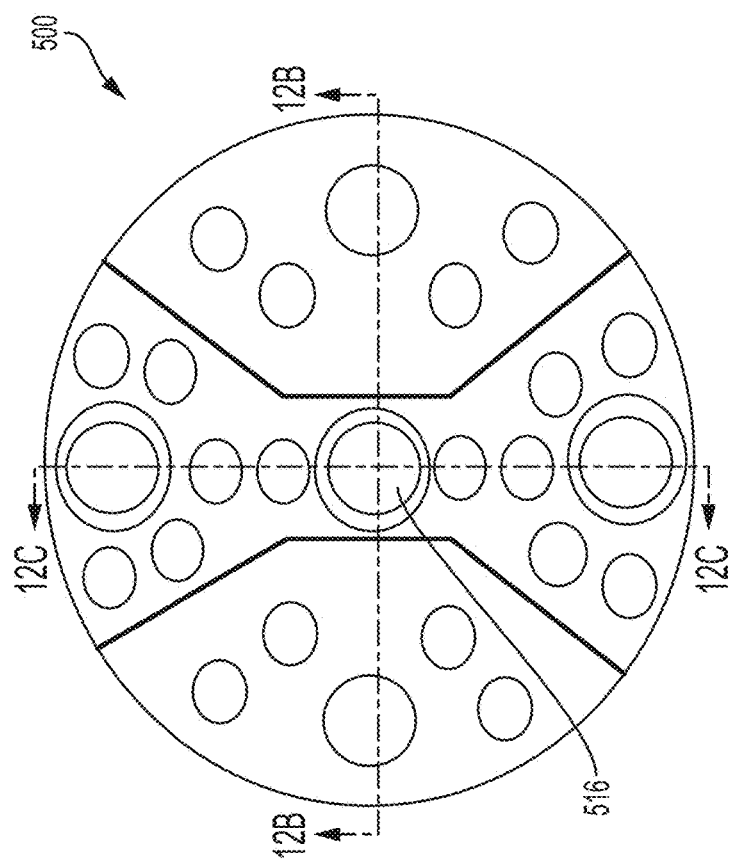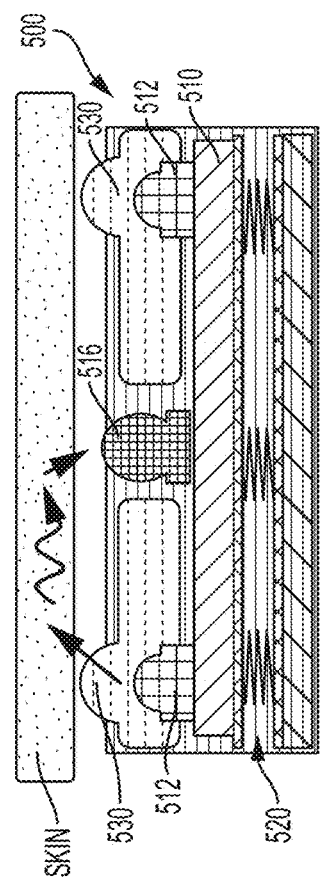

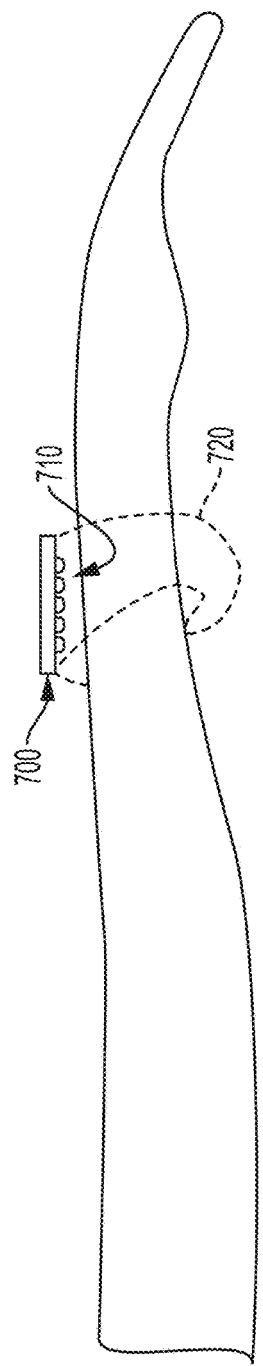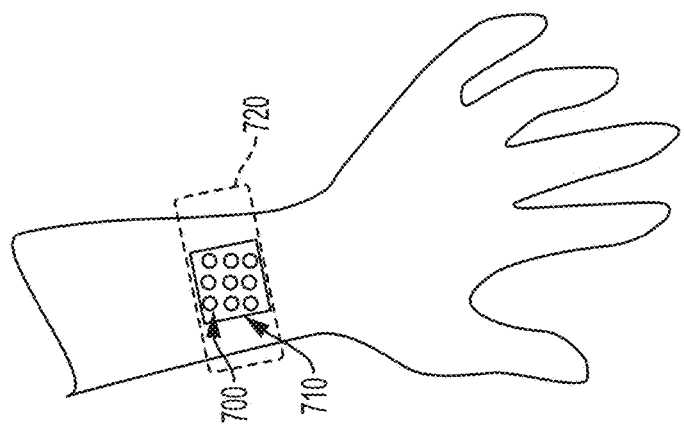

METHODS AND APPARATUS FOR DETECTING MOTION VIA OPTOMECHANICS

RELATED APPLICATIONS

This application is a continuation application of pending U.S. patent application Ser. No. 15/751,733, filed Feb. 9, 2018, which is a 35 U.S.C. § 371 national stage application of PCT Application No. PCT/US2016/046273, filed Aug. 10, 2016, which itself claims the benefit of and priority to U.S. Provisional Patent Application No. 62/204,214 filed Aug. 12, 2015, U.S. Provisional Patent Application No. 62/257,502 filed Nov. 19, 2015, and U.S. Provisional Patent Application No. 62/345,579 filed Jun. 3, 2016, the disclosures of all of which are incorporated herein by reference as if set forth in their entireties. The above-referenced PCT International Application was published in the English language as International Publication No. WO 2017/027551 A1 on Feb. 16, 2017.

FIELD OF THE INVENTION

The present invention relates generally to monitoring devices and methods and, more particularly, to monitoring devices and methods for measuring physiological information.

BACKGROUND OF THE INVENTION

Wearable devices capable of monitoring physiological information, such as heart rate, are increasingly being used. These devices come in various form factors, including devices configured to be worn at the ear or at other locations of the body, and including devices carried or worn by a person, such as smartphones, etc. U.S. Pat. Nos. 8,652,040, 8,700,111, 8,647,270, 8,788,002, 8,886,269, and 8,929,965, which are incorporated herein by reference in their entireties, describe various wearable devices configured to monitor physiological information, including headsets, earbuds, and wrist bands.

Physiological information obtained from a subject can be used to generate various types of health and fitness assessments of the subject. For example, using a photoplethysmography (PPG) sensor incorporated into a wearable monitoring device, blood flow information can be measured during daily activities of a subject and this information can be used to generate assessments, such as maximum oxygen consumption $VO_2max$, total energy expenditure (TEE), etc.

Unfortunately, a biometric signal from a physiological sensor of a wearable device typically includes subject motion-related noise, and PPG sensors are particularly sensitive to motion-related noise. Moreover, efforts to use accelerometer- or gyroscopic-based signals as motion noise references for cleaning up PPG signals have seen limited success, as these motion-related signals do not perfectly represent the motion noise characteristics reflected in PPG signals. As such, complex signal processing may be required in order to extract pure biometric information (i.e. heart rate, breathing rate) from motion-related noise embedded in the sensor signal.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the present invention facilitate the extraction of cleaner biometric signals from biometric monitors, such as PPG sensors and the like, by generating a motion reference signal independently from a biometric signal and then using this motion reference signal to remove motion artifacts from the biometric signal.

According to some embodiments of the present invention, a device for sensing physiological and body motion information includes at least one optical emitter and at least one optical detector, and at least two optical pathways. One optical pathway is configured to sense body motion information by sensing light from the at least one emitter scattered by body motion. The other optical pathway is configured to sense physiological information by sensing light from the at least one emitter scattered from the body by blood flow.

According to some embodiments of the present invention, a biometric sensor module includes a housing, a stabilizer member supported by the housing, at least one optical emitter supported by the housing, and at least one optical detector supported by the housing. The at least one optical emitter is configured to direct light into the body of the subject via a first optical pathway and to direct light at the stabilizer member along a second optical pathway. The first and second optical pathways may be optically isolated from each other. The at least one optical detector is configured to detect light from the body of the subject and generate a first signal comprising subject physiological information, and is also configured to detect light reflected by the stabilizer member and generate a second signal comprising subject motion information. The sensor module may include at least one signal processor configured to process the first and second signals so as to remove motion artifacts from the first signal.

In some embodiments, the stabilizer member may include an optical filter that is configured to pass, block, or scatter multiple different wavelengths of light representative of subject motion. In other embodiments, the at least one optical emitter may be configured to direct light into the body of the subject and/or at the stabilizer member in multiple different wavelengths.

In some embodiments, the at least one optical emitter includes a first optical emitter configured to direct light into the body of the subject via the first optical pathway, and a second optical emitter configured to direct light at the stabilizer member along the second optical pathway. The second optical emitter may include at least one optical element configured to direct light at the stabilizer member, such as a lens, filter, and/or reflective element.

In some embodiments, the at least one optical detector includes a first optical detector configured to detect light from the body of the subject and generate a first signal comprising subject physiological information, and a second optical detector configured to detect physically modulated light reflected by the stabilizer member and generate a second signal comprising subject motion information. The light reflected by the stabilizer member is physically modulated due to subject motion.

In some embodiments, the stabilizer member is movably supported by the housing and includes a portion that extends from the housing and is configured to engage the body of the subject.

In some embodiments, the first optical pathway and/or the second optical pathway comprises light guiding material.

In some embodiments, the housing comprises substantially opaque material.

In some embodiments, the sensor module is configured to be positioned at or within an ear of the subject. In other embodiments, the sensor module is configured to be secured to an appendage or other body location of the subject, or even integrated within clothing worn by the subject.

In some embodiments, the sensor module includes a blood flow stimulator configured to increase blood perfusion at a location of the body of the subject receiving light via the first optical pathway at or prior to the time when the at least one optical detector detects light from the body and generates a physiological information signal.

According to other embodiments of the present invention, a sensor module configured to be worn by a subject includes a housing, at least one optical emitter supported by the housing, and at least one optical detector supported by the housing. The at least one optical emitter is configured to direct light into the body of the subject via a first optical pathway and to direct light at the body along a second pathway. The first and second optical pathways may be optically isolated from each other. The at least one optical detector is configured to detect light from the body of the subject and generate a first signal comprising subject physiological information, and wherein the at least one optical detector is configured to detect light reflected by the body and generate a second signal comprising subject motion information. This reflected light may be physically modulated due to subject motion. The sensor module may include at least one signal processor configured to process the first and second signals so as to remove motion artifacts from the first signal.

In some embodiments, the at least one optical emitter includes a first optical emitter configured to direct light into the body of the subject via the first optical pathway, and a second optical emitter configured to direct light at the body along the second optical pathway.

In some embodiments, the at least one optical detector includes a first optical detector configured to detect light from the body of the subject and generate a first signal comprising subject physiological information, and a second optical detector configured to detect light reflected by the body and generate a second signal comprising subject motion information.

In some embodiments, the first optical pathway and/or the second optical pathway comprises light guiding material.

In some embodiments, the housing comprises substantially opaque material.

In some embodiments, the at least one optical emitter is configured to direct light into the body of the subject and/or at the body of the subject in multiple different wavelengths.

In some embodiments, the sensor module is configured to be positioned at or within an ear of the subject. In other embodiments, the sensor module is configured to be secured to an appendage or other body location of the subject, or even integrated within clothing worn by the subject.

In some embodiments, the sensor module includes a blood flow stimulator configured to increase blood perfusion at a location of the body of the subject receiving light via the first optical pathway at or prior to the time when the at least one optical detector detects light from the body and generates a physiological information signal.

According to other embodiments of the present invention, a sensor module configured to be worn by a subject includes a housing, at least one optical emitter and at least one optical detector supported by the housing, and a stabilizer member movably supported by the housing. The stabilizer member includes a portion that extends through a first aperture in the housing and is configured to engage the body of the subject. The at least one optical emitter is configured to direct light through a second aperture in the housing and into the body of the subject via a first optical pathway and to direct light at a portion of the stabilizer member within the housing along a second optical pathway. The first and second optical pathways may be optically isolated from each other. The at least one optical detector is configured to detect light from the body of the subject via a third aperture in the housing and generate a first signal comprising subject physiological information, and wherein the at least one optical detector is configured to detect light reflected by the stabilizer member and generate a second signal comprising subject motion information. The sensor module may include at least one signal processor configured to process the first and second signals so as to remove motion artifacts from the first signal.

In some embodiments, the at least one optical emitter includes at least one first optical emitter configured to direct light into the body of the subject via the first optical pathway, and at least one second optical emitter configured to direct light at the stabilizer member along the second optical pathway.

In some embodiments, a light guide is supported by the housing and the at least one optical emitter is configured to direct light into the body of the subject via the light guide. The light guide may include a plurality of portions that extend through respective apertures in the housing and that are configured to engage portions of the body of the subject.

In some embodiments, the housing is formed of substantially opaque material.

In some embodiments, the sensor module is configured to be positioned at or within an ear of the subject. In other embodiments, the sensor module is configured to be secured to an appendage or other body location of the subject, or even integrated within clothing worn by the subject.

In some embodiments, the sensor module includes a blood flow stimulator configured to increase blood perfusion at a location of the body of the subject receiving light via the first optical pathway at or prior to the time when the at least one optical detector detects light from the body and generates a physiological information signal.

According to other embodiments of the present invention, a sensor module configured to be worn by a subject includes a housing, first and second optical emitters supported by the housing, an optical detector supported by the housing, and first and second light guides supported by the housing. The first light guide is in optical communication with the first optical emitter and defines a first optical pathway, and the second light guide is in optical communication with the second optical emitter and defines a second optical pathway. The first and second optical pathways may be optically isolated from each other. The first optical emitter is configured to direct light into the body of the subject via the first optical pathway, and the second optical emitter is configured to direct light at the body of the subject via the second optical pathway. The optical detector is configured to detect light from the body of the subject and generate a first signal comprising subject physiological information. The optical detector also is configured to detect light reflected by the body of the subject and generate a second signal comprising subject motion information. The light reflected by the body may be physically modulated due to subject motion. The sensor module may include at least one signal processor configured to process the first and second signals so as to remove motion artifacts from the first signal.

In some embodiments, the first light guide includes a portion that extends through an aperture in the housing and is configured to engage the body of the subject.

In some embodiments, the housing is formed of substantially opaque material.

In some embodiments, the sensor module is configured to be positioned at or within an ear of the subject. In other embodiments, the sensor module is configured to be secured to an appendage or other body location of the subject, or even integrated within clothing worn by the subject.

In some embodiments, the sensor module includes a blood flow stimulator configured to increase blood perfusion at a location of the body of the subject receiving light via the first optical pathway at or prior to the time when the optical detector detects light from the body and generates a physiological information signal.

According to other embodiments of the present invention, a sensor module configured to be worn by a subject includes a housing, at least one optical detector supported by the housing, at least one optical emitter supported by the housing, and a stabilizer member movably supported by the housing. The stabilizer member includes a portion that extends from the housing and engages the body of the subject. The at least one optical emitter is configured to direct light into the body of the subject via a first optical pathway and to direct light at the at least one optical detector along a second optical pathway. The first and second optical pathways typically are optically isolated from each other. The stabilizer member is configured to modulate an amount of light in the second optical pathway by modulating a volume of the second optical pathway.

The at least one optical detector is configured to detect light from the body of the subject and generate a first signal containing subject physiological information. The at least one optical detector is configured to detect light in the second optical pathway and generate a second signal containing subject motion information. The sensor module may include at least one signal processor configured to process the first and second signals so as to remove motion artifacts from the first signal.

In some embodiments, the first optical pathway and/or the second optical pathway includes light guiding material.

In some embodiments, the second optical pathway includes a plurality of light channels, and the stabilizer member is configured to modulate an amount of light in the second optical pathway responsive to subject motion by modulating a volume of the plurality of light channels.

In some embodiments, the housing comprises substantially opaque material.

In some embodiments, the sensor module is configured to be positioned at or within an ear of the subject. In other embodiments, the sensor module is configured to be secured to an appendage or other body location of the subject, or even integrated within clothing worn by the subject.

In some embodiments, the sensor module includes a blood flow stimulator configured to increase blood perfusion at a location of the body of the subject receiving light via the first optical pathway at or prior to the time when the at least one optical detector detects light from the body and generates a physiological information signal.

According to other embodiments of the present invention, a sensor module configured to be worn by a subject includes a housing, a pressure transducer supported by the housing, at least one optical emitter supported by the housing, at least one optical detector supported by the housing, and a stabilizer member movably supported by the housing. The stabilizer member is configured to modulate the pressure transducer responsive to subject motion and includes a portion that extends from the housing and engages the body of the subject. The at least one optical emitter is configured to direct light into the body of the subject. The at least one optical detector is configured to detect light from the body of the subject and generate a first signal containing subject physiological information. The pressure transducer is configured to generate a second signal containing subject motion information. The sensor module may include at least one signal processor configured to process the first and second signals so as to remove motion artifacts from the first signal.

In some embodiments, the sensor module is configured to be positioned at or within an ear of the subject. In other embodiments, the sensor module is configured to be secured to an appendage of the subject, or even integrated within clothing worn by the subject.

In some embodiments, the sensor module includes a blood flow stimulator configured to increase blood perfusion at a location of the body of the subject receiving light via the at least one optical emitter at or prior to the time when the at least one optical detector detects light from the body and generates a physiological information signal.

According to other embodiments of the present invention, a method of removing motion artifacts from a biometric signal generated by a sensor module worn by a subject is provided. The sensor module includes a stabilizer member, at least one optical emitter, and at least one optical detector. The method includes directing light from the at least one optical emitter into the body of the subject via a first optical pathway, directing light from the at least one optical emitter at the stabilizer member along a second optical pathway, detecting light from the body of the subject and generating a first signal comprising subject physiological information, detecting light reflected by the stabilizer member and generating a second signal comprising subject motion information, and processing the first and second signals so as to remove motion artifacts from the first signal.

In some embodiments, the at least one optical emitter includes first and second optical emitters, and the method includes directing light from the first optical emitter into the body of the subject via the first optical pathway, and directing light from the second optical emitter at the stabilizer member along the second optical pathway.

In some embodiments, the at least one optical detector includes first and second optical detectors, and the method includes detecting light from the body of the subject and generating a first signal comprising subject physiological information via the first optical detector, and detecting physically modulated light reflected by the stabilizer member and generate a second signal comprising subject motion information via the second optical detector.

In some embodiments, the first and second optical pathways are optically isolated from each other.

According to other embodiments of the present invention, a method of removing motion artifacts from a biometric signal generated by a sensor module worn by a subject is provided. The sensor module includes at least one optical emitter and at least one optical detector and the method includes directing light from the at least one optical emitter into the body of the subject via a first optical pathway and at the body of the subject along a second optical pathway, detecting light from the body of the subject and generating a first signal containing subject physiological information, detecting light reflected by the body of the subject and generating a second signal containing subject motion information, and processing the first and second signals so as to remove motion artifacts from the first signal.

In some embodiments, the at least one optical emitter includes first and second optical emitters, and the method includes directing light from the first optical emitter into the body of the subject via the first optical pathway, and directing light from the second optical emitter at the body along the second optical pathway.

In some embodiments, the at least one optical detector includes first and second optical detectors, and the method includes detecting light from the body of the subject and generating a first signal containing subject physiological information via the first optical detector, and detecting light reflected by the body and generating a second signal containing subject motion information via the second optical detector.

In some embodiments, the first and second optical pathways are optically isolated from each other.

According to other embodiments of the present invention, a device, such as a smartphone or other portable electronic device, includes a sensor module configured to obtain physiological information from a body location of a subject, and a blood flow stimulator configured to increase blood perfusion at the body location at or prior to the time when the sensor module obtains the physiological information. The blood flow stimulator may include a heater, such as an infrared (IR) heater, configured to increase blood perfusion. In some embodiments the blood flow stimulator includes a mechanical actuator configured to apply physical stimulation to the body location. For example, in some embodiments, the device is a smartphone, and the blood flow stimulator is a vibration actuator within the smartphone configured to provide haptic feedback to a user.

In some embodiments, the sensor module includes a stabilizer member, at least one optical emitter, and at least one optical detector. The at least one optical emitter is configured to direct light into the body of the subject via a first optical pathway and to direct light at the stabilizer member along a second optical pathway. The at least one optical detector is configured to detect light from the body of the subject and generate a first signal comprising subject physiological information, and to detect light reflected by the stabilizer member and generate a second signal comprising subject motion information.

In some embodiments, the sensor module includes at least one optical emitter and at least one optical detector. The at least one optical emitter is configured to direct light into the body of the subject via a first optical pathway and to direct light at the body along a second pathway. The at least one optical detector is configured to detect light from the body of the subject and generate a first signal comprising subject physiological information, and to detect light reflected by the body and generate a second signal comprising subject motion information.

According to other embodiments of the present invention, a wearable device includes an optical sensor that is configured to detect optically derived physiological information from a location on a body of a subject, and that includes at least one optical emitter and at least one optical detector. The wearable device also includes a thermal energy generator configured to raise a temperature of the body at the location, a temperature sensor configured to sense body temperature information at the location, and at least one circuit configured to control electrical biasing of the at least one optical emitter, the thermal energy generator, and the temperature sensor. In addition, the wearable device includes data storage configured to receive and store data from the optical sensor and temperature sensor, and a processor that is configured to process data in the data storage from the optical sensor in context with data in the data storage from the temperature sensor to generate a physiological assessment for the subject.

In some embodiments, the at least one circuit is configured to electrically bias the at least one optical emitter at set time periods associated with electrical biasing of the thermal energy generator.

In some embodiments, the at least one optical emitter includes a plurality of optical emitters, and the at least one circuit is configured to alternately bias the plurality of optical emitters in time to generate a matrix of data including optical emitter wavelength information and temperature information.

In some embodiments, the optical sensor is configured to sense scattered light and luminescent light from the location, and wherein the at least one circuit is configured to alternately bias the plurality of optical emitters in time to generate a matrix of data including optical emitter wavelength information, temperature information, and time information.

In some embodiments, the at least one optical detector includes a plurality of optical detectors, and at least one of the plurality of optical detectors is configured to detect at least one wavelength of light that at least one other of the plurality of optical detectors is configured to not detect. Data from the plurality of optical detectors is used to generate a matrix of data including optical emitter wavelength information and temperature information.

According to other embodiments of the present invention, a wearable device includes a sensor module, such as a PPG sensor module, that is configured to obtain physiological information from a body location of a subject wearing the device. The wearable device also includes a bladder of compliant material that contains a fluid, such as a liquid, gas or gel. The bladder is configured to contact the skin of the subject at or adjacent the body location. The bladder may have various shapes and configurations. In some embodiments, the bladder has a ring shape that peripherally surrounds the sensor module.

A pressure sensor is provided that generates a signal proportional to a change in fluid pressure within the bladder. The change in pressure is responsive to motion of the subject. As such, the pressure sensor generates a motion noise reference signal that can be used to remove motion artifacts from the physiological information obtained by the sensor module.

In some embodiments, the bladder is configured to at least partially wrap around a limb of the subject.

In some embodiments, the bladder includes at least one fluid reservoir containing a fluid and a plurality of artificial blood vessels in fluid communication with the at least one fluid reservoir. Compression of the bladder due to subject motion causes the fluid to be forced from the at least one fluid reservoir into the artificial vessels, thereby creating pressure within the bladder that can be detected by the pressure sensor. Such a configuration may be useful to more closely resemble that of venous blood in the body, such that the artificial structure may generate a motion noise waveform that more closely resembles that of the subject's venous blood as it moves during motion, facilitating use as a noise reference as described above. It should be noted that the blood vessels and reservoir may further comprise at least one air bubble (air pocket) to facilitate fluid flow during motion. In some embodiments, the density of air bubbles and the viscosity of blood may be engineered to closely resemble that of the blood of the subject. In another embodiment, the fluid may comprise a plurality of fluids, each having a different density and/or polarity. Having such a distribution of fluids may more closely resemble the nature of the venous blood of the subject.

In some embodiments, the pressure sensor is a MEMS (micro-electromechanical systems) device, diaphragm, and/or actuator. In other embodiments, the pressure sensor is an optomechanical pressure sensor.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 10A illustrates an "internal" optomechanical biometric sensor module, according to some embodiments of the present invention.

FIG. 10B is a cross-sectional view of the sensor module of FIG. 10A taken along lines 10B-10B and illustrating the biometric information pathways.

FIG. 10C is a cross-sectional view of the sensor module of FIG. 10A taken along lines 10C-10C and illustrating the motion information pathways.

FIG. 11A illustrates an "internal" optomechanical biometric sensor module, according to some embodiments of the present invention.

FIG. 11B is a cross-sectional view of the sensor module of FIG. 11A taken along lines 11B-11B and illustrating the biometric information pathways.

FIG. 11C-11D are cross-sectional views of the sensor module of FIG. 11A taken along lines 11C-11C and illustrating the motion information pathways in an uncompressed and compressed configuration, respectively.

FIG. 12A illustrates an "internal" mechanical biometric sensor module, according to some embodiments of the present invention.

FIG. 12B is a cross-sectional view of the sensor module of FIG. 12A taken along lines 12B-12B of FIG. 12A.

FIG. 12C is a cross-sectional view of the sensor module of FIG. 12A taken along lines 12C-12C of FIG. 12A.

FIGS. 14A-14B illustrate an array of optomechanical sensors secured to an arm of a subject and configured to track gestural motion, according to some embodiments of the present invention.

DETAILED DESCRIPTION

Figure 1:
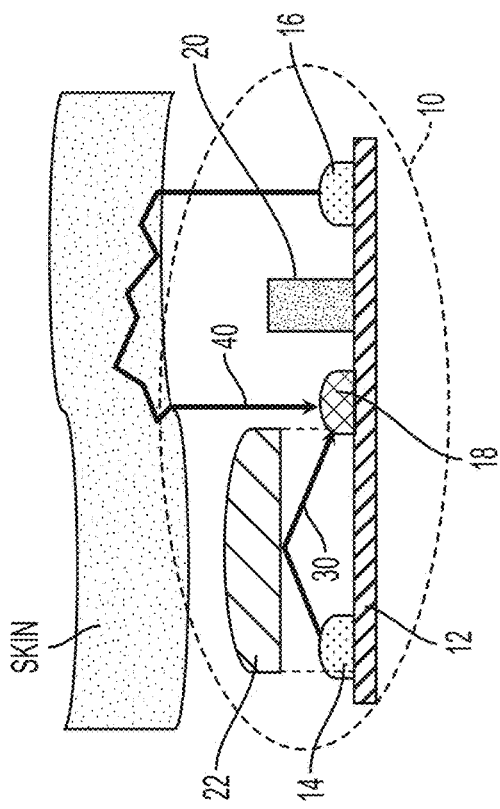
FIGS. 1-2 illustrate "internal" optomechanical biometric sensor modules and motion information and biometric information pathways generated thereby, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "secured", "connected", "attached" or "coupled" to another feature or element, it can be directly secured, directly connected, attached or coupled to the other feature or element or intervening features or elements may be present. In contrast, when a feature or element is referred to as being "directly secured", "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary more or less, for example by +/−20%, +/−10%, +/−5%, +/−1%, +/−0.5%, +/−0.1%, etc.

The term "circuit", as used herein, refers to an entirely software embodiment or an embodiment combining software and hardware aspects, features and/or components (including, for example, a processor and software associated therewith embedded therein and/or executable by, for programmatically directing and/or performing certain described actions, operations or method steps).

The term "photoplethysmography" (PPG), as used herein, refers to the method generating optical plethysmogram information from at least one region of the body and processing this information to generate biometric information derived from the optical plethysmogram information. A PPG sensor module refers to a small module comprising at least one optical emitter, at least one optical detector, and at least some signal processing electronics (analog and/or digital) to process the electrical signal from the optical detector. The PPG sensor module may additionally comprise optomechanics (optics and mechanical support) as well as a noise reference sensor, such as a motion sensor or the like, for detecting motion noise information that can be processed along with the optical detector information to attenuate motion artifacts from the desired PPG signal. Other types of noise references, such as environmental light (ambient light) noise references may also be integrated within the PPG sensor module to help attenuate ambient light noise from the desired PPG signal. When a plurality of optical emitters and/or detectors are integrated into the PPG sensor module, additional biometric information may be extracted, such as the determination of blood analyte (blood constituent) levels (such as oxygenated hemoglobin, deoxygenated hemoglobin, carboxyhemoglobin, methemoglobin, bilirubin, and the like). PPG sensor modules may be placed or worn across virtually any part or region of the body having blood flow, but such modules may more typically be proximal to the skin of an organism, such as the skin of the ear, forehead, nose, neck, chest, limbs (arms & legs), wrists, feet, digits (fingers & toes), or the like.

The term "metric", as used herein, generally refers to a measurement or measurement system of a property, and a "sensor metric" refers to a measurement or measurement system associated with a sensor. The metric may comprise an identifier for a type of measurement, a value of the measurement, and/or a diagnosis based on the measurement. For example, a metric may comprise "blood pressure", with a value of "120/80", and/or a diagnosis of "normal".

The term "biometric", as used herein, refers to a metric associated with physiological (biological) information. Thus, the term "biometric sensor" and "physiological sensor" are synonymous. For example, a "biometric optical sensor" may refer to an optical sensor configured for physiological monitoring. The "optical sensor" may refer to the optical detector itself or the complete PPG sensor comprising the optical emitters, detectors, noise references, and the like.

The terms "sensor", "sensing element", "sensor module", and "biometric sensor module", as used herein, are interchangeable and refer to a sensor element or group of sensor elements that may be utilized to sense information, such as information (e.g., physiological information, body motion, etc.) from the body of a subject and/or environmental information in a vicinity of the subject. A sensor/sensing element/sensor module may comprise one or more of the following: a detector element, an emitter element, a processing element, optics, mechanical support, supporting circuitry, and the like. Both a single sensor element and a collection of sensor elements may be considered a sensor, a sensing element, or a sensor module. Often times in this description, the reference to a "sensor element" refers to a fundamental component of a sensor module or discrete sensor, wherein the sensor module or discrete sensor comprises multiple sensor elements.

The term "optical emitter", as used herein, may include a single optical emitter and/or a plurality of separate optical emitters that are associated with each other.

The term "optical detector", as used herein, may include a single optical detector and/or a plurality of separate optical detectors that are associated with each other.

The term "wearable sensor module", as used herein, refers to a sensor module configured to be worn on or near the body of a subject.

The terms "monitoring device" and "biometric monitoring device", as used herein, are interchangeable and include any type of device, article, or clothing that may be worn by and/or attached to a subject and that includes at least one sensor/sensing element/sensor module. Exemplary monitoring devices may be embodied in an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "headset", as used herein, is intended to include any type of device or earpiece that may be attached to or near the ear (or ears) of a user and may have various configurations, without limitation. Headsets incorporating sensor modules, as described herein, may include mono headsets (a device having only one earbud, one earpiece, etc.) and stereo headsets (a device having two earbuds, two earpieces, etc.), true wireless headsets (having two wireless earpieces), earbuds, hearing aids, ear jewelry, face masks, headbands, glasses or eyewear, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination. The terms "headset" and "earphone", as used herein, are interchangeable.

The term "optomechanical", as used herein, refers to optical modulation with respect to mechanical energy in the general sense. The motion may be due to relative motion, absolute motion, vibration, pressure, force, etc. For example, generally in these inventions, the optomechanical sensor may be used to sense motion artifacts caused by any form of mechanical energy.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature.

The term "body" refers to the body of a subject (human or animal) that may wear a monitoring device, according to embodiments of the present invention.

The term "processor" is used broadly to refer to a signal processor or computing system or processing or computing method which may be localized or distributed. For example, a localized signal processor may comprise one or more signal processors or processing methods localized to a general location, such as to a wearable device. Examples of such wearable devices may comprise an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like, as well as smartphones and other devices carried or worn by a person. Examples of a distributed processor comprise "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuits), analog processing circuitry, or digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. Notwithstanding the foregoing, any wireless device (such as a portable device, for example) or system (such as a remote database for example) is considered remote to any other wireless device or system.

The terms "respiration rate" and "breathing rate", as used herein, are interchangeable.

The terms "heart rate" and "pulse rate", as used herein, are interchangeable.

The term "RRi" refers to "R-R interval" in a cardiac waveform (i.e., an electrocardiogram, photoplethysmogram, or the like) of a person. Generally, where heart rate is used in embodiments of the present invention, RRi may also be applied in a similar manner. However, RRi and heart rate are generally related in an inverse fashion, such that 1/RRi=instantaneous heart rate.

The term "thermal communication", as used herein, includes one or more of conductive transfer of thermal energy, convective transfer of thermal energy, and radiative transfer of thermal energy.

Various biometric parameters and activity parameters may be described herein by using the name of the parameter (such as "heart rate", $VO_2max$, and the like). Generally speaking, these names may refer to instantaneous values, averaged values, or some other processing of the associated parameter(s). For example, a breathing rate of 14 BPM (breaths per minute) may refer to an instantaneous measurement or an averaged measurement (for example, an average breathing rate of 14 BPM as averaged over 5 minutes). Unless "instantaneous", "average", or some other adjective is used to describe the parameter, it should not be assumed that there is a limitation with respect to the processing of the parameter.

In the following figures, various monitoring devices will be illustrated and described for attachment to the ear or an appendage of the human body, or even integrated within clothing. However, it is to be understood that embodiments of the present invention are not limited to those worn by humans. In addition, monitoring devices according to embodiments of the present invention may be worn at other locations of the body.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion. Accurate sensing of photoplethysmograms and heart rate from the ear has been demonstrated in regions between the concha and anti-tragus locations of the outer ear, and elsewhere at the ear.

Optical coupling into the blood vessels of the ear may vary between individuals. As used herein, the term "coupling" refers to the interaction or communication between excitation energy (such as light) entering or exiting a region and the region itself. For example, one form of optical coupling may be the interaction between excitation light generated from within an optical sensor of an earbud (or other device positioned at or within an ear) and the blood vessels of the ear. In one embodiment, this interaction may involve excitation light entering the ear region and scattering from a blood vessel in the ear such that the temporal change in intensity of scattered light is proportional to a temporal change in blood flow within the blood vessel. Another form of optical coupling may be the interaction between excitation light generated by an optical emitter within an earbud and a light-guiding region of the earbud. Thus, an earbud with integrated light-guiding capabilities, wherein light can be guided to multiple and/or select regions along the earbud, can assure that each individual wearing the earbud will generate an optical signal related to blood flow through the blood vessels. Optical coupling of light to a particular ear region of one person may not yield photoplethysmographic signals for each person. Therefore, coupling light to multiple regions may assure that at least one blood-vessel-rich region will be interrogated for each person wearing an earbud. Coupling multiple regions of the ear to light may also be accomplished by diffusing light from a light source within an earbud.

Another example of optical coupling is the coupling of scattered light from the body of a subject to light-guiding optics that guide light towards a photodetector. The term "coupling", however, may also refer to mechanical coupling, electrical coupling, optomechanical coupling, or the like, and not just optical coupling. As an example of optomechanical coupling, the optical coupling of a light guide from an optical emitter to the body of a subject may also be associated with the mechanical coupling of the light guide (or of another optical pathway) to the body of a subject.

Referring to FIGS. 1-6, biometric sensor modules 10 that may be incorporated into various wearable devices are illustrated. The illustrated sensor modules 10 may be integrated into various wearable devices/apparel including, but not limited to, an earbud, a wristband, an armband, a smartphone, clothing and accessory apparel, or any other wearable form-factor for a digit, limb, torso, head, ear, face, and the like. Each sensor module 10 is configured to capture motion information from the body of a subject via optomechanical coupling between the body and the sensor module 10. The captured motion information serves as a noise reference for filtering motion noise (motion artifacts) from biometric sensor signals. In the embodiment illustrated in FIG. 1, a sensor module (e.g., a PPG sensor module, etc.) 10 includes a base 12, such as a printed circuit board (PCB), that supports first and second optical emitters 14, 16, and an optical detector 18. An optical barrier 20 is provided to prevent light emitted by the emitter 16 from directly entering or saturating the optical detector 18. The illustrated sensor module 10 also includes a stabilizer member 22 that is configured to transfer motion information from the body of a subject wearing the sensor module 10 to the optical detector 18. The stabilizer member 22 may also be referred to as a light modulating (or light regulating) mechanism. In addition to helping transfer subject motion information caused by mechanical energy (i.e., the force of the subject body against the stabilizer member 22 as a result of subject motion), the stabilizer member 22 may also be configured to help stabilize the sensor module 10 against the skin.

The physical dimensions of the biometric sensor modules of FIGS. 1-6 are such that they are small enough to be wearable but large enough to support the optics, electronics, and powering components. Considering a top-view, typical dimensions for the modules may be on the order of ~1 mm-20 mm in length/diameter and the associated optics may be on the order of 100 microns-3 mm in length diameter. However, smaller and larger sizes may be utilized, and embodiments of the present invention are not limited to any particular sizes or dimensions.

The illustrated sensor module 10 produces two optical pathways 30, 40. The first optical pathway 30 (also referred to as the "motion information pathway") is created by light emitted by the first optical emitter 12 and reflected off of the stabilizer member 22. The second pathway 40 (also referred to as the "biometric information pathway") is created by light emitted by the second optical emitter 16 that is absorbed, scattered, and/or reflected by tissue, blood vessels, etc., within the body of the subject. The biometric information pathway 40 contains a higher level of subject physiological information than the motion information pathway 30, which contains a higher level of subject motion information.

Figure 2:
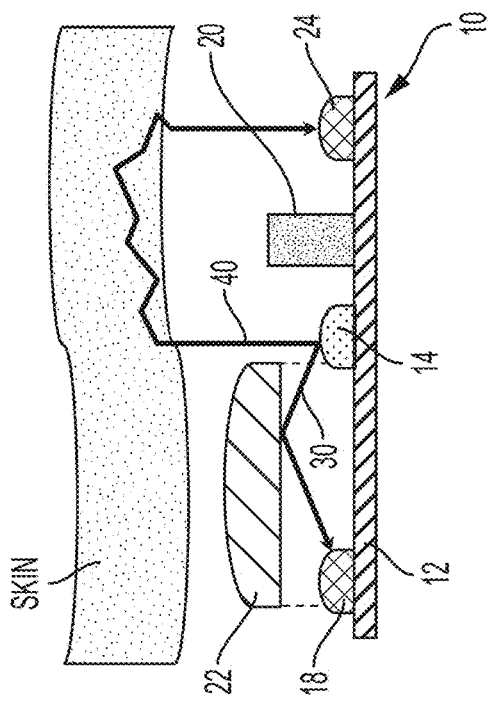

The embodiment illustrated in FIG. 2 is similar to the embodiment of FIG. 1 except that a single optical emitter is utilized to create both the motion information optical pathway 30 and the biometric information optical pathway 40. The illustrated sensor module (e.g., a PPG sensor module, etc.) 10 includes a base 12, such as a PCB, an optical emitter 14, first and second optical detectors 18, 24, and an optical barrier 20. As discussed above, the optical barrier 20 is configured to prevent light emitted by the emitter 14 from directly entering/saturating the optical detector 18. The illustrated sensor module 10 also includes a stabilizer member 22 that is configured to transfer motion information from the body of a subject wearing the biometric sensor module 10, as well as stabilize the biometric monitor 10 relative to the skin of the subject. As with the embodiment of FIG. 1, the illustrated sensor module 10 produces a motion information pathway 30 and a biometric information pathway 40. The emitter 14 is configured to direct light towards the stabilizer member 22 to create the motion information pathway 30 and is also configured to direct light towards the skin of the subject such that the light can be absorbed, scattered, and/or reflected by tissue, blood vessels, etc., within the body of the subject.

Figure 3:
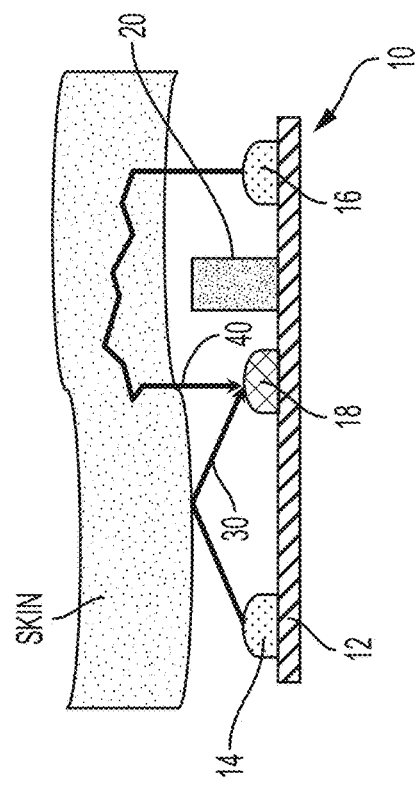
FIGS. 3-5 illustrate "external" optomechanical biometric sensor modules and motion information and biometric information pathways generated thereby, according to some embodiments of the present invention.

The embodiment illustrated in FIG. 3 is similar to the embodiment of FIG. 1 except that a stabilizer member is not utilized. The illustrated sensor module (e.g., a PPG sensor module, etc.) 10 includes a base 12, such as a PCB, supporting first and second optical emitters 14, 16, and optical detector 18, and an optical barrier 20. As discussed above, the optical barrier 20 is configured to prevent light emitted by the emitter 16 from directly entering/saturating the optical detector 18. As with the embodiment of FIG. 1, the illustrated sensor module 10 produces a motion information optical pathway 30 and a biometric information optical pathway 40. However, the motion information pathway 30 is created by the first emitter 14 directing light towards the subject so that the light reflects directly off of the skin, without substantial interaction with blood flow-rich tissue, and is detected by the optical detector 18.

Figure 4:
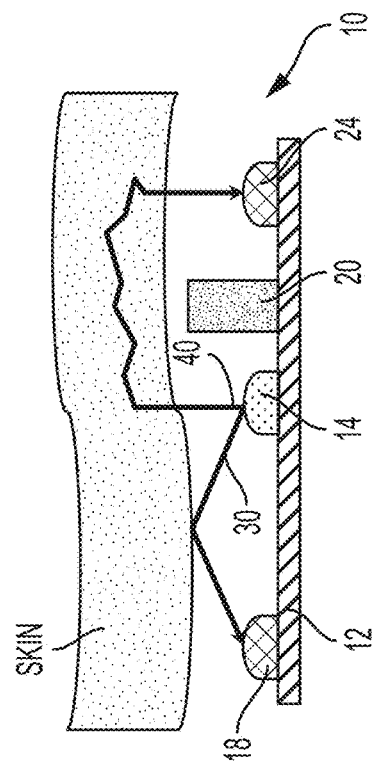

The embodiment illustrated in FIG. 4 is similar to the embodiment of FIG. 2 except that a stabilizer member is not utilized. The illustrated sensor module (e.g., a PPG sensor module, etc.) 10 includes a base 12, such as a PCB, supporting an optical emitter 14, first and second optical detectors 18, 24, and an optical barrier 20. As discussed above, the optical barrier 20 is configured to prevent light emitted by the emitter 16 from directly entering/saturating the optical detector 18. As with the embodiment of FIG. 2, the illustrated sensor module 10 produces a motion information optical pathway 30 and a biometric information optical pathway 40. However, the motion information pathway 30 is created by the emitter 14 directing light towards the subject so that the light reflects directly off of the skin, without substantial interaction with blood flow-rich tissue, and is detected by the optical detector 18. The single emitter 14 is also configured to direct light towards the skin of the subject such that the light can be absorbed, scattered, and/or reflected by tissue, blood vessels, etc., within the skin of the subject.

The sensor modules illustrated in FIGS. 1 and 2 are referred to as "internal" optomechanical sensor modules (because the motion pathway modulation happens via an internal motion, i.e., the stabilizer member motion), and the sensor modules of FIGS. 3 and 4 are referred to as "external" optomechanical sensor modules (because the motion pathway modulation happens via an external motion, i.e., motion between the skin and the body). Each of the embodiments illustrated in FIGS. 1-4 work by physically modulating light in response to motion between the body of the subject wearing the sensor module 10 and the sensor module 10. In FIGS. 1 and 2, the stabilizer member 22 is used to transfer motion information from the body of the subject via the motion information pathway 30. In contrast, for the "external" embodiments of FIGS. 3 and 4, physical modulation is achieved by relative motion between the body of the subject and the biometric sensor module 10, itself.

In each of the embodiments of FIGS. 1-4, the motion information pathway 30 contains little or no physiological information. As such, by processing the two separate signals created by the two optical pathways (i.e., the motion information pathway 30 and the biometric information pathway 40) via a circuit or processor, motion noise information may be attenuated and the biometric signal information may be preserved or amplified. In some embodiments, the attenuation of motion artifacts, by processing the two separate signals, may be executed in analog space (via analog comparator methods, differential amplification, analog adaptive filtering, or the like) or in digital space (via spectral subtraction, digital adaptive filtering, variable filtering, or the like).

For embodiments as illustrated in FIGS. 1-4, it should be noted that, because the signal pathways for biometrics 40 and motion 30 are distinct, modulation of the electrical power feeding the optical emitter(s) is not critical for embodiments of the present invention to operate. Thus, embodiments of the present invention may work during steady state (DC) powering conditions without modulating power to the optical emitter or detector. However, modulating the optical emitters is indeed permitted in these configurations and may be useful for digital signal processing (in general) and for removing ambient light noise. As a specific example, ambient light may be attenuated from a PPG signal output by subtracting optical detector signals collected when the optical emitter is shut off from optical detector signals collected when the optical emitter is turned on. As another example, for the embodiments having at least two optical emitters (such as illustrated in FIGS. 1 and 3), the emitters may be modulated in an alternating fashion, where only one emitter is generating light at a given time. This may help prevent optical cross-talk from contaminating the optical detector readings when assessing the biometric signal pathway 40 vs. the motion signal pathway 30.

Figure 5:
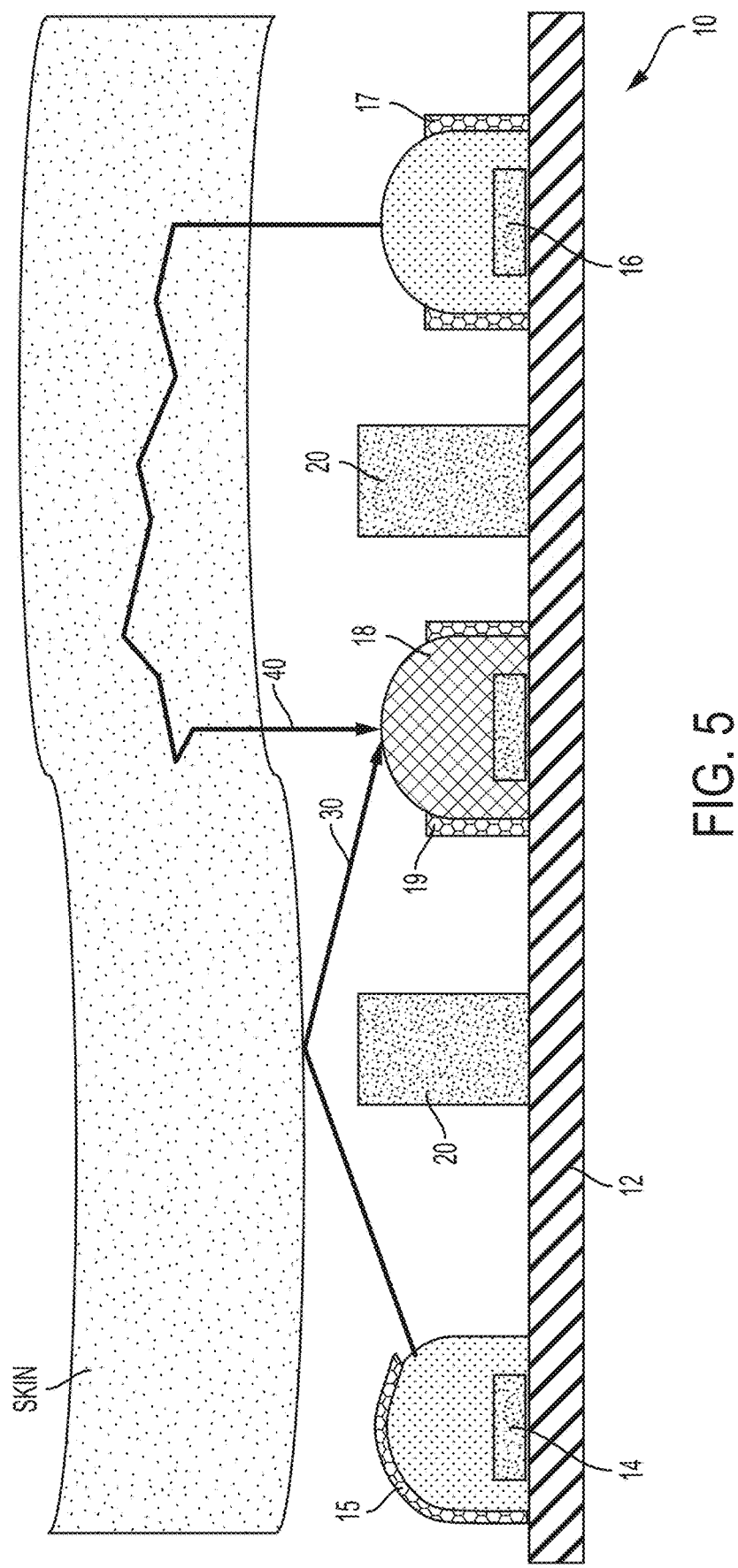

Referring to FIG. 5, an external optomechanical sensor module (e.g., a PPG sensor module, etc.) 10, according to other embodiments of the present invention, is illustrated. The illustrated sensor module 10 may be integrated into various wearable devices including, but not limited to, an earbud, a wristband, an armband, a smartphone, or any wearable form-factor for a digit, limb, torso, head, ear, face, and the like. The embodiment illustrated in FIG. 5 is similar to the embodiment of FIG. 3 except that various optical elements (e.g., an optical filter, an optical lens, etc.) are utilized with the optical emitters 14, 16, and with the detector 18. For example, one or more optical elements 15 are associated with the emitter 14 to help steer light so as to be reflected from the skin of the user to generate the motion information optical pathway 30. One or more optical elements 17 are associated with the emitter 17 to help steer light so as to enter the skin of the subject and to generate the biometric information optical pathway 40. One or more optical elements 19 are associated with the optical detector and facilitate detection of the light from each of the motion information pathway 30 and the biometric information pathway 40. Examples of suitable optical elements include light guides, light reflectors, light cladding, or the like. In the illustrated embodiment, a barrier 20 is positioned between the detector 18 and each of the emitters 14, 16, and each barrier 20 is configured to prevent light emitted by the emitters 14, 16 from directly entering/saturating the optical detector 18.

It should be noted that a combined external and internal optomechanical sensor module may also be produced by combining external pathway components and internal pathway components on the same module. In such case, it may be preferable to have at least one optical detector associated with each pathway, such that at least one detector is associated with the external pathway and at least one detector is associated with the internal pathway. Alternatively, one detector may be used by alternately powering the emitters associated with each pathway, such that a single emitter (or multiple emitters) from only one pathway is powered on at any given time.

Figure 6:
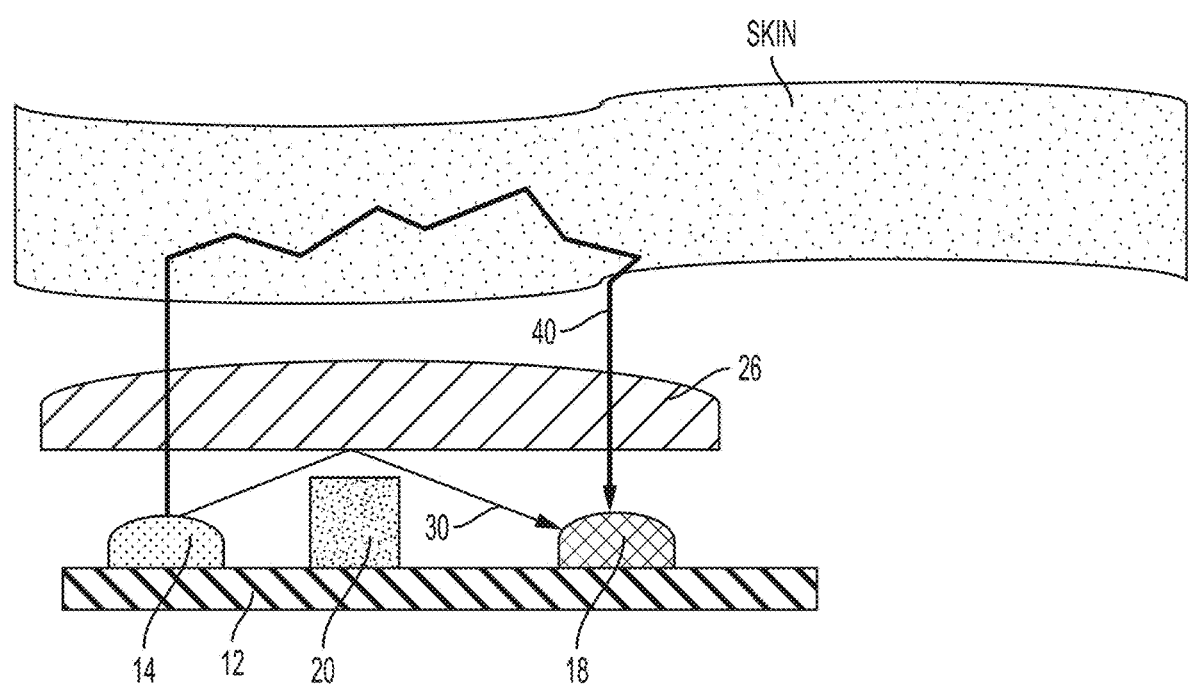
FIG. 6 illustrates an "internal" optomechanical biometric sensor module and motion information and biometric information pathways generated thereby, according to some embodiments of the present invention.

In other embodiments of the present invention, as illustrated in FIG. 6, an internal optomechanical sensor module 10 may generate both a motion sensing pathway 30 and a biometric signal pathway 40 via a single optical emitter 14 and a single optical detector 18. The illustrated sensor module 10 may be integrated into various wearable devices including, but not limited to, an earbud, a wristband, an armband, a smartphone, or any wearable form-factor for a digit, limb, torso, head, ear, face, and the like. A stabilizer member 26 incorporates one or more optical filters to pass, block, or scatter distinguishable wavelengths or wavelength bands. For example, some optical wavelengths from the optical emitter 14 may pass through the stabilizer member 26 and pass through the biometric signal pathway 40, whereas other optical wavelengths may be scattered by the stabilizer member 26 and pass through the motion sensing pathway.

In the illustrated embodiment, the optical emitter 14 is configured to generate at least two distinguishable wavelengths of electromagnetic energy at distinguishably separate time periods, and/or the optical detector 18 is configured to discriminate between at least two distinguishable wavelengths. For example, the optical emitter 14 may comprise at least two separate emitters (such as with an LED array or mesa array, etc.) which alternate emission intensity in time, and the detector 18 may be configured to sense each wavelength separately in time. As another example, the optical emitter 14 may be configured to generate multiple wavelengths simultaneously (i.e., not alternating in time), and the detector 18 may comprise at least two distinct detecting regions (such as photodiodes or mesa arrays, etc.) each associated with a different optical filter, such that the detector 18 can sense each wavelength simultaneously via a separate detecting region or "channel". An important benefit of the internal optomechanical sensor configuration of FIG. 6 is that a single optical emitter and single optical detector may be used, unlike the embodiments presented in FIG. 1 and FIG. 2.

Referring now to FIGS. 7A-7D, an "external" optomechanical sensor module (e.g., a PPG sensor module, etc.) 100 that can generate both a motion information optical pathway 30 and a biometric information optical pathway 40, according to some embodiments of the present invention, is illustrated. The illustrated biometric sensor module 100 may be integrated into various wearable devices including, but not limited to, an earbud, a wristband, an armband, a smartphone or any wearable form-factor for a digit, limb, torso, head, ear, face, and the like. The illustrated sensor module 100 includes a housing 102 with a generally rectangular configuration. However, embodiments of the present invention are not limited to the illustrated configuration of the biometric sensor module 100. The sensor module 100 may have any shape, such as triangular, polygonal, round, etc. The housing 102 may be formed of substantially opaque material.

The size of the sensor module 100 may be determined in part by the location of the body where the sensor module 100 is positioned. For example, a smaller sensor module 100 may be better suited for the ear or along a muscle group, whereas a larger sensor module 100 may be better suited for a flat surface, such as the wrist or forearm, etc. However, the sensor module 100 should ideally be configured to be small enough to not "rock" on multiple muscle groups as they independently flex.

Figure 7B:
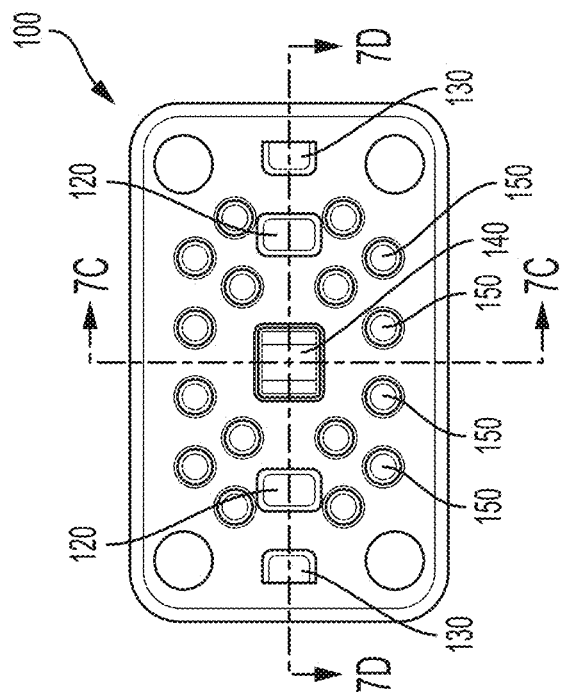
FIG. 7B is a top plan view of the sensor module of FIG. 7A.
Figure 7D:
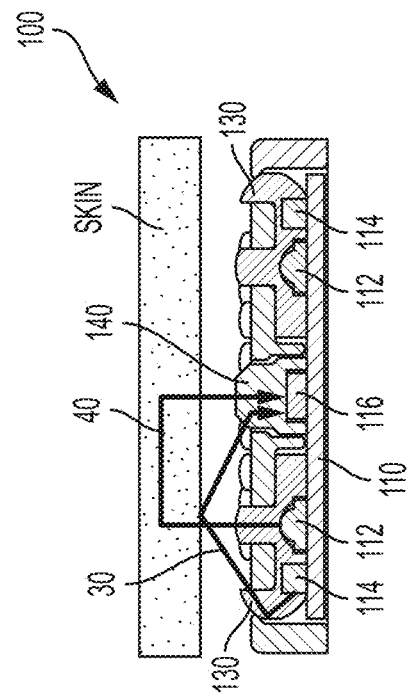
FIG. 7D is a cross-sectional view of the sensor module of FIG. 7B taken along lines 7D-7D in FIG. 7B.
Figure 7A:
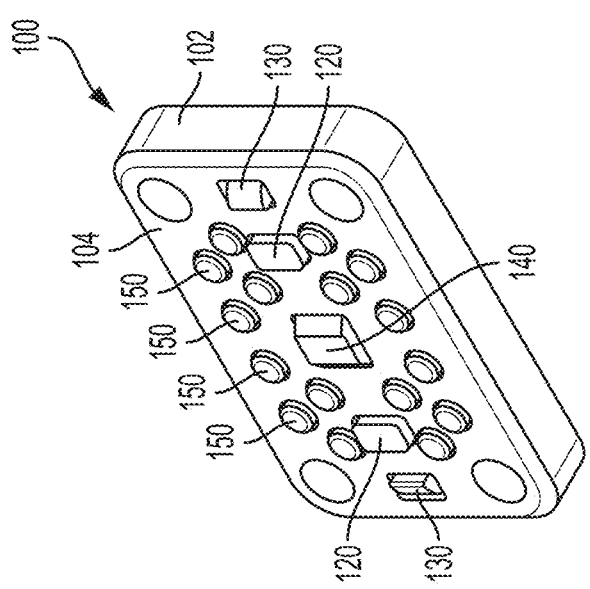
FIG. 7A illustrates an "external" optomechanical biometric sensor module, according to some embodiments of the present invention.
Figure 7C:
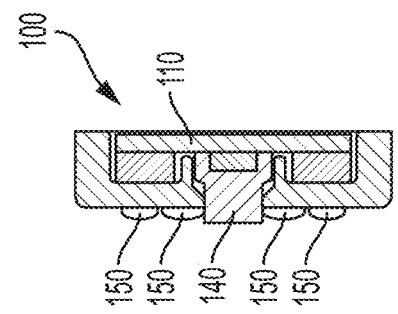
FIG. 7C is a cross-sectional view of the sensor module of FIG. 7B taken along lines 7C-7C in FIG. 7B.

Within the sensor module housing 102 is a base 110, such as a PCB, that supports a first pair of optical emitters 112, a second pair of optical emitters 114, and an optical detector 116. Exemplary optical emitters 112, 114 include, but are not limited to light-emitting diodes (LEDs), laser diodes (LDs), compact incandescent bulbs, organic LEDs (OLEDs), micro-plasma emitters, IR blackbody sources, or the like. A light guide 120 is in optical communication with each optical emitter 112 and is shaped and configured to direct light emitted from each emitter 112 into the skin of a subject wearing the sensor module 100 so as to generate a biometric information pathway 40 (FIG. 7D). A light guide 130 is in optical communication with each optical emitter 114 and is shaped and configured to direct light so as to be reflected off of the skin of the subject and to create a motion information pathway 30 (FIG. 7D).

A light guide 140 is in optical communication with the detector 114 and is configured to collect light from both the motion information pathway 30 and the biometric information pathway 40 and deliver collected light to the optical detector 114. In some embodiments, the light guide 140 may include reflective material along the sidewalls thereof to facilitate directing light to the optical detector. In addition, the light guide 140 may have various shapes and configurations that can be used to collect light for detection.

The illustrated sensor module 100 also includes a plurality of stabilizer members 150 that are configured to stabilize the sensor module 100 when in contact with the skin of a subject. The light guides 120, 130, the detector light guide 140, and the plurality of stabilizer members 150 extend outwardly from the housing 102 through respective apertures formed within the outer surface 104 of the housing 102, as illustrated. It should be noted that, in this particular embodiment, the stabilizer members 150 are not configured to modulate a motion pathway. Namely, these stabilizers 150 are used solely for stabilizing the sensor module 100 against the body of the subject.

In use, the sensor module 100 is positioned against the skin of a subject, for example via a strap or band, and optical emitters 112 emit light through light guides 120 and into the body. The light propagates through the body and then enters the light guide 140 that directs the light to the light detector 116. Optical emitters 114 emit light through light guides 130 which direct the light to reflect off of the body of the subject and enter the light guide 140 so as to be detected by the detector 116 and substantially without entering the body. Light from the optical emitters 112 is turned on (modulated) at different times from light from the optical emitters 114 and the detector 116 is able to discriminate light containing biometric information (i.e., light in the biometric information pathway 40) from light containing motion information (i.e., light in the motion information pathway 30). Signals generated by the light detector 116 for detected light containing motion information and detected light containing biometric information are sent to a processor and, together with any other reference signals, used to extract purely biometric information.

In one mode of operation, the emitters 112, 114 may be alternately modulated in time, such as with pulsing or biasing, such that signal processing can be used to identify motion information in the motion information pathway 30 and biometric information in the biometric information pathway 40. Then, an analog or digital filter may be implemented to process both the motion information and biometric information to selectively attenuate motion artifact information from the biometric information.

Light in the motion information pathway 30 is modulated mostly by motion artifacts, such as optical scatter from the skin interface, as the sensor module housing 102 moves up and down and side-to-side against the skin of the subject wearing the sensor module 100. In contrast, light in the biometric information pathway may be both physically modulated by subject motion and physiologically modulated by being absorbed, scattered, and/or reflected by tissue, blood vessels, etc., within the body of the subject.

In some embodiments, the optical emitters 114 may emit light at a shorter wavelength than light emitted by the optical emitters 112. Shorter wavelength light may not penetrate as deeply into the skin as longer wavelength light, thereby reducing the intensity of biometric information in the motion information pathway 30. In some embodiments, optical emitters 114 emit light at optical wavelengths shorter than 470 nm. In other embodiments, optical emitters 114 emit light at optical wavelengths shorter than 420 nm. However, optical emitters that can emit light at any optical wavelength can be used for the emitters 114, including wavelengths longer than that generated by the optical emitters 112 in the biometric signal pathway. However, wavelengths shorter than 280 nanometers and longer than 5 microns may be more challenging to effectively implement partly due to high absorption of the shorter wavelengths and waveguiding effects at larger wavelengths. Moreover, solid state optical detectors may exhibit extremely low sensitivity for wavelengths shorter than 280 nanometers and may be extremely noisy (especially at room temperature and higher) for wavelengths greater than 2 microns.

As discussed above, some biometric information (e.g., PPG information) may be included in the motion information pathway 30 because at least some light may interact with blood flow at the skin surface. As a result scattered light received by the detector 116 may at least partially comprise biometric information, which is undesirable, as in such case it may be difficult to use the motion pathway signal as a noise reference for cleaning up a photoplethysmogram. Thus, in some embodiments of the present invention, the light guides 130 are configured such that light emitted by the optical emitters 114 is steered to scatter from the skin at large angles which may discourage absorption at the skin. As illustrated in FIG. 7D, the senor module 100 is configured such that light scatters from light guide 130 to propagate towards the skin at a large angle and scatter off and/or guide along the skin surface towards the detector light guide 140.

Referring now to FIGS. 8A-8B and FIGS. 9A-9D, an "internal" optomechanical sensor module (e.g., a PPG sensor module, etc.) 200 that can generate both a motion information optical pathway 30 and a biometric information optical pathway 40, according to some embodiments of the present invention, is illustrated. The illustrated biometric sensor module 200 may be integrated into various wearable devices including, but not limited to, an earbud, a wristband, an armband, a smartphone or any wearable form-factor for a digit, limb, torso, head, ear, face, and the like. The illustrated sensor module 200 includes a housing 202 having first and second portions 204, 206 that are secured together via fasteners F. In the illustrated embodiment, each fastener F is a screw or other threaded member that is inserted through the housing second portion 206 and threadingly engages a threaded insert 207 secured to the first housing portion 204. However, embodiments of the present invention are not limited to the use of threaded fasteners. Various ways may be utilized to secure the housing first and second portions 204, 206 together, as would be understood by one skilled in the art. In some embodiments, one or both of the housing first and second portions 204, 206 are formed of substantially opaque material to help prevent ambient light intrusion and hence optical signal corruption.

The illustrated sensor module 200 has a generally round configuration. However, embodiments of the present invention are not limited to the illustrated configuration of the sensor module 200. The sensor module 200 may have any shape, such as triangular, polygonal, rectangular, etc. In addition, the size of the sensor module 200 may be determined in part by the location of the body where the sensor module 200 is positioned. For example, a smaller sensor module 200 may be better suited for the ear or along a muscle group, whereas a larger sensor module 100 may be better suited for a flat surface, such as the wrist or forearm. However, the sensor module 200 should ideally be small enough to not "rock" on multiple muscle groups as they independently flex.

Positioned within the housing 202 of the sensor module 200 is a base 210, such as a PCB, that supports optical emitters 212, 214 and optical detector 216. Also positioned within the housing 202 is a light guide 220 that is configured to be in optical communication with optical emitters 212, a stabilizer pad 230, and a light guide 240 that is configured to be in optical communication with the optical detector 216.

The illustrated light guide 220 includes a plurality of elements 222 extending outwardly from one side thereof that are configured to extend through respective apertures 203 in the first housing portion 204. These elements 222 are not meant to transfer motion information, unlike stabilizing members 232 and 234, but rather are used for stabilizing (supporting) the sensor at the body.

The light guide 220 also includes elements 224 that extend through apertures 205 in the first housing portion 204 that are configured to guide light from emitters 212 into the body of a subject wearing the sensor module 200. The light guide 220 is also configured to internally guide light from the emitters 214 towards the stabilizer members 232, 234 of the stabilizer pad 230.

The illustrated stabilizer pad 230 includes a first pair of stabilizer members 232 extending outwardly therefrom that are configured to extend through respective apertures 207 in the first housing portion 204. The illustrated stabilizer pad 230 also includes two pair of stabilizer members 234 extending outwardly therefrom that are configured to extend through respective apertures 209 in the first housing portion 204. The stabilizer members 232, 234 are configured to contact the skin of a subject and move in response to subject motion. Light from the optical emitters 214 is directed towards the stabilizer members 232, 234 via either the light guide 220 or via an empty pocket in the pad 230 in order to create respective motion information pathways 30, as will be described below.

In the illustrated embodiment, the light guide 220 and stabilizer pad 230 are integrated as one unit and referred to as a "multi-shot" lens. The illustrated multi-shot lens may be fabricated by directing two types of plastic into a mold (transparent+opaque), such that there are no seams between the two regions. As a result, the multi-shot lens can prevent the leakage of moisture, such as sweat from a subject wearing the sensor module 200, into the electronics. The transparent portion of the lens is configured for light guiding. The opaque region is configured for optomechanical sensing (i.e., motion sensing) as described above. However, in other embodiments, the light guide 220 and stabilizer pad 230 may be separate elements.

Figure 8A:
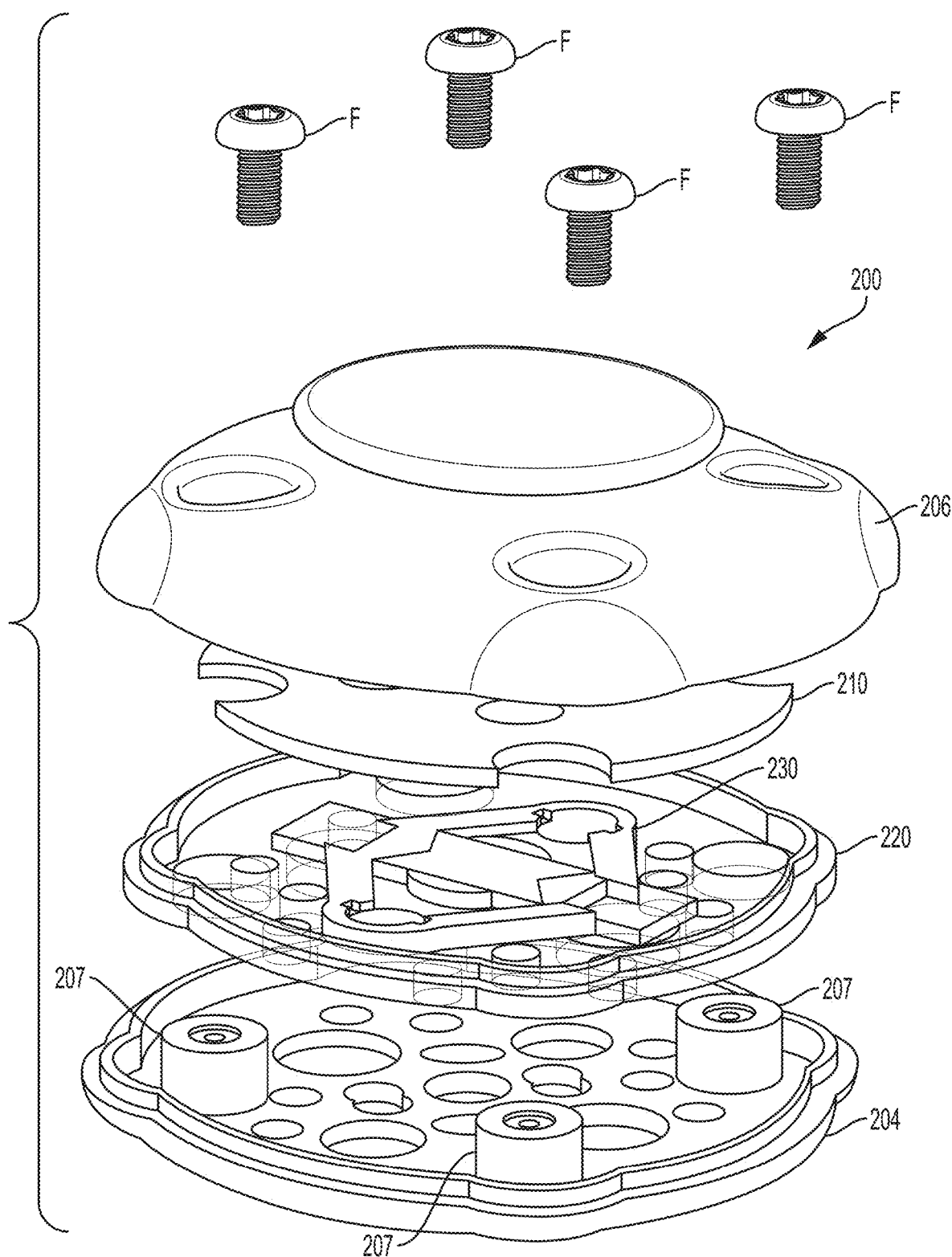
FIGS. 8A-8B are exploded views of an internal optomechanical biometric sensor module, according to some embodiments of the present invention.
Figure 8B:
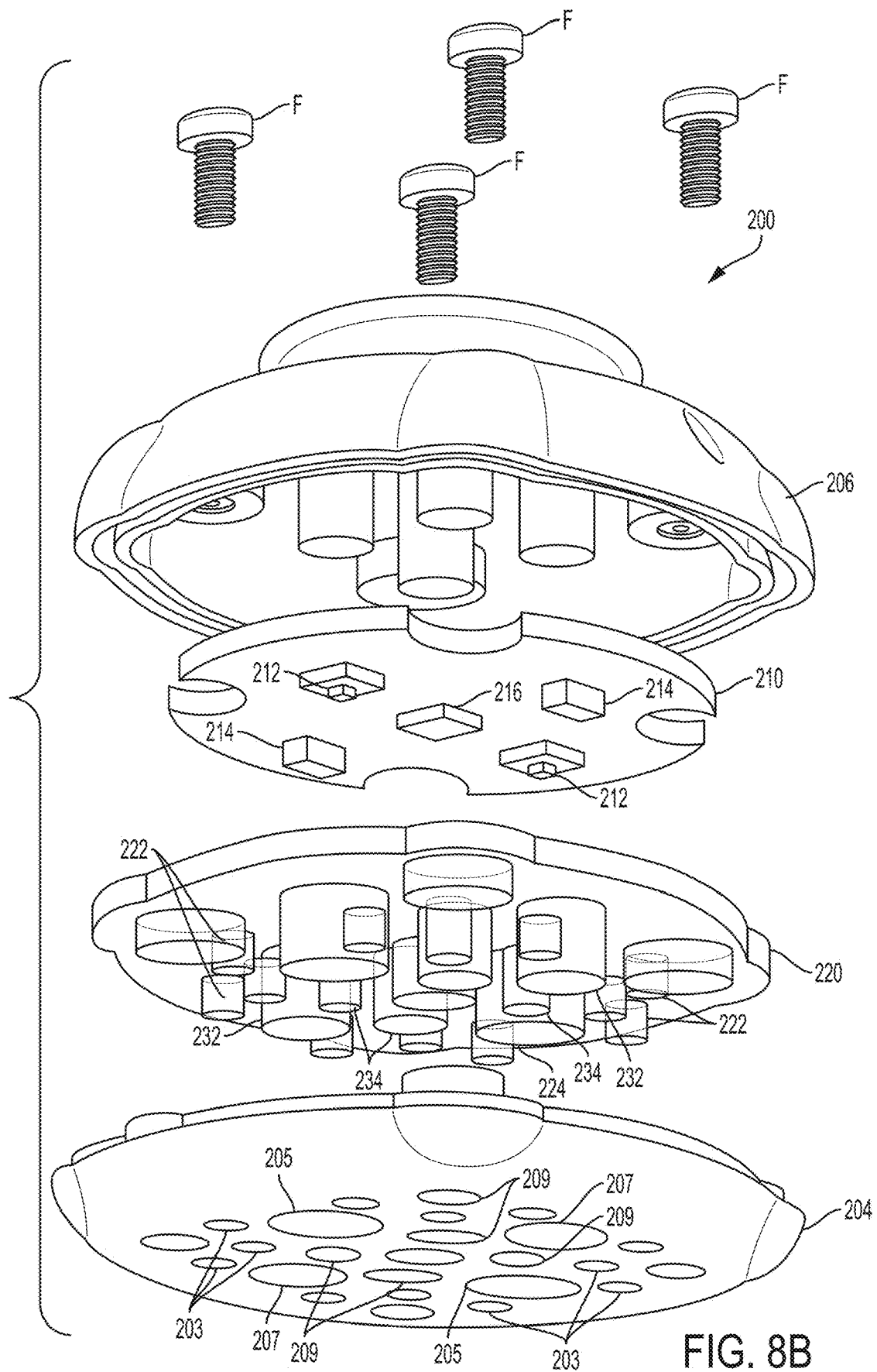
Figure 9A:
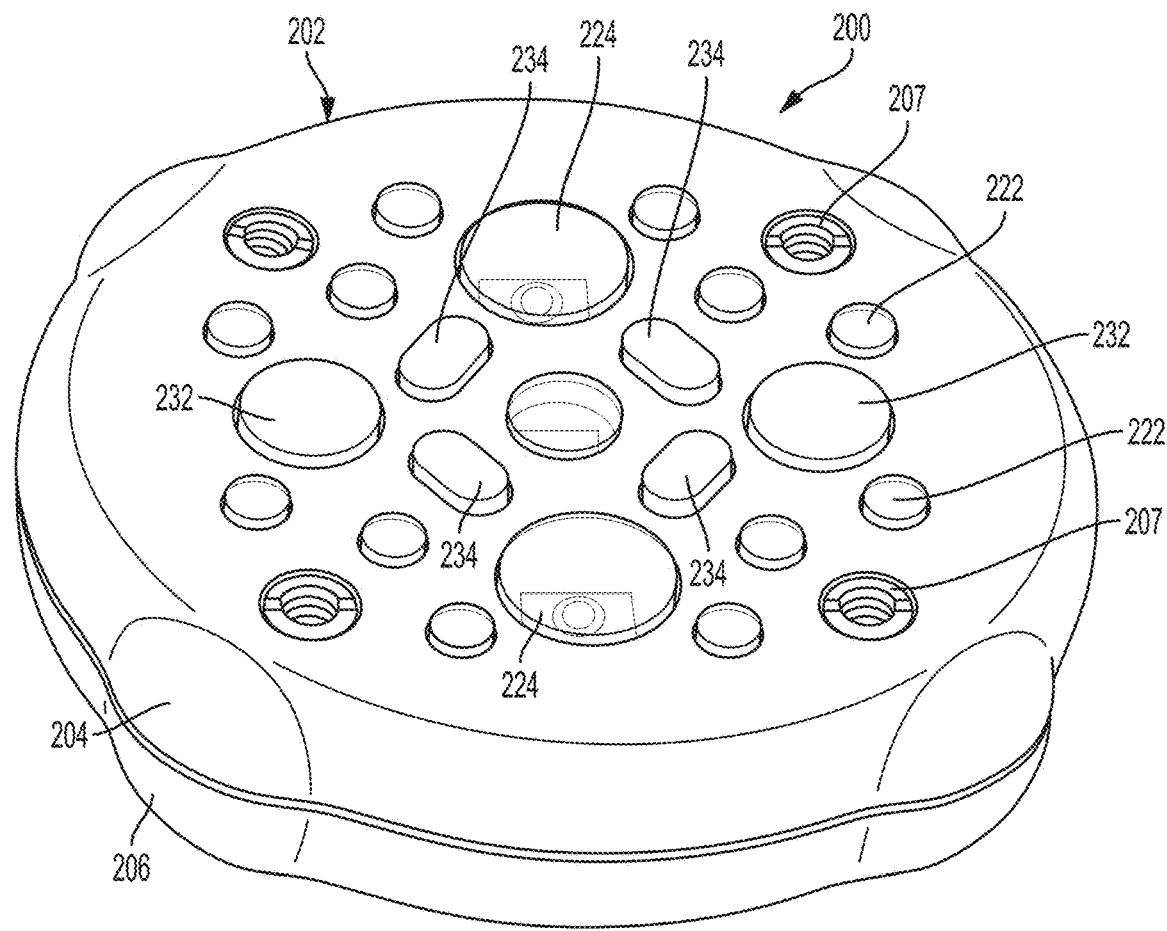
FIG. 9A is a front perspective view of the sensor module of FIGS. 8A-8B in an assembled configuration.

Referring now to FIG. 9A, the sensor module 200 of FIGS. 8A-8B is illustrated in an assembled configuration. The stabilizer members 232, 234 extend through the housing first portion, as illustrated. The stabilizer members 232, 234 interact with the skin of a subject wearing the sensor module 200 and are configured to compress downwardly against the light guide 220 as a result of subject motion and modulate light emitted by optical emitters 214 to produce motion information optical pathways (e.g., 30, FIGS. 1-2) that are detected by the optical detector 216. The stabilizer members 232, 234 are configured to change shape (i.e., collapse) in proportion to relative motion between the skin and the sensor module 200. For example, this relative motion may be caused by force applied upon the stabilizer members 232, 234 by the body of the user. When a stabilizer member 232, 234 collapses, it may modulate light between the optomechanical emitters 214 and the detector 216 in proportion to this relative motion. Thus, whereas the external optomechanical sensor light guides 120, 130 of the sensor module of FIGS. 7A-7D may be made of rigid optically transparent material, so that bending of the optics will not distort the desired reflection profile of scattered light, in contrast, the internal optomechanical sensor module 200 utilizes stabilizer members 232, 234 that are made of material that is at least partially compliant (pliable) upon a pressure between the sensor module 200 and the skin/body.

Figure 9B:
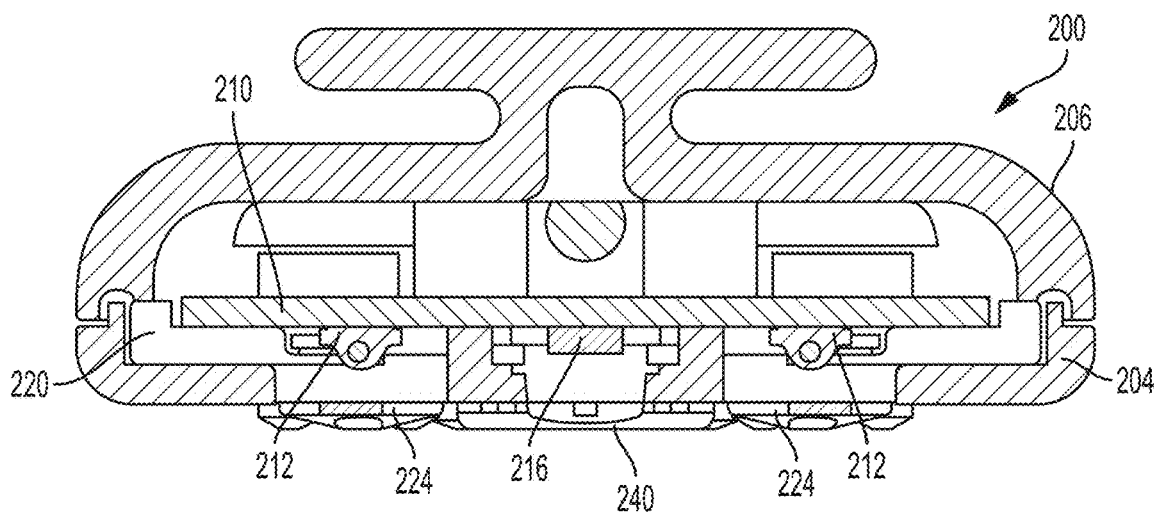
FIG. 9B is a cross-sectional view of the sensor module of FIG. 9A illustrating the biometric information pathways.
Figure 9C:
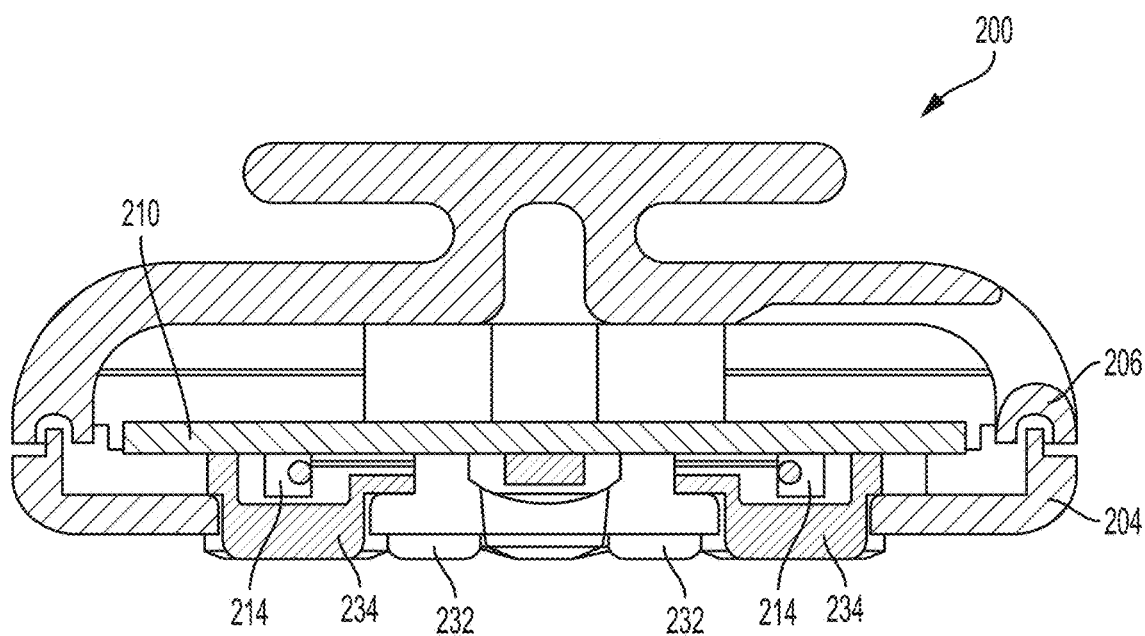
FIG. 9C is a cross-sectional view of the sensor module of FIG. 9A illustrating the motion information pathways.
Figure 9D:
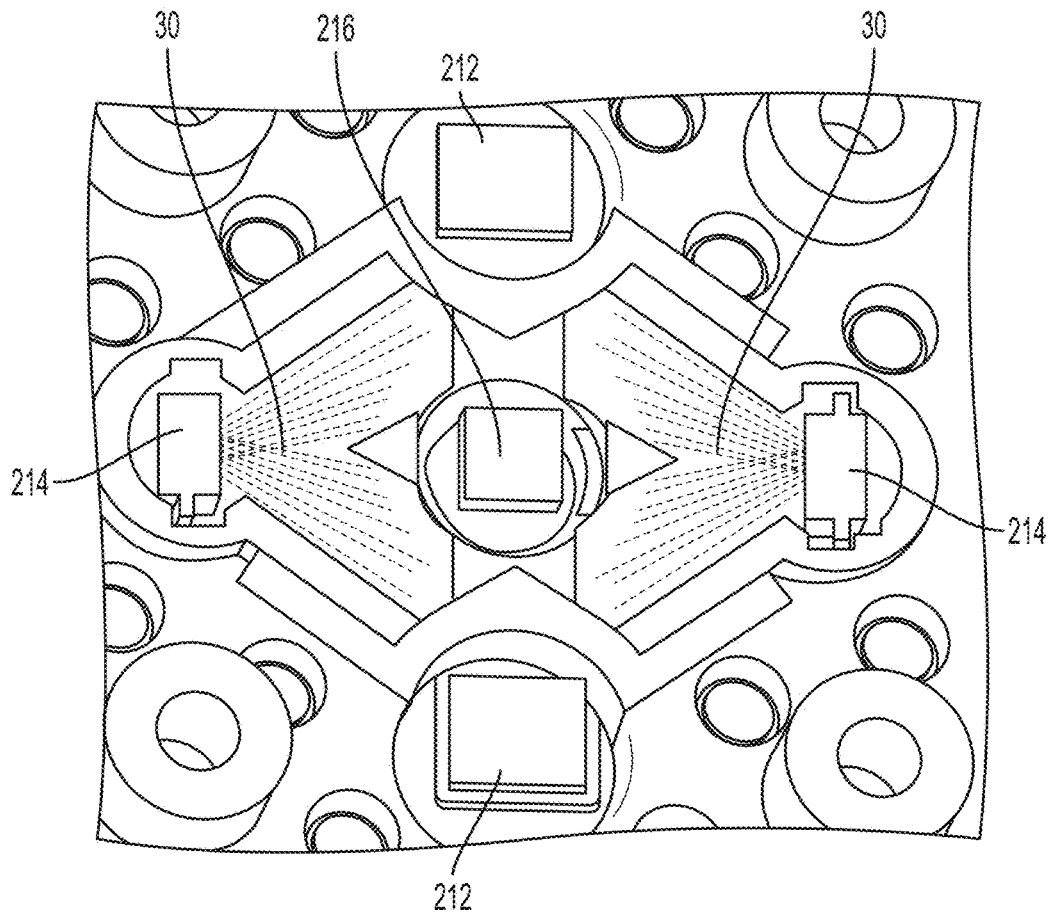
FIG. 9D is an enlarged cross-sectional view of the sensor module of FIG. 9A illustrating the motion information pathways.

FIG. 9B is a cross-sectional view of the sensor module 200 of FIG. 9A and illustrates the configuration of the light guide 220 that creates the biometric information optical pathway that allows light emitted from the optical emitters 212 to enter the body of the subject and then be collected and detected by the detector 216. FIG. 9C is a cross-sectional view of the sensor module 200 of FIG. 9A and that illustrates the configuration of the light guide 220 that creates the motion information optical pathways that allows light emitted from the optical emitters 214 to be modulated by the stabilizer members 232, 234 and then be detected by the detector 216. Motion information pathways 30 produced by the sensor module 200 are illustrated in FIG. 9D.

During relative motion between the sensor module 200 and the body of a subject wearing the sensor module, light scattered via the motion information pathways and light scattered by the biometric information pathways may both comprise motion artifact information. The linearity of motion artifact information from these optical pathways may be at least partially determined by the compliance of the stabilizer members 232, 234 used. Generally, a higher linearity between these pathways may be realized when the compliance of the stabilizer members 232, 234 is close to that of the skin of the subject. This is because light scattered from a biometric information pathway may be scattered mostly by the skin and/or other tissue near the skin of the user, and thus stabilizer members 232, 234 having a mechanical compliance similar with that of skin may also scatter light in a similar manner during motion. It should be noted that although the motion information pathways 30 in FIG. 9D do not contain any light guiding material (e.g., they are filled with air or a vacuum), the motion information pathways may be filled with light guiding material instead.

Moreover, this light-guiding material may also be rigid (such as glass) or compliant (such as silicone).

For the embodiments illustrated in FIGS. 1-6, 7A-7D, 8A-8B and 9A-9D, physical dimensions of housings for these embodiments may be on the order of about 5-20 millimeters, and the physical dimensions of the optical emitter and detector components may be on the order of 0.5-3 mm. However, embodiments of the present invention are not limited to any particular housing size/configuration or optical emitter/detector size/configuration. Numerous size configurations are suitable for embodiments of the present invention. Some size limitations of note are that the ideal spacing between emitters and detectors in a biometric signal pathway may be in between 2 mm and 7 mm. Generally speaking, the farther the emitter-to-detector spacing, the higher the signal-to-noise (AC/DC) ratio. However, if the spacing is too far, the biometric signal will be too weak to be above the noise floor of the photodetector. Also, the sizing of optics in the embodiments of FIGS. 1-6, 7A-7D, 8A-8B and 9A-9D may ideally be larger than a few tens of microns, so that the optics can capture enough light and not overly attenuate signals.

Referring now to FIGS. 10A-10C, an internal optomechanical sensor module (e.g., a PPG sensor module, etc.) 300, according to other embodiments of the present invention, is illustrated. The illustrated sensor module 300 includes a light guide 320 having three separate portions 320*a*, 320*b*, 320*c* separated by optical barriers 330. FIG. 10B is a cross-sectional view of the sensor module 300 of FIG. 10A taken along lines 10B-10B and illustrates the biometric information pathways 40. The light guide 320 is configured to allow light emitted from the optical emitters 312 to enter the body of the subject and then be collected and detected by the detector 316 in order to create biometric information pathways.

FIG. 10C is a cross-sectional view of the sensor module 300 of FIG. 10A taken along lines 10C-10C and illustrates the motion information pathways 30. Stabilizer members 332 are configured to modulate with motion at the sensor module/skin interface. As the interface force increases on a stabilizer member 332, the gap decreases thereby reducing the amount of light reaching the optical detector 316. The modulation of the amount of light reaching the optical detector 316 can be correlated to subject motion and a motion reference signal can be generated via a processor.

Referring now to FIGS. 11A-11D, an internal optomechanical sensor module (e.g., a PPG sensor module, etc.) 400, according to other embodiments of the present invention, is illustrated. The illustrated sensor module 400 includes a base 410, such as a printed circuit board (PCB), supporting a pair of optical emitters 412 and an optical detector 416. The sensor module 400 also includes a compressible/deformable member 420 that contains a plurality of internal light-shuttering channels or pathways 422. In FIG. 11C, there is only a light external pressure on the compressible/deformable member 420 of the sensor module 400. As a result, the light-shuttering pathways 422 remain expanded allowing a maximum amount of light therethrough to the optical detector 416. In FIG. 11D, force on the compressible/deformable member 420 has increased due to subject motion. As a result, the light-shuttering pathways 422 are compressed decreasing the amount of light that can pass therethrough to the optical detector. The modulation of the amount of light reaching the optical detector 416 can be correlated to subject motion and a motion reference signal can be generated via a processor.

Referring now to FIGS. 12A-12C, a biometric sensor module 500 that includes an internal mechanical apparatus (e.g., a pressure transducer) 520 configured to capture motion information from the body of a subject wearing the sensor module 500 is illustrated. The illustrated sensor module 500 includes a base 510, such as a printed circuit board (PCB), supporting a plurality of optical emitters 512 and an optical detector 516. The sensor module 500 also includes a plurality of members 530 extending therefrom that are configured to engage the skin of a subject wearing the sensor module 500. Forces imparted upon the members 530 as a result of subject motion are transferred to the pressure transducer 520 and measured. The modulation of pressure in the pressure sensor can be correlated to subject motion and a motion reference signal can be generated via a processor.

Figure 13A:
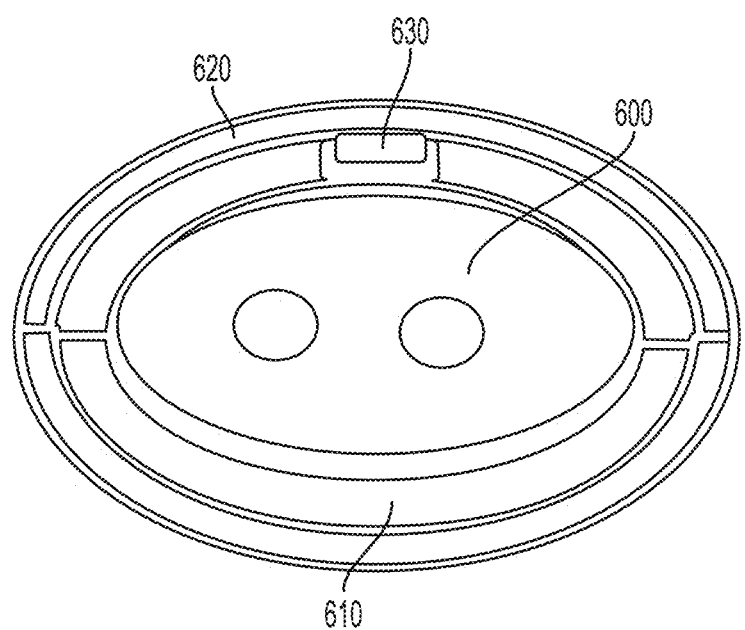
FIG. 13A illustrates a band for a wearable monitoring device having an integrated pressure-sensing bladder, according to some embodiments of the present invention.

Referring now to FIG. 13A, according to other embodiments of the present invention, pressure variation information may be obtained by wrapping a limb 600 of a subject with a fluid filled expansion bladder 610, then constraining the bladder 600 to prevent expansion away from the limb 600 with a band 620 having low or no compliance (i.e., low or no stretchiness). The illustrated band 620 supports a biometric sensor module 630, such as a PPG sensor module. The non-stretchy (i.e., inelastic) band 620 can be incorporated as part of the expansion bladder 610 itself by constructing the bladder 610 from a semi-compliant material. One example of this could be a polyurethane coated nylon material that is RF welded together to form a pouch. This type of a construction will allow some stretch, but will retain a limited shape within the functional pressure range and effectively function as a semi-constrained system. Through this configuration, pressure changes within the limb of a subject wearing the bladder 610 can be directly transferred to the fluid filled pouch.

The fluid within the bladder 610 can be any suitably stable liquid, gas, or gel (water, a water solution, air, silicone, colloid(s), and the like), and pressure transducers (not illustrated) can be employed within the bladder volume to transmit a signal proportional to the change in internal pressure. Exemplary pressure transducers include MEMS (micro-electromechanical systems) devices, diaphragms, actuators, etc. In addition, an optical scatter sensor (such an optomechanical pressure sensor) may be used to sense optical scatter upon motion of the bladder 610 in proportion to changes in pressure.

In order for the bladder 610 to interact with the limb 600 of the subject to pick up pressure readings, it may be necessary for the bladder 610 to interact with the limb 600 by maintaining good surface interaction with the limb 600. Tightening the band 620 around the bladder 610 of fixed volume can force the bladder 610 to interact with the limb 600 and experience deformation and pressure changes from pressure changes within the limb 600. Without such constraint, the bladder 610 may dislocate outside of the band 620 and parts of the bladder 610 may then not couple well with the limb 600. However, if a rigid or semi-rigid band does not fully surround the bladder 610, a semi-constrained bladder system may also provide good coupling between the limb 600 and the pressure sensitive bladder 610. In such case, it may be necessary to pump or fill gas (manually or automatically) within the bladder 610 to prevent dislocation of the bladder 610 outside of the band 620.

The use of a compliant bladder, such as bladder 610 illustrated in FIG. 13A, can be advantageous because a large surface area can interact with the limb 600 over a large proportion of the surface area of the limb 600. In the illustrated embodiment of FIG. 13A, the bladder encircles the limb 600 and pressure changes relate to compression of the entire cross-sectional area of the limb 600. In this way, a processor associated with the PPG sensor 630 receives information about the pressure changes throughout the entire limb cross-sectional area as the limb 600 can be fully contained within the pressure interrogation area. However, a partial bladder (non circumferential) may also be used such that only part of the limb 600 can interact with the bladder 610. In such case, the bladder 610 may be preferably located near the site of the biometric sensor location, such that the motion noise reference location (the pressure sensing location) and biometric sensing location are in proximity. Additionally, although FIG. 13A is drawn towards a limb (such as an arm, wrist, leg, etc.), embodiments of the present invention may be applied towards digits (fingers and toes) as well as other parts of the body that can support an encircling or partially encircling device.

Figure 13B:
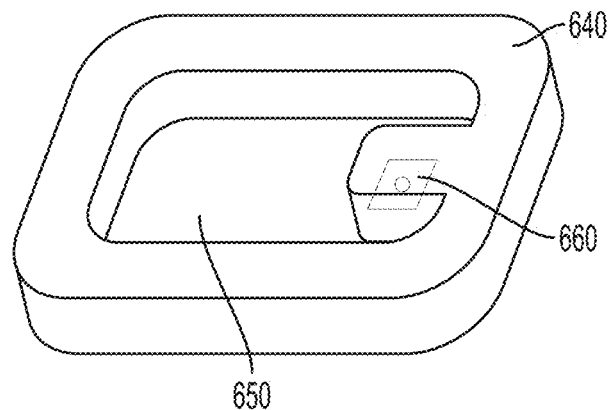
FIG. 13B is a top perspective view of a pressure-sensing bladder for a wearable device, according to some embodiments of the present invention.
Figure 13C:
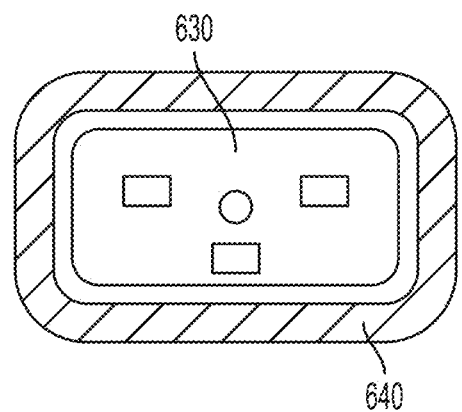
FIG. 13C is a top plan view of the pressure-sensing bladder of FIG. 13B.
Figure 13D:
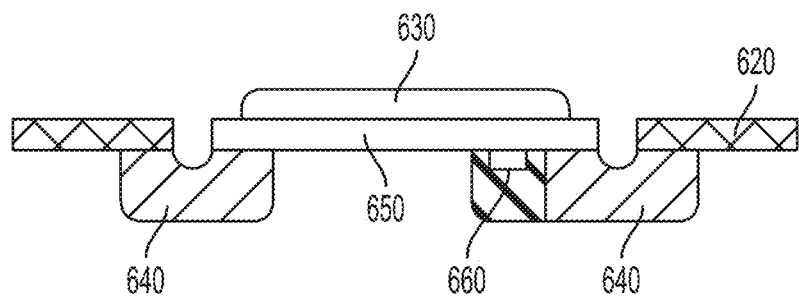
FIG. 13D is a cross section view of the pressure-sensing bladder of FIG. 13B and illustrating the bladder attached to a wristband of a wearable device.
Figure 13E:
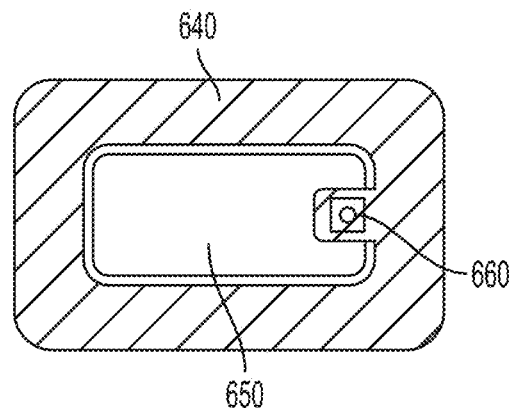
FIG. 13E is a bottom plan view of the pressure-sensing bladder of FIG. 13B.

Referring now to FIGS. 13B-13D, a modular bladder 640 according to embodiments of the present invention is illustrated. A PPG sensor module 630 is positioned on top of a substrate 650 (such as a circuit board or other support structure having electrical connections for powering the sensor module 630), and the substrate 650 may rest on top of the bladder 640. Thus, when integrated into a wearable device (i.e., such as a wearable band 620, FIG. 13D), the bladder 640 experiences a compressive force (i.e., pressure) when the PPG sensor module 630 makes contact with the skin, pushing on the substrate 650 and hence the bladder 640 in contact therewith. A pressure sensor 660 in the bladder 640 detects this pressure so that it can be used as a noise reference, as described below with respect to FIG. 17.

The pressure sensor 660 may be any of a variety of different types of pressure sensors that can be embedded in a wearable sensor module, as described below. In addition, although one pressure sensor 660 is shown, a plurality of pressure sensors may be utilized.

FIGS. 13A-13E illustrate several concepts: 1) reducing pressure and pressure changes on a sensor module, and 2) using the pressure measurement of the bladder fluid as a noise reference of blood occlusion. The changes of pressure of a sensor head, device case, straps, and the like of a wearable device on the skin of a subject tends to modulate the blood's proximity to the surface of the skin by occlusion. More pressure tends to occlude blood away from the surface, while less pressure allows the blood to move back towards the surface. It can be advantageous to reduce and redistribute the total pressure on the face of a sensor head against the skin of a subject. The sensor head can be mounted with a fluid filled bladder to act as a pressure absorber to reduce the pressure between sensor head and the skin. The fluid can be air (or other suitably inert gas), silicone, gel, liquid water (or other suitably inert liquid), or the like. By shaping the bladder 640 of FIGS. 13B-13E as a ring surrounding the sensor head/module 630, the pressure can be redistributed equally across the sensor head/skin contact so as to reduce spots of blood occlusion, especially at the corners or near the optical path of the sensor head.

The bladder 640 also acts to reduce the rate of change of pressure of the sensor head/module 630 against the skin, as happens during vigorous activities or during muscle movements in the area of the sensor head/module 630. The bladder 640 acts to reduce the suddenness of change of pressure of the system. This is advantageous for the sensor signal quality to avoid sudden changes in measurements. A choice of bladder fluid may be made to most effectively balance the pressure reducing effect overall, to most effectively redistribute pressure, or to most effectively reduce pressure changes.

Because PPG sensors are sensitive to changes in blood flow, pressure-related blood flow may be a source of noise on the measured optical signal of the sensor head/module 630 during motion or muscle flexing during a user's activities. For example, flexing muscles may push away blood in such a way that the resulting PPG signal shows the characteristics of a heartbeat pulse wave during muscle flexing, confusing algorithms designed to extract heart rate from the PPG signal.

To allow an algorithm to account for this noise, it can be advantageous to know the pressure of the sensor head/module 630 against the skin so that it may be used as a noise reference. The amount of pressure inside the bladder 640 of FIGS. 13B-13E may be directly related to the amount of pressure between the sensor head/module 630 and the skin. By coupling a pressure sensor 660 to the fluid within the bladder, the measurement can be estimated as a measurement of the pressure of the blood occlusion force. A choice of bladder fluid may be made to closely represent the fluid dynamics of the skin/blood system such that it most closely correlates with the contributing noise, such that noise subtraction results in a cleaner PPG signal more closely related to heartbeat-induced blood flow. For example, in the opto-mechanical configuration of a pressure sensor, where an optical emitter shines light into the fluid and an optical detector detects light scattered from the fluid, wherein the scattered light intensity is proportional to the fluid motion, the desired optical detector signal would closely correlate with the unwanted venous blood motion component (non-pulsatile component) of the blood flow signal captured by the associated PPG sensor.

Figure 13F:
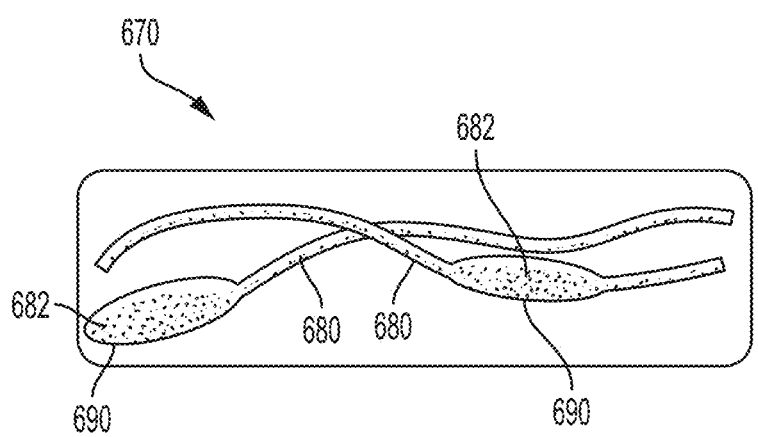
FIG. 13F illustrates a pressure sensing bladder that includes fluid reservoirs and artificial blood vessels in fluid communication with the fluid reservoirs, according to some embodiments of the present invention.

An exemplary configuration of such a representation is presented in FIG. 13F, which illustrates a bladder 670 wherein the fluid-filled region comprises artificial blood vessels 680 at least partially filled with fluid 682. In such a configuration, the bladder may be comprised of compliant (compressible) material, such as plastic, polymer material, silicone, rubber, latex, or the like, such that a compression of the material will result in a skin-like (i.e., human skin-like) compression, pushing the fluid 682 from the artificial fluid reservoirs 690 across the artificial vessels 680. Though the artificial vessels 680 are shown as mostly lateral structures, they may be orientated as mostly vertical structures or other predominate directions, as with real human blood vessels. In one non-limiting embodiment of FIG. 13F, the bladder 670 may be constructed by molding silicone (or other suitable material) around an artificial blood vessel mold. In another non-limiting embodiment, the artificial blood vessels 680 may be fabricated by molding silicone (or other suitable material) without the artificial blood vessel molds in place. Rather, the blood vessel structures may be fabricated by generating intentional bubbles in the silicone. The fluid may be filled within the vessels 680 by soaking the bladder 670 in fluid or exposing the bladder 670 to fluid and sealing up the structure (such as by overmolding or the like) to create a non-leaking unit.

In another embodiment of FIG. 13F, the artificial structure (i.e., the bladder 670) may further comprise microfluidic or nanofluidic circuits and structures to control the fluid flow within the artificial structure. A variety of micro- and nano-fluidic circuits and structures are well-known in the art. It should be noted that the particular embodiment of FIG. 13F can be especially useful as a noise reference for both heart rate monitoring and blood pressure monitoring, as the pressure signal generated may be more indicative of venous blood flow than the other embodiments of FIGS. 13A-13E. Moreover, a further benefit of using the configuration of FIG. 13F as a noise reference is that physical contact of the artificial structure 670 with the skin may not be required, as fluid will flow during motion and be sensed by the pressure (or optical) sensor even without a pressure differential between a wearable device utilizing the artificial structure 670 and the body of the subject.

Referring now to FIGS. 14A-14B, a sensor module 700 having an array of optomechanical motion noise reference sensors 710 (having, for example, one or more of the optomechanical configurations described in the various embodiments of the present invention) for tracking gestural motion is illustrated. The sensor module 700 is attached to the limb of the subject via a band 720. The optomechanical motion sensors 710 are applied in an array along the body (in this case a limb) to sense pressure or to sense motion changes between the array elements and the body of the subject. Thus, as the subject generates gestures, the array elements 710 may sense the pressure generated by these gestures, and these signals may be processed to recognize the gestures. Because the location of the optomechanical sensors with respect to each other is known in advance by their layout in the wearable device, a processor can analyze the sensor readings to map out the muscle-movement-induced pressure readings across the body, converting sensor information into gestural information.

The wearable array may also be in communication with a local accelerometer, and combined accelerometry data plus array data may be processed to determine gross body part motion as well as gestural motion. This functionality may be achieved because the accelerometer may be configured to assess gross acceleration, angular momentum, magnetic location, etc., whereas the array may be configured to sense pressure signals from gestures. It should be noted that in a strictly gestural monitoring system, a biometric sensor is not necessarily needed, but an integrated biometric sensor may also be added to the embodiment in order to provide biometric sensing in addition to gestural sensing.

Head or ear motions or gestures also may be assessed via embodiments of the present invention. One or more optomechanical sensors or sensor arrays 710 may be integrated into an audio earpiece and configured to measure scattered light signals from body motion caused by footsteps, speaking, yawning, chewing, and the like. The output of the optomechanical sensor may then be processed to extract footsteps and mouth motions. Signals associated with mouth motions may be processed to determine what words a subject is speaking or what words someone is "mouthing" (not technically speaking, but generating the mouth motions for a word). These signals may then be used to control a user interface or to be translated into true sounds. For example, by mouthing the word for "turn on", the optomechanical sensor output may be processed (locally or remotely) into a command to turn on a smartphone, the earpiece itself, or some other device.

Figure 15A:
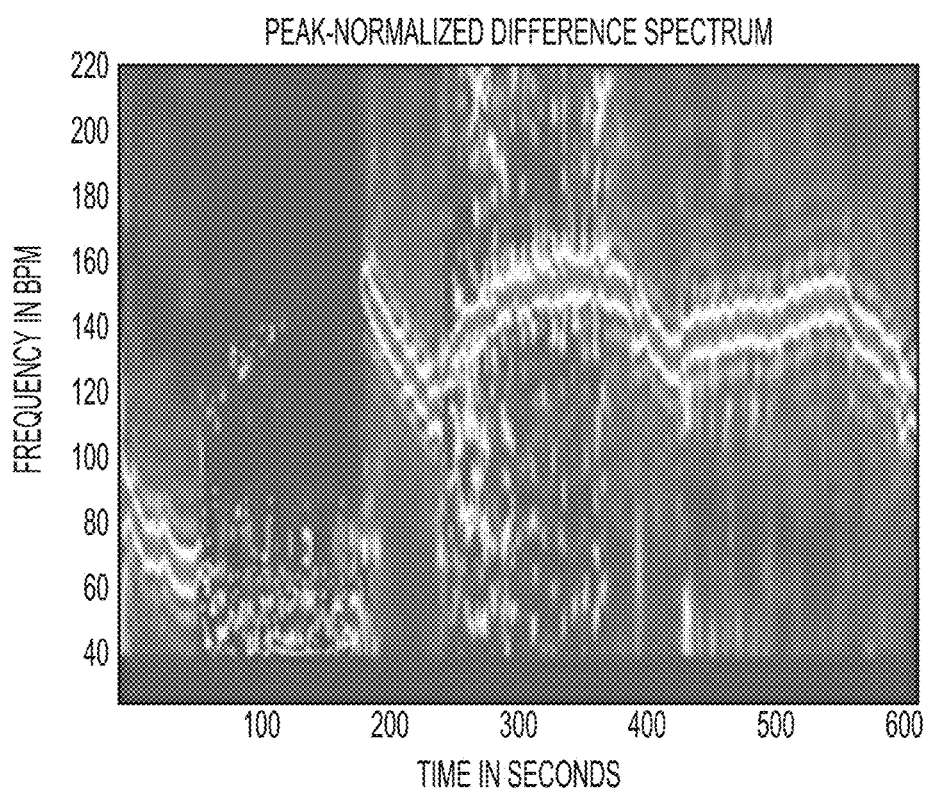
FIGS. 15A-15E are spectrograms of noise reference signals and associated photoplethysmograms.
Figure 15B:
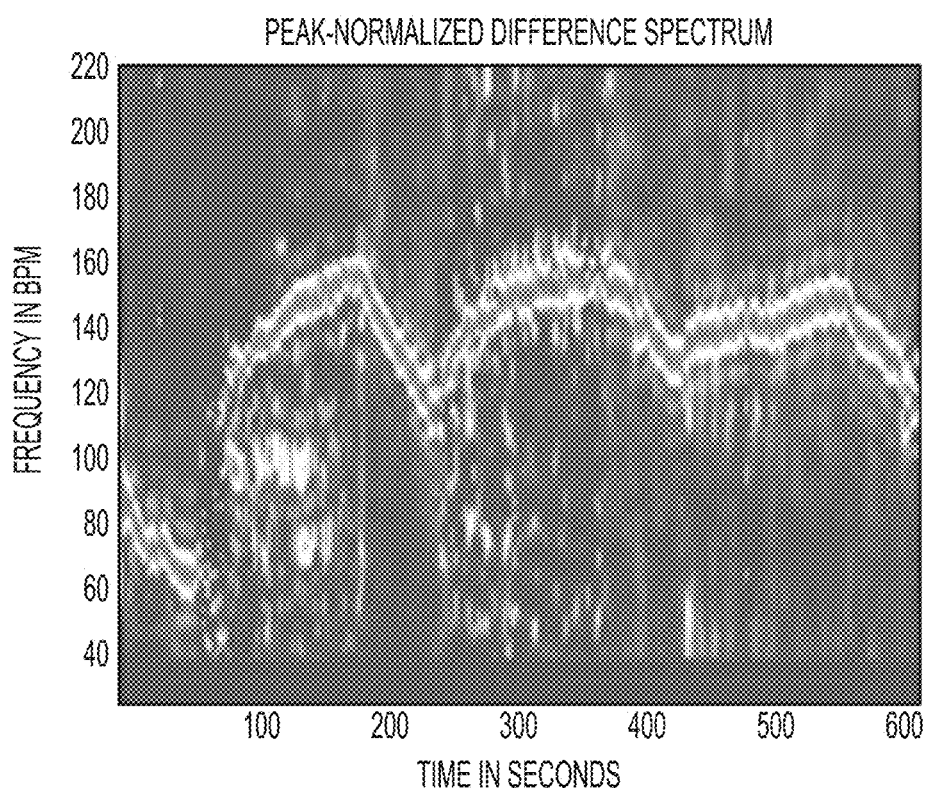
Figure 15C:
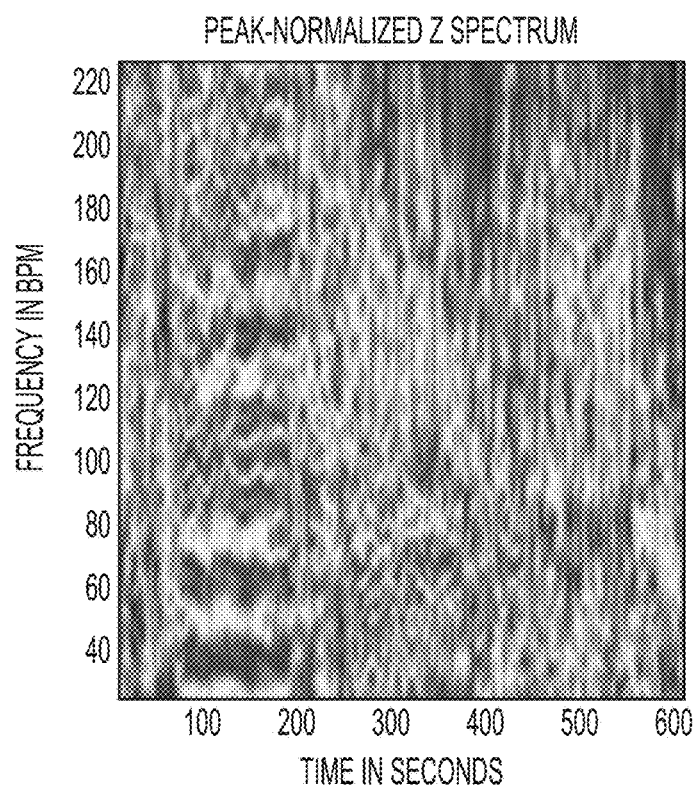
Figure 15D:
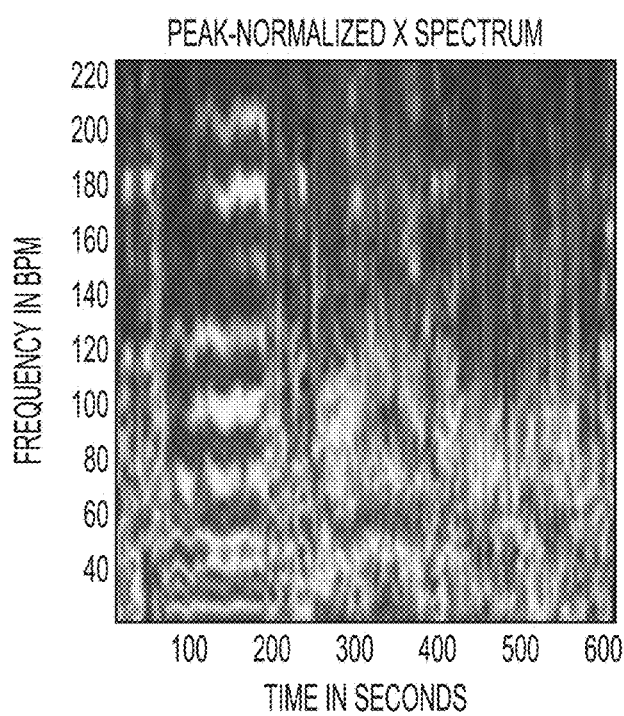
Figure 15E:
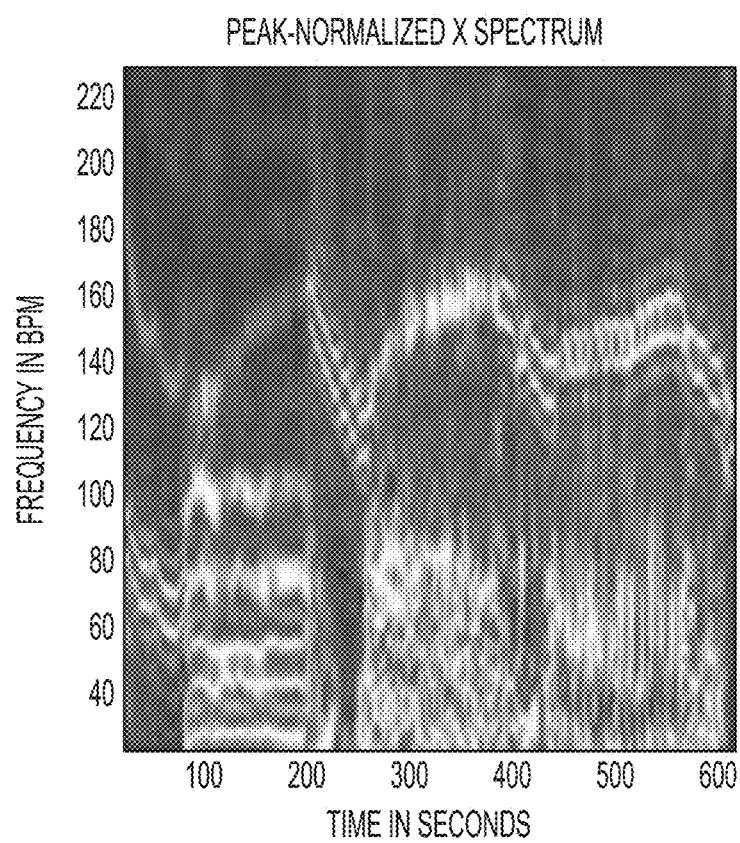

Reference is now made to FIGS. 15A-15E. FIG. 15E is a spectrogram of a raw PPG signal collected from a person wearing a PPG sensor in proximity of the person's skin. FIGS. 15A-15B show normalized spectrograms for a PPG-derived heart rate signal, following active motion-noise cancellation employing embodiments of the present invention and embodiments of co-owned U.S. Patent Application Publication Nos. 2014/0114147, 2015/0018636, and 2015/0011898, which are incorporated herein by reference in their entireties.

A person wearing an armband having a PPG sensor module, according to embodiments of the present invention, was exercising via a strength training technique that involved the following exercises: rowing, inchworms, and thrusters. The PPG armband comprised both an inertial sensor (a 3-axis accelerometer) and an optomechanical sensor (an internal optomechanical sensor). During the PPG signal collection, frequencies associated with motion noise, and harmonics thereof, were actively removed in real-time via spectral subtraction and redaction as described in U.S. Patent Application Publication Nos. 2014/0114147, 2015/0018636, and 2015/0011898.

FIGS. 15A-15B show the PPG spectrograms for this exercise session following active noise removal. However, FIG. 15A shows the spectrogram of the PPG signal where only the accelerometer was used as a noise reference, and FIG. 15B shows the spectrogram of the PPG signal where both the accelerometer and an optomechanical sensor according to embodiments of the present invention were used as a noise reference. Note that for FIG. 15B, the heart rate information is clearly visible in the spectrogram for all exercises. However, in FIG. 15A, the heart rate information for the first part of the exercise, in this case rowing, was not adequately extracted. The origin for this noteworthy difference between FIG. 15A and FIG. 15B may be elucidated by viewing the normalized spectrograms of FIG. 15C, which is the z-axis of the accelerometer and FIG. 15D, which is the optomechanical sensor output. Namely, the spectrogram of optomechanical sensor output of FIG. 15D reflects the noise in the raw PPG spectrogram of FIG. 15E much more closely (as is evinced by the low frequency noise in FIG. 15E).

In contrast, the spectrogram of the accelerometer output does not as closely reflect the noise characteristics of the raw PPG spectrogram. Thus, subtraction of unwanted frequencies is more effective when including the optomechanical information of FIG. 15D, yielding a more accurate representation of user heart rate (FIG. 15B as opposed to FIG. 15A. For noise removal, it is important to note that one may choose to use either the accelerometer signal or the optomechanical signal to determine a user cadence and then use this cadence information to determine harmonics for redaction (i.e., redacting harmonics of running cadence from the PPG signal). But each noise reference may be used for spectral subtraction, either individually or combined.

Figure 16A:
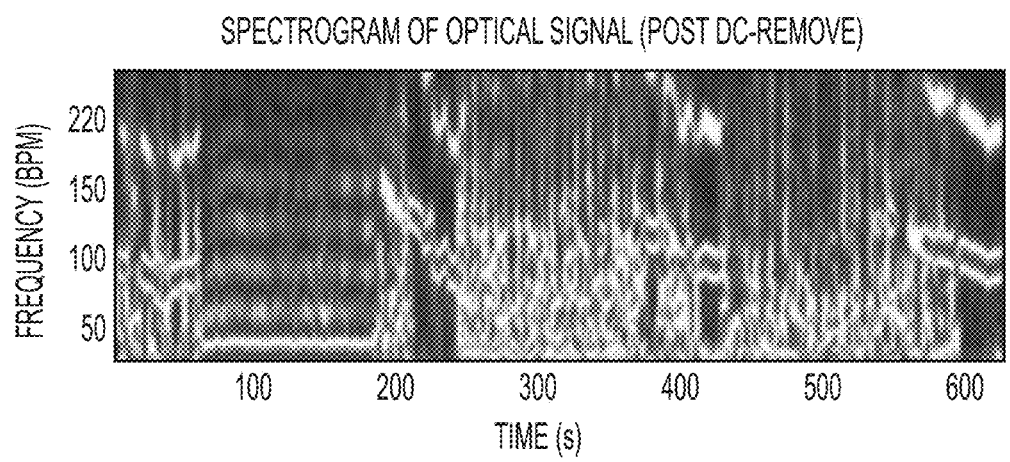
FIGS. 16A-16C are spectrograms illustrating real time noise removal from a PPG signal.
Figure 16B:
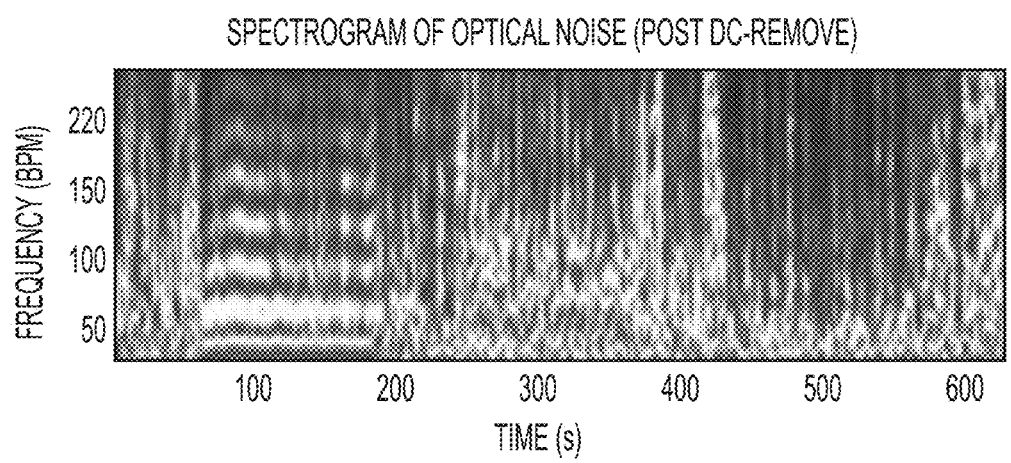
Figure 16C:
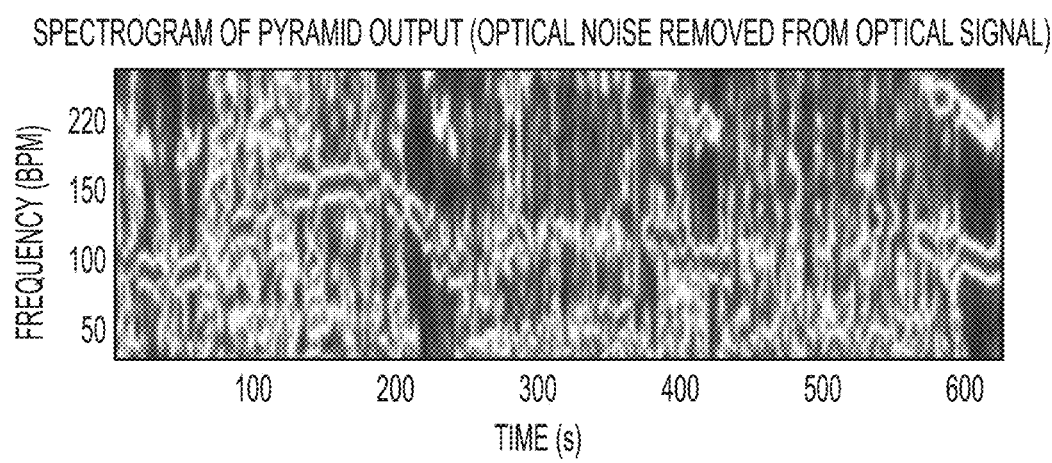

It should be noted that a myriad of noise removal techniques may be applied with the optomechanical pressure signal as a noise reference. For example, the optomechanical signal may serve as the input to an adaptive filter such that the noise reference is actively removed from the raw PPG signal in real time. FIGS. 16A-16C are spectrograms illustrating real time noise removal from a PPG signal. These spectrograms are intensity-normalized in each time slice, and come from the same subject executing a CROSSFIT®-style exercise test over the course of 600 seconds, while the subject was wearing a PPG sensor having an internal optomechanical sensor, as shown in FIGS. 9A-9D. FIG. 16A presents a spectrogram of a PPG signal (the biometric information) following a DC-removal filter. A heart rate signal is barely visible in this spectrogram, and motion noise is apparent. FIG. 16B presents a spectrogram of the associated optomechanical signal (the motion noise reference) following a DC-removal filter. The motion noise is clearly present in the spectrogram. FIG. 16C presents a spectrogram of the output of an adaptive filter (i.e., an LMS or "least-mean-squares" adaptive filter) used to subtract the optomechanical information from the PPG signal information in accordance with embodiments of the present invention (removing the features of FIG. 16B from that of FIG. 16A). Note that the heart rate signal "pops out" from the spectrogram once the motion noise is removed. In particular, the common noise between the optical signal and the optomechanical signal (the noise less than 50 BPM) is removed in FIG. 16C. Also, much of the motion noise between 50 and 80 BPM is removed between 230 and 350 seconds in FIG. 16C.

Figure 17:
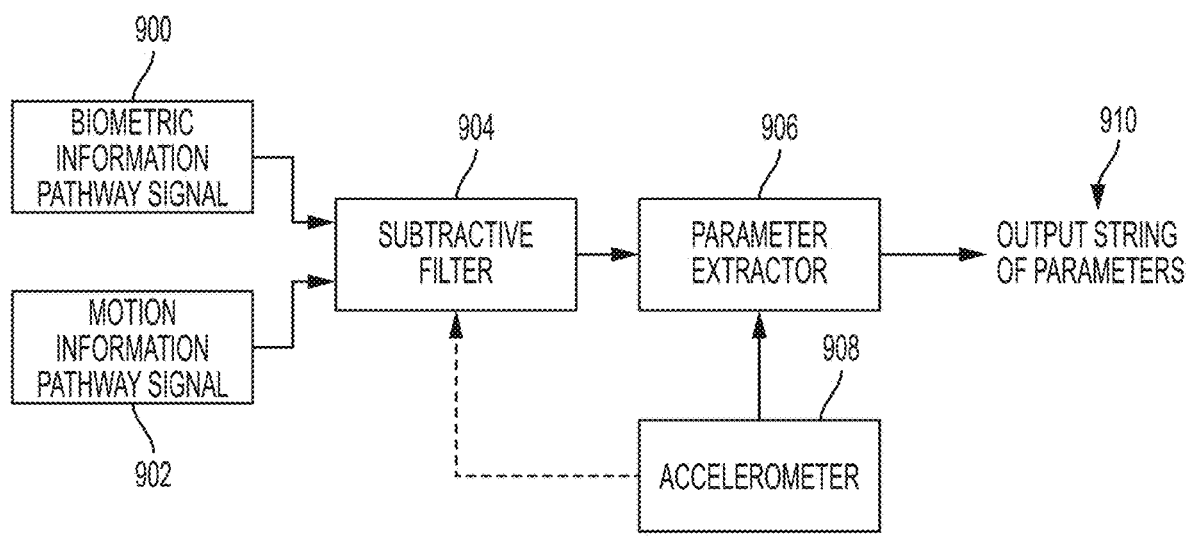
FIG. 17 illustrates an optomechanical sensor module having a subtractive filter and noise reference for removing noise from noisy physiological signals, according to some embodiments of the present invention.

Exemplary adaptive filters are describe in co-owned U.S. Pat. Nos. 8,700,111 and 8,647,270, which are incorporated herein by reference in their entireties. Moreover, as illustrated in FIG. 17, an optomechanical sensor according to embodiments of the present invention may be used first as a noise reference in a subtracting time-domain adaptive filter, effectively removing or subtracting motion noise from a PPG signal to generate a cleaner PPG signal, and then this cleaned-up PPG output may be the input of a parameter extractor using the accelerometer as a noise reference and/or using the accelerometer to determine user cadence and implement heuristics for estimating heart rate, as described in the aforementioned U.S. patents. Optionally, the accelerometer may also be used as a 2nd noise reference in the adaptive filter to further clean up the PPG signal before the output reaches the parameter extraction stage.

In the illustrated embodiment of FIG. 17, signals 900 and 902 from a sensor module according to embodiments of the present invention are input to a subtractive filter 904. Signal 900 is a signal containing primarily physiological information from a subject (i.e., physiological information obtained via a biometric information optical pathway 40), and signal 902 containing primarily subject motion information (i.e., motion information obtained via a biometric information optical pathway 30). The subtractive filter 904 removes motion noise from the biometric signal using the motion information pathway signal as a noise reference, and the cleaned-up biometric signal is input to the parameter extractor 906 which is configured to produce digital data strings including various physiological data.

Combined with the motion pathway information signal 902, the accelerometer 908 associated with the sensor module may be used as an additional noise reference and/or to determine user cadence and implement heuristics for estimating heart rate. For example, as shown in FIG. 17, motion information from both the accelerometer 908 and motion information pathway signal 902 may be subtracted from the biometric information pathway signal 900. Similarly, both the accelerometer 908 and motion information pathway signal 902 may provide motion information to a processor as a basis for redacting harmonics associated with body motion from the biometric pathway signal.

Additionally, the accelerometer 908 signal and the motion information pathway signal 902 may be processed by a processor such that one of these signals filters or modifies the other signal. This can be useful for the case where it is beneficial for the two signals to have similar characteristics (i.e., similar amplitudes, pulse widths, phases, peak frequencies, harmonics, etc.) in the time- or frequency-domain prior to the noise removal step (904, 1002) in actively cleaning up the biometric pathway signal 900. In such case, a step between 1000 and 1002 in FIG. 18 may be configured to "normalize" the intensity of the either the accelerometer 908 or motion pathway signal 902 based on the output of the other.

It should be noted that FIG. 17 should not be considered a limiting method of signal extraction for a clean PPG signal using the motion information pathway signal 902 as a noise reference, but rather an exemplary method. As described earlier, a variety of filtering methodologies may be applied to clean up the biometric information pathway signal 900 using the motion information pathway signal 902 as a noise reference. Moreover, in the embodiment shown in FIG. 17, the subtractive filter 904 may comprise a simple subtraction filter, an adaptive filter, a heuristic filter, or the like. As described earlier, the filter may also comprise a redaction approach to selectively remove signals (such as unwanted frequencies) from the biometric information pathway signal 900 using the motion information pathway signal 902 and/or accelerometer 908 signal as a noise reference. A redaction approach can be especially useful for removing unwanted spectral harmonics of motion noise from the biometric information pathway signal 900.

As described earlier, in some embodiments of FIG. 17, the subtractive filter 904 may further comprise a spectral transform generator such that the subtraction process proceeds in the frequency domain. It should be noted that, in general, the filters used to remove motion noise as described herein may be analog and/or digital in nature, and the subtractive filter 904 may comprise at least one digital algorithm and/or may comprise an analog filter. A static or active analog filter may be used, but an active analog filter may be more beneficial as it may facilitate the active removal of time-dependent motion noise characteristics.

It should also be noted that although heart rate extraction is discussed at length regarding embodiments of the present invention, the invention is not limited to heart rate monitoring. A cleaned-up PPG sensor output may also be processed to extract other parameters, such as RRi, breathing rate, blood pressure, $SpO_2$, blood hydration level, vascular compliance, heart rate variability (HRV), blood analyte levels, mathematical operations on the waveform (such as integrals, derivatives, transforms, and the like), and various other blood-flow-related properties (such as blood flow rate, volume, density, and the like), and these parameters may be processed together (i.e., by a processor in a wearable device) and organized in a data output such as a serial or parallel data stream.

Figure 18:
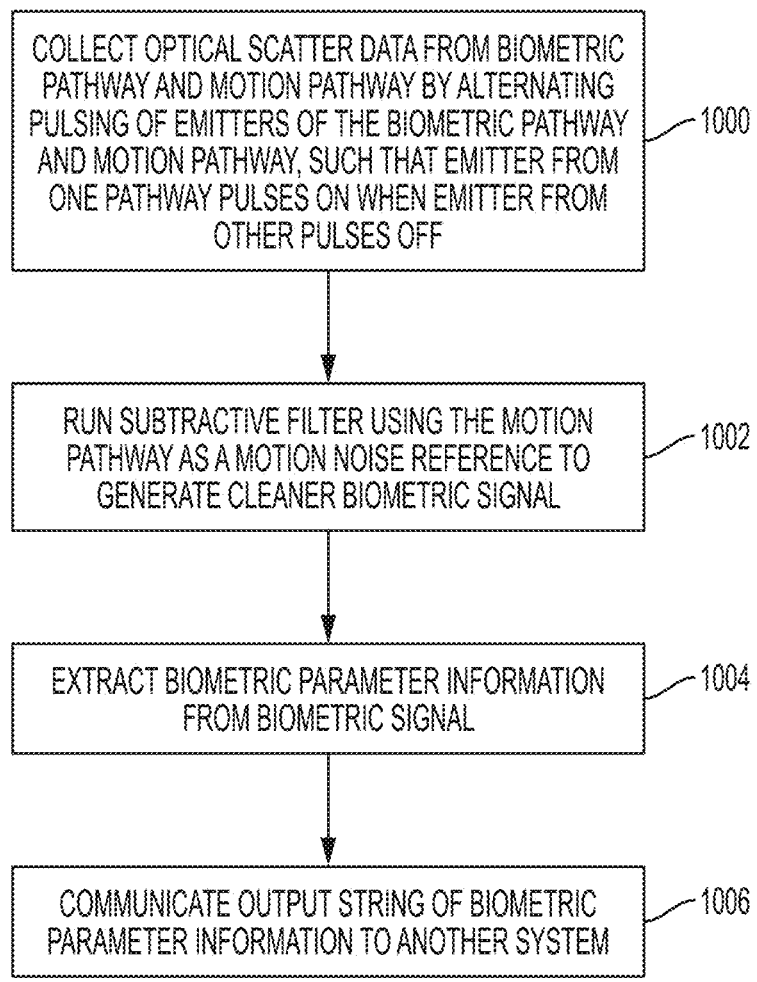
FIG. 18 is a flowchart of operations for utilizing the optomechanical sensor of FIG. 17.

Referring to FIG. 18, an exemplary method of utilizing various embodiments of the optomechanical sensors described herein, perhaps using the system of FIG. 17, is illustrated. Optical scatter data is alternately collected from the biometric information pathway signal 900 and motion information pathway signal 902 by alternating pulsing of the optical emitters associated with the respective pathways (Block 1000). For example, the emitter(s) associated with one pathway may be in a power-on state when emitter(s) from the other pathway is in a power-off state.

A subtractive filter, such as subtractive filter 904, is applied to the collected data using the motion information pathway signal 902 as a motion noise reference to generate a cleaner biometric signal (Block 1002). Biometric parameter information is then extracted from the biometric signal (Block 1004) and communicated to another device or system (Block 1006). It may be beneficial to communicate the extracted biometric parameter information as a serial string of consecutive values representing the biometric values of each extracted biometric parameter. Moreover, it may be beneficial for the serial string to comprise information about the type of biometric parameter and the confidence in the value of the biometric parameter [see U.S. Pat. No. 8,923,941, which is incorporated herein by reference, in its entirety.

Figure 19:
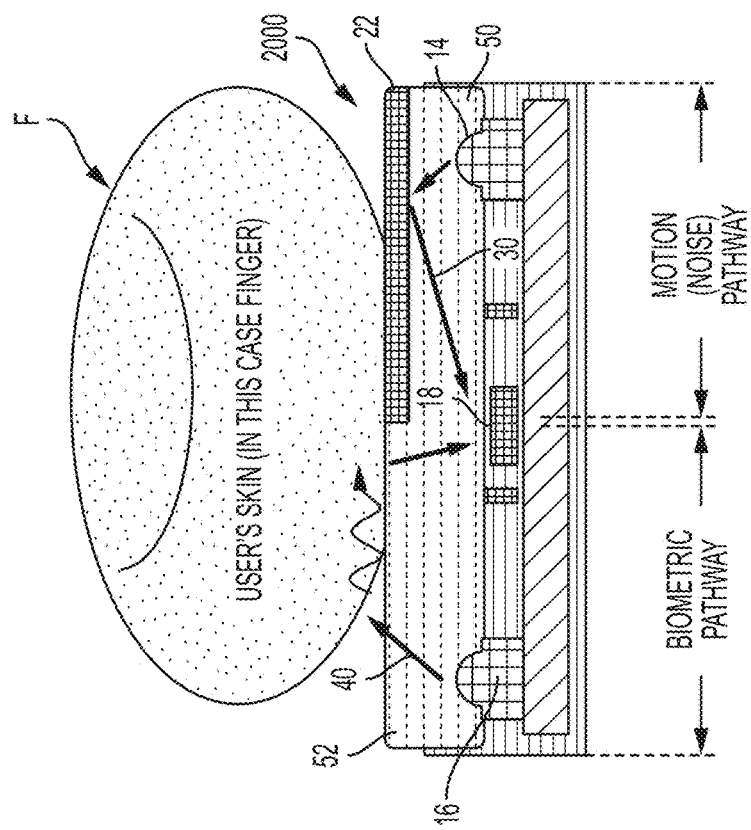

Embodiments of the present invention are not limited to "wearable" embodiments (i.e., embodiments where a sensor module or monitoring device is worn by a subject). Embodiments of the present invention also may be applied in "one-touch" or acute sensing applications. For example, FIG. 19 illustrates a biometric sensor module 2000 for a finger or other digit F. The illustrated sensor module 2000 is an internal optomechanical sensing module having first and second optical emitters 14, 16, and an optical detector 18, as described above. The illustrated sensor module 10 also includes a stabilizer member 22 that is configured to transfer motion information from the finger F of the subject to the optical detector 18 such that when the digit F is pressed upon the biometric sensor module, this motion information (such as that caused by skin displacement, pressure changes, blood displacement, and the like), is transferred to the stabilizer member 22, modulating the light scattered in the motion noise pathway. The illustrated sensor module 2000 produces two optical pathways 30, 40. The first optical pathway 30 (the "motion information pathway") is created by light emitted by the first optical emitter 14 and reflected off of the stabilizer member 22. The second pathway 40 (the "biometric information pathway") is created by light emitted by the second optical emitter 16 that is absorbed, scattered, and/or reflected by tissue, blood vessels, etc., within the finger F of the subject. The biometric information pathway 40 contains a higher level of subject physiological information than the motion information pathway 30, which may contain a higher level of subject motion information than physiological information.

Figure 20:
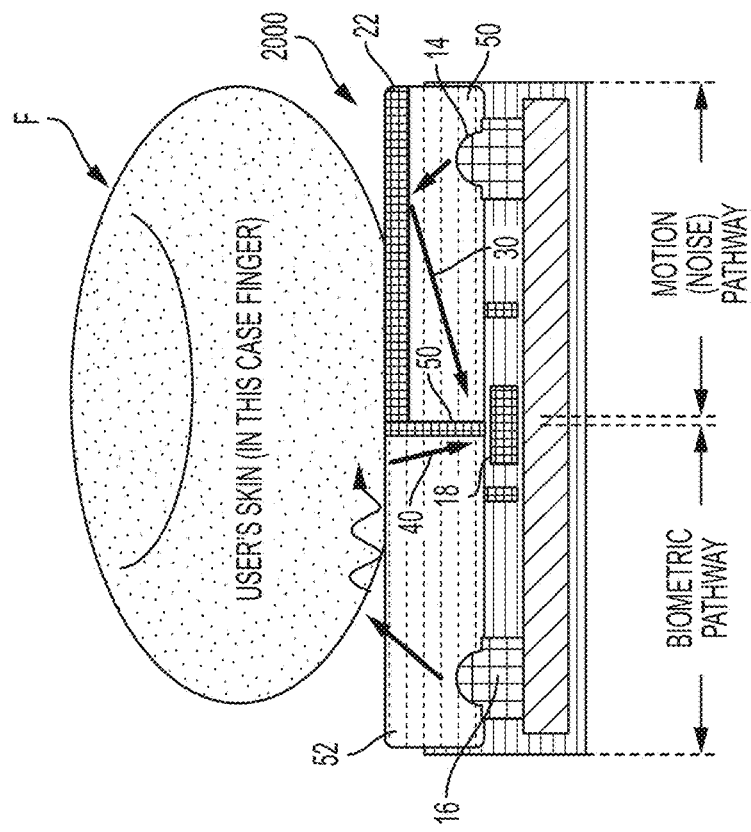
FIGS. 19-20 illustrate "internal" optomechanical biometric sensor modules, and motion information and biometric information pathways generated thereby, for "one-touch" or acute sensing applications, according to some embodiments of the present invention.

The sensor module 2000 of FIG. 20 is similar to the sensor module 2000 of FIG. 19 except that an optical barrier 20 is provided to prevent light emitted by the emitter 14 from being exposed to the user's skin. (Note that in FIG. 19 there may be a small gap where light from the emitter 14 may reach the skin of the user. The barrier 20 in FIG. 20 can prevent this.) This barrier 20 may be critical when using the motion noise pathway signal as a noise reference during biometric parameter extraction (FIGS. 17 and 18), as it is important that the motion noise signal has little or no physiological information that might inadvertently be removed from the biometric pathway signal during the biometric parameter extraction process.

As with other embodiments described herein, the optical detector 18 can be shared or each pathway (i.e., the biometric information pathway and motion information pathway) may have its own detector. Sharing the same detector has the benefit of potentially improving the linearity (in signal amplitude and phase, for example) between unwanted motion noise in the biometric information pathway signal 40 and motion noise detected by the motion information pathway signal 30.

The light guiding region 52 of the biometric information pathway and the light modulating region 50 of the motion information pathway may each include pliable materials, such as optically transparent silicone. The light modulating region 50 is covered with an optically opaque or light scattering stabilizer 22 (such as a light-scattering layer, an opaque silicone, or other opaque and pliable material). In this way, both biometric (PPG) and motion information may be captured by the optical detector 18. However, it should be noted that the function of the motion information pathway is to capture motion information, and this may be achieved with rigid material, as well, e.g., via vibrations in a rigid solid. For example, the light guiding/modulating regions may utilize polycarbonate, glass, or other rigid, optically transparent materials. Alternatively, the light guiding region 52 of the biometric information pathway may be comprised of rigid material and the light modulating region 50 of the motion information pathway may be comprised of pliable material.

The stabilizer(s) may preferably be comprised of pliable material, but it is possible to use rigid material that is sufficiently opaque or another material that can scatter light with body motion. Important aspects of the stabilizer are: a) it must not be optically transparent, as light from the emitter 14 should not reach the skin of the user, and b) it must be able to scatter light proportional to body motion such that moving the digit F against the stabilizer should modulate light scattered in the motion noise pathway.

Although FIGS. 19 and 20 illustrate an internal optomechanical sensor configuration, it should be noted that an acute sensing embodiment may also be achieved using external optomechanical embodiments, such as those illustrated in FIGS. 3-5, 7 as well as the other internal optomechanical embodiments described herein.

Figure 21:
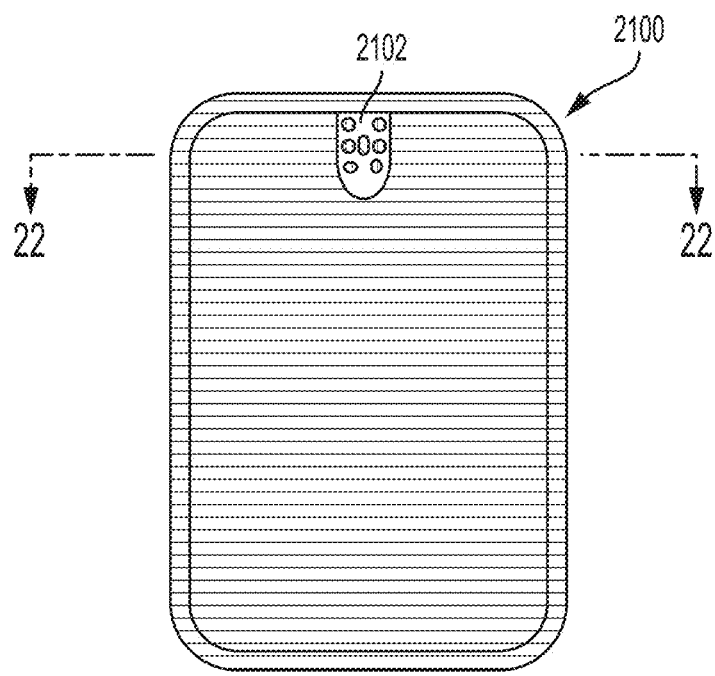
FIG. 21 illustrates an electronic device including a "one-touch" or acute sensing optomechanical sensor module, according to some embodiments of the present invention.
Figure 22:
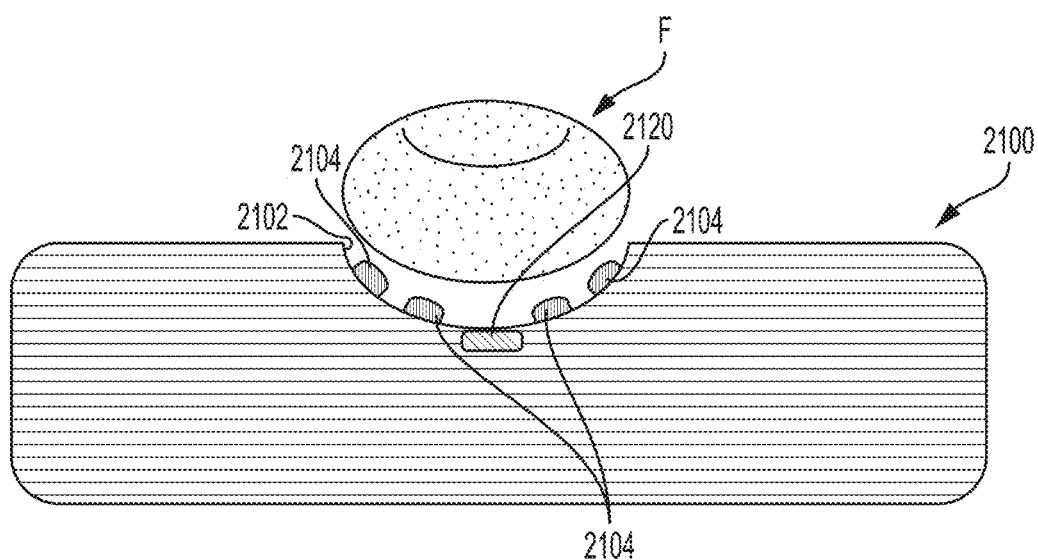
FIG. 22 is a cross-sectional view of the electronic device of FIG. 21, taken along line 22-22.

FIGS. 21 and 22 illustrate an optomechanical sensor configuration as it may be applied to an electronic device 2100, such as a smartphone or other electronic device. The illustrated device 2100 includes a finger-shaped indentation 2102 that is configured to receive a portion of a subject's finger therein. An optomechanical sensor module 2120, such as illustrated in FIGS. 19 and 20, is located within the finger-shaped indentation 2102. The optomechanical sensor module 2120 may be any of the internal or external optomechanical sensor modules described herein.

A plurality of stabilizing elements 2104 are positioned within the finger-shaped indentation 2102 and are configured to support and stabilize a subject's finger F at the location of the optomechanical sensor 2120. These stabilizing elements may be like members 222 in FIG. 9. Namely, they are not meant to transfer motion information (unlike stabilizing members 232 and 234 in FIG. 9), but rather are used for stabilizing (supporting) the sensor at the body.

This illustrated configuration may be particularly useful for one-touch acute sensing of PPG-related biometrics, such as heart rate, respiration rate, blood pressure, hydration level, metabolic rate, cardiac output, blood analyte levels, blood oxygen levels, hemodynamics, and the like. In some embodiments, to enhance blood perfusion during PPG measurements, thereby increasing the signal-to-noise of the PPG waveform information, a vibrational motor within the smartphone 2100 may be engaged to encourage blood flow to the outer layers of the skin of the finger F, perhaps controlled via an algorithm as described below with respect to FIG. 23.

The various optomechanical sensor modules described herein may be combined with a blood flow stimulator to help increase blood perfusion in the area of the body interrogated by optical radiation. A blood flow stimulator may be integrated within a sensor module or an electronic device comprising a sensor module (such as the smartphone 2100 illustrated in FIGS. 21 and 22). A variety of blood flow stimulation methodologies may be implemented, including, but not limited to: thermal, electrical, mechanical, acoustical, and electromagnetic. For example, a heating element for blood flow stimulation may comprise a resistive heating filament, an infrared (IR) heater (also electromagnetic), or the like may be integrated into a sensor module or an electronic device comprising the sensor module. An electrical element for blood flow stimulation may comprise one or more electrode pairs. A mechanical blood flow stimulator may comprise a motor or other mechanical actuator, such as piezoelectric actuator, acoustomechanical actuator, thermomechanical actuator, electroactive actuator, and the like.

In addition, the actuator used within a smartphone to generate haptic feedback may be used to stimulate blood flow, for example, by initiating a vibrational sequence during a PPG measurement process. An acoustical element may comprise an acoustical generator for generating sonic (or ultrasonic) waves that encourage blood flow below the optical interrogation zone of the optomechanical sensor module.

Because many smartphone and other electronic devices include vibrational actuators, no new mechanical hardware may be necessary for blood flow stimulation. An algorithm, such as that shown in FIG. 23, and described below, may be applied to stimulate blood flow, interrogate the skin with light, remove motion noise, and generate a PPG-derived biometric.

In contrast, integrating other types of blood flow stimulators into smartphones and other electronic device may require additional considerations. For example, it may be important for a resistive heating element to be in thermally conductive communication with a skin-interface thermal conductor for coupling thermal energy between the resistive heater and a subject's skin. Similarly, a skin-interface electrical conductor may be important for coupling electrical energy between the embedded electrodes and the skin. Moreover, a thin layer of gold or conductive polymer may be important for preventing corrosion or degradation of such skin-interface conductors. For the case of a radiative IR heater, an IR-transparent optical window (such as sapphire, IR-transparent ceramics, metal fluorides, metal selenides, silicon, germanium, and the like) may be important for coupling thermal energy between the IR heater and the subject's skin.

Figure 23:
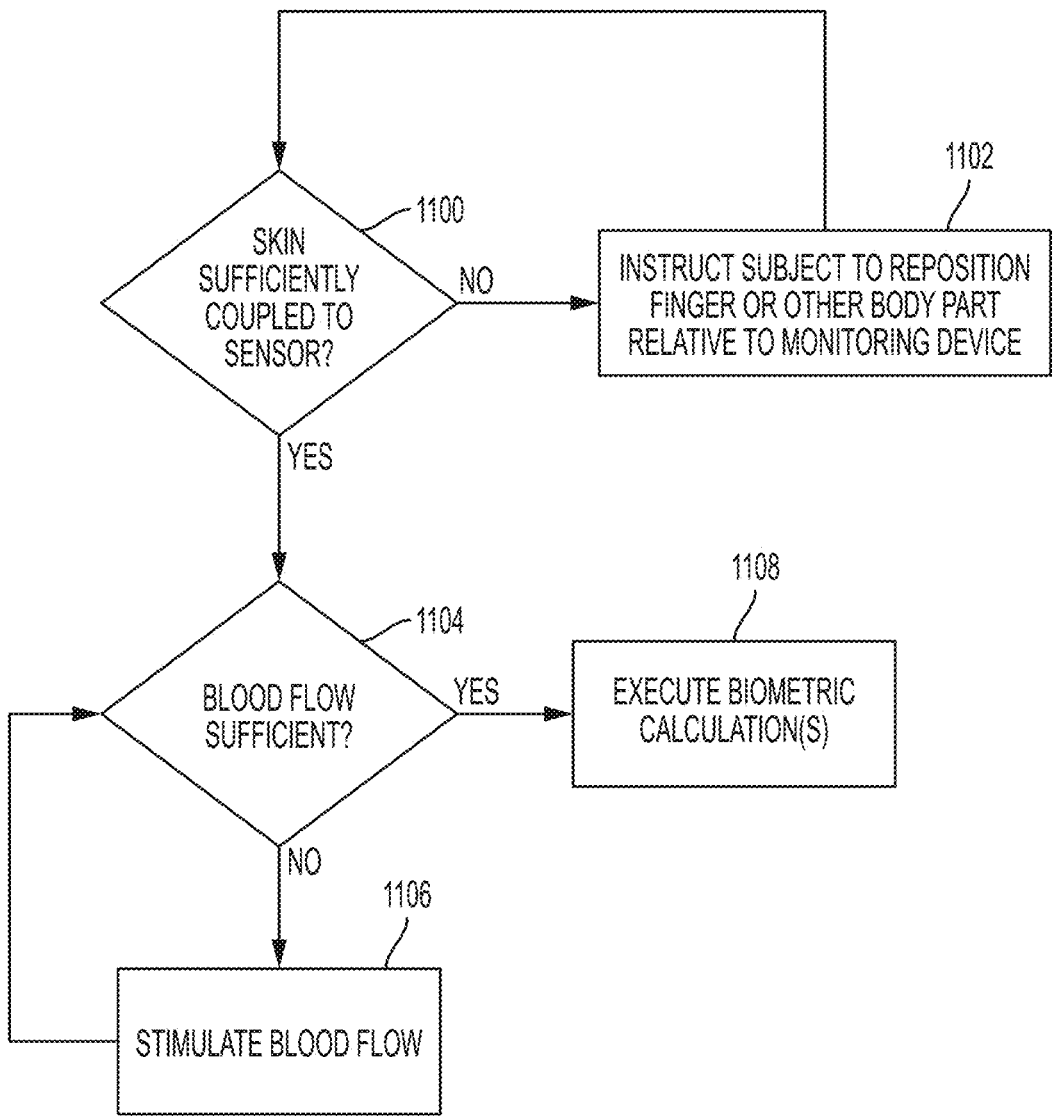
FIG. 23 is a flowchart of operations for implementing blood flow stimulation to improve PPG measurements, according to some embodiments of the present invention.

Referring now to FIG. 23, a method that may be implemented in conjunction with an optomechanical sensor module and blood flow stimulator to improve PPG measurements, according to some embodiments of the present invention, is illustrated. The method may be executed by one or more processors in communication with the sensor outputs from an optomechanical sensor module. For example, in some embodiments, the method of FIG. 23 may be controlled by a processor running a smartphone app.

The illustrated method may start by first determining if a subject's skin is in sufficient proximity to a optomechanical sensor using a proximity detection routine (Block 1100), such as via an optical threshold detection methodology, sensor fusion, or similar proximity detection methods. If the skin is deemed to be sufficiently close to the sensor, then the processor(s) may determine whether the blood flow (perfusion) beneath the user's skin is sufficient (Block 1104), for example, using a signal quality detection methodology. Because the optomechanical sensor is a PPG sensor, this can be achieved by analyzing the quality of the PPG waveform, the signal-to-noise ratio of the PPG signal, blood oxygen level using SpO2 sensing, or the like. Examples of such PPG signal quality methodologies are described in U.S. Provisional Patent Application Ser. No. 62/056,510, the contents of which is incorporated herein by reference in its entirety. Once proximity is confirmed and perfusion is deemed by the algorithm to be sufficient, biometric calculations may then be executed to generate at least one PPG-based biometric (Block 1108). If the perfusion is deemed to be insufficient (Block 1104), then a blood flow stimulator may be engaged to stimulate blood flow and to continue operation until the perfusion is deemed to be sufficient for at least one biometric measurement (Block 1106). Although this example of implementing the method of FIG. 23 is given with respect to integration within a smartphone, the method may be executed via virtually any sufficiently powerful processor and associated circuitry of other electronic devices.

Figure 24:
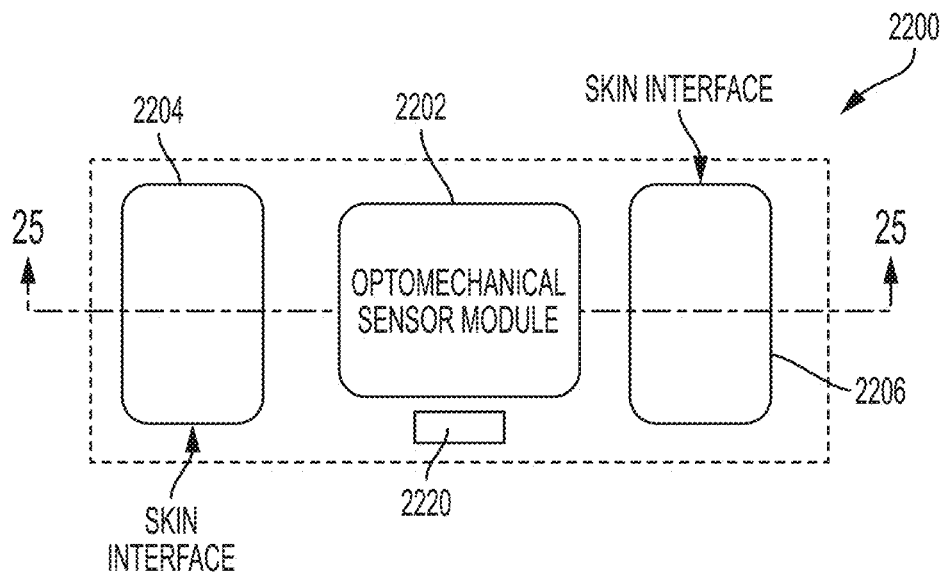
FIG. 24 is a top plan view of a device having an optomechanical sensor module and blood flow stimulators, according to some embodiments of the present invention.
Figure 25:
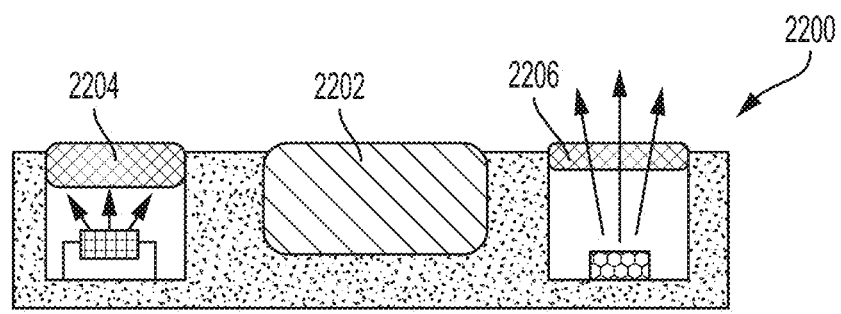
FIG. 25 is a cross-sectional view of an embodiment of the device of FIG. 24, taken along line 25-25.

FIGS. 24 and 25 illustrate the combination of an optomechanical sensor module and blood flow stimulator, according to some embodiments of the present invention. FIG. 24 is a top view of a device 2200, such as a smartphone or other electronic device, in which an optomechanical sensor module 2202 is integrated. The device includes skin interface elements 2204, 2206 which may be electrodes, thermal conductors, acoustic generators, electromagnetic (i.e., IR) radiators, mechanical actuators, or the like, depending on the methodology used to stimulate perfusion (blood flow).

FIG. 25 is a cross-sectional view of the device 2200 of FIG. 24 and illustrates a thermally conductive blood flow stimulator (BFS) 2204 and an IR (radiative) BFS 2206. For the thermally conductive BFS, an air-filled void or other heat conduction medium may be used to conduct heat from the resistive heater to the skin interface thermal conductor. For the case of the IR BFS, a vacuum, an air-filled void, or other IR-transparent medium may be used, since the stimulation energy is radiative and not conductive.

It should be noted that although two blood flow stimulators (2204, 2206) are shown in FIG. 25, it may not be necessary to have both in a device. Rather, these two stimulators are shown to represent how each might be integrated into a device. In some cases, the optomechanical sensor module 2200 may be surrounded by an array of blood flow stimulators of the same type (i.e., all thermal, all IR, all acoustic, all electrical, etc.) or of a plurality of types.

Figure 29:
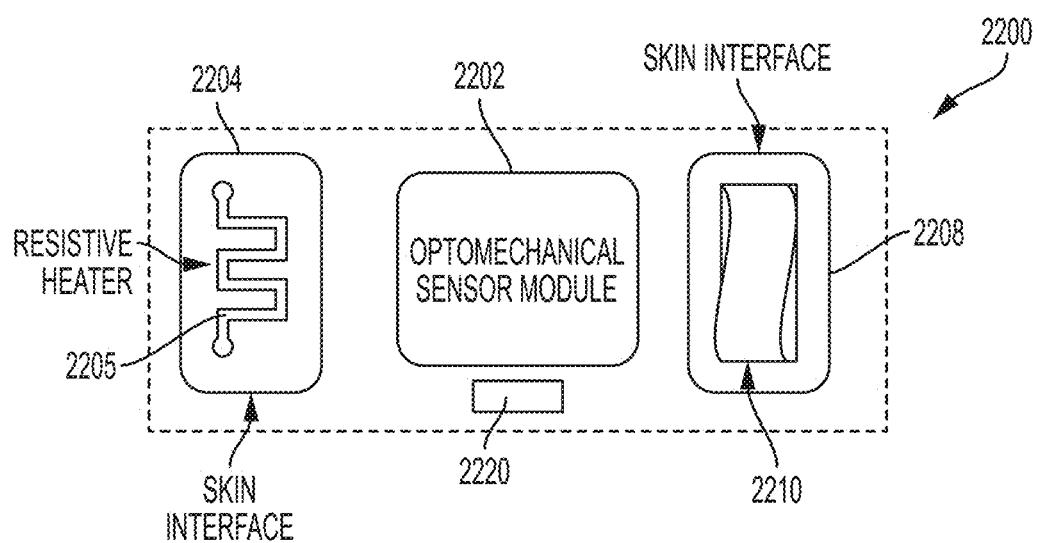
FIG. 29 is a top plan view of a device having an optomechanical sensor module and blood flow stimulators, according to some embodiments of the present invention.

FIG. 29 is a top view of a device 2200, such as a smartphone or other electronic device, in which an optomechanical sensor module 2202 is integrated. The illustrated device 2200 includes a BFS 2204 in the form of a resistive heater having a heating element 2205 is at the surface of the skin interface. A variety of resistive heaters suitable for heating human skin are well known in the art. Also shown in FIG. 29 is a piezoelectric actuator membrane 2210, which may alternatively, or additionally, be used to stimulate blood flow at the area of the body illuminated by the optomechanical sensor module 2202.

Figure 26A:
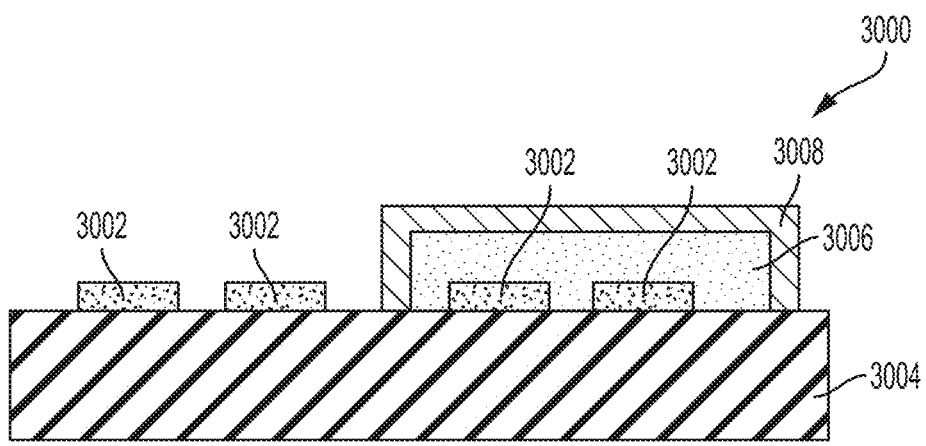
FIGS. 26A-26D illustrate an integrated micro-fabricated optomechanical sensor module and processing steps for fabricating the optomechanical sensor module, according to some embodiments of the present invention.
Figure 26B:
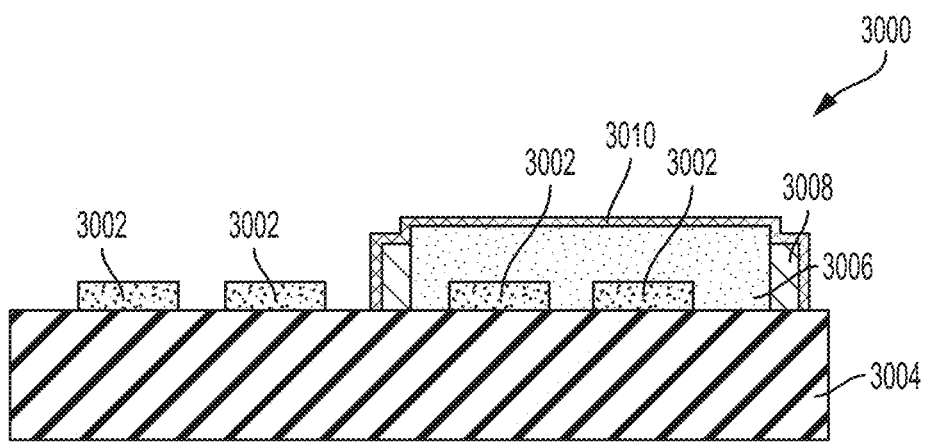
Figure 26C:
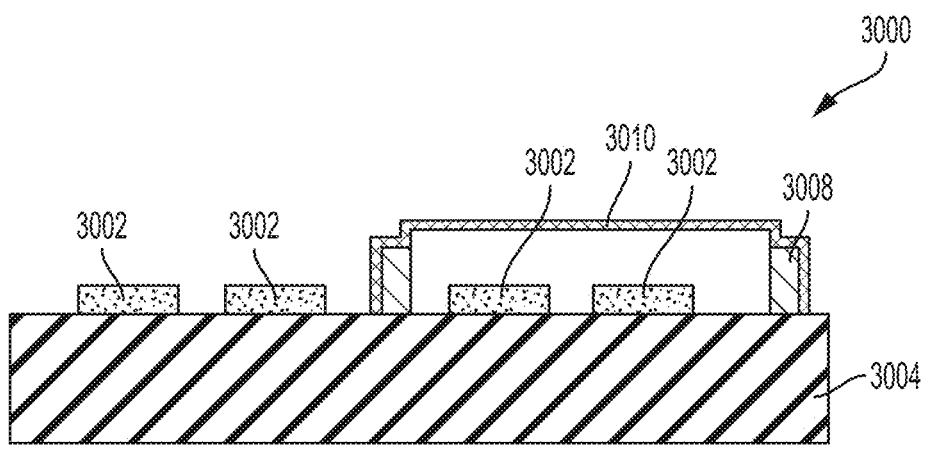
Figure 26D:
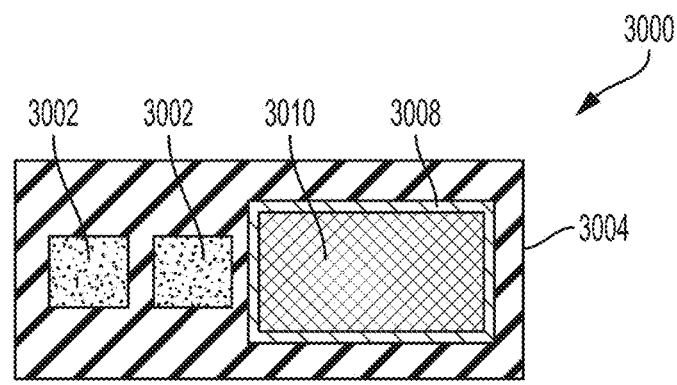

Embodiments of the present invention may include micro- or nano-fabricated devices. For example, FIGS. 26A-26D illustrate an integrated micro-fabricated optomechanical sensor module 3000 fabricated using standard micro-manufacturing processes commonly used to fabricate MEMS devices. FIG. 26A is a side view of the optomechanical sensor module 3000, and FIG. 26D is a top plan view of the optomechanical sensor module 3000. FIGS. 26A-26C illustrate a potential fabrication sequence for generating the module 3000 of FIGS. 26C-26D.

The illustrated optomechanical sensor module 3000 includes four mesa LEDs 3002, two of which are utilized for the biometric signal pathway, and two utilized for the motion (noise) pathway. In the illustrated embodiment, the LEDs 3002 may be comprised of AlxlnyGa1-x-yN, AlxlnyGa1-x-yAs, or other optoelectronic materials, and the substrate 3004 may be sapphire, SiC, AlxlnyGa1-x-yN, AlxlnyGa1-x-yAs, silicon, or other suitable material. In the illustrated embodiment, the LED electrodes are not shown for simplicity, but in principle a suitable layout would be for the electrodes to extend to the periphery of the substrate surface, protected under oxide, and exposed for wirebonding at the periphery. Similarly, opaque barrier regions between the LEDs 3002, which may be useful for preventing direct light contamination from neighboring LEDs 3002, are not shown for simplicity.

The LEDs 3002 may be forward biased to emit light and reverse-biased to detect light. Thus, if at least one LED 3002 in each pathway is forward-biased and at least one other LED 3002 is reverse-biased, then a suitable optical emitter-detector combo may be achieved. Thus, a reverse-biased LED may behave as an optical detector as described herein.

Numerous methods of generating a micro-fabricated optomechanical module 3000, according to embodiments of the present invention may be utilized. For example, once the LEDs 3002 are fabricated, one method is to selectively deposit a sacrificial layer 3006 and a support layer 3008 over the motion pathway LEDs 3002. Then, as shown in FIG. 22B, the support layer 3008 may be etched down a few microns followed by a selective deposition of a membrane layer 3010. An important function of the membrane layer 3010 (analogous to the stabilizer 22 described in FIGS. 19-20) is to move with motion and to scatter light generated by the forward-biased LED 3002 so that the reverse-biased LED 3002 may collect the motion noise information. As shown in FIG. 22C, the sacrificial layer 3006 can then be removed to provide a membrane 3010 over the motion pathway LEDs 3002, supported by the etched-back support layer 3008. A variety of sacrificial layers, support layers, and membrane layers are well known to those skilled in the art and come from a non-limiting list of oxides, nitrides, metals, polymers, and semimetals.

Figure 27:
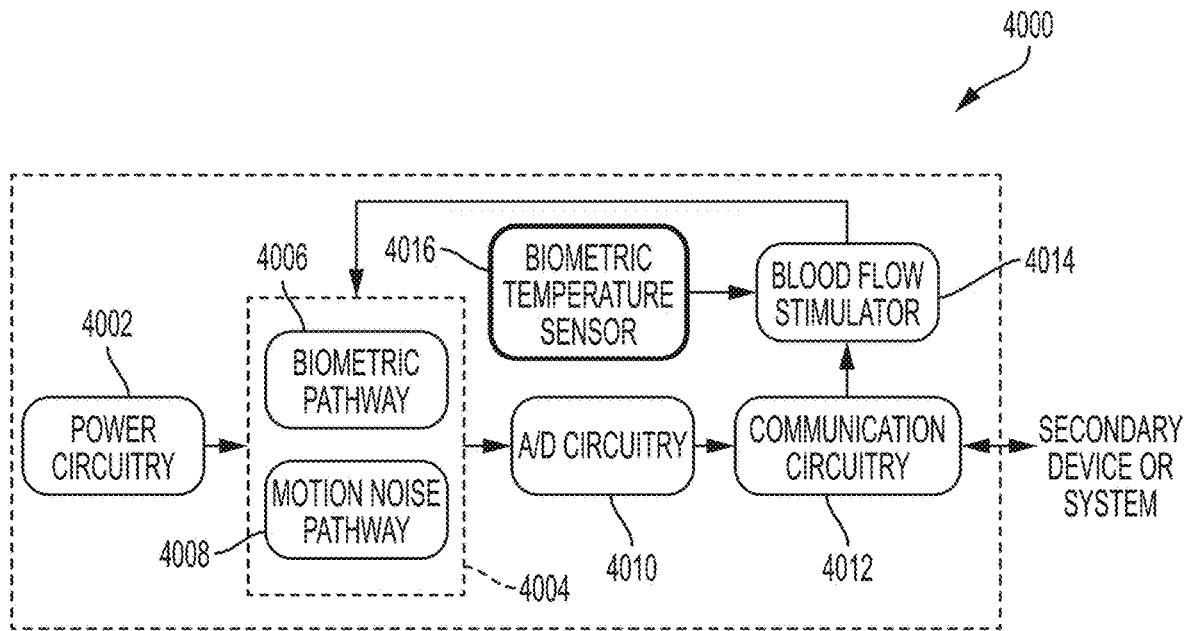
FIG. 27 illustrates a system for generating high-quality PPG data and communicating this data to a secondary device or system, according to some embodiments of the present invention.

FIG. 27 illustrates a system 4000 for generating high-quality PPG data and communicating this data to a secondary device or system, according to some embodiments of the present invention. The illustrated system 4000 can be integrated within a single discrete electronic module or can be distributed throughout, or embedded within, another electronic device (such as the smartphone 2100 shown in FIGS. 21 and 22). The dotted-line around the biometric pathway 4006 and motion noise pathway 4008 is meant to emphasize that these pathways are most likely to be integrated within a discrete module 4004 as described above (e.g., sensor module 2000 of FIGS. 19-20, etc.). One specific embodiment of such a system is illustrated in FIGS. 21-22. For example, the power circuitry 4002, A/D circuitry 4010, blood flow stimulator and associated circuitry 4014, and communication circuitry 4012 may all be part of the existing hardware inside a smartphone, such as smartphone 2100 of FIGS. 21-22. The optomechanical sensor module 4004 is powered by the smartphone circuitry and communicates information with the smartphone circuitry.

However, in another specific embodiment, all of the functional blocks of FIG. 27 may be integrated together in a discrete module, such as a printed electronics circuit board (PCB) with supporting housing, optomechanics, or the like. In some embodiments, a secondary device or system may comprise a remote system or device, and communication between the two systems may occur via standard electrical or wireless protocols.

Figure 28:
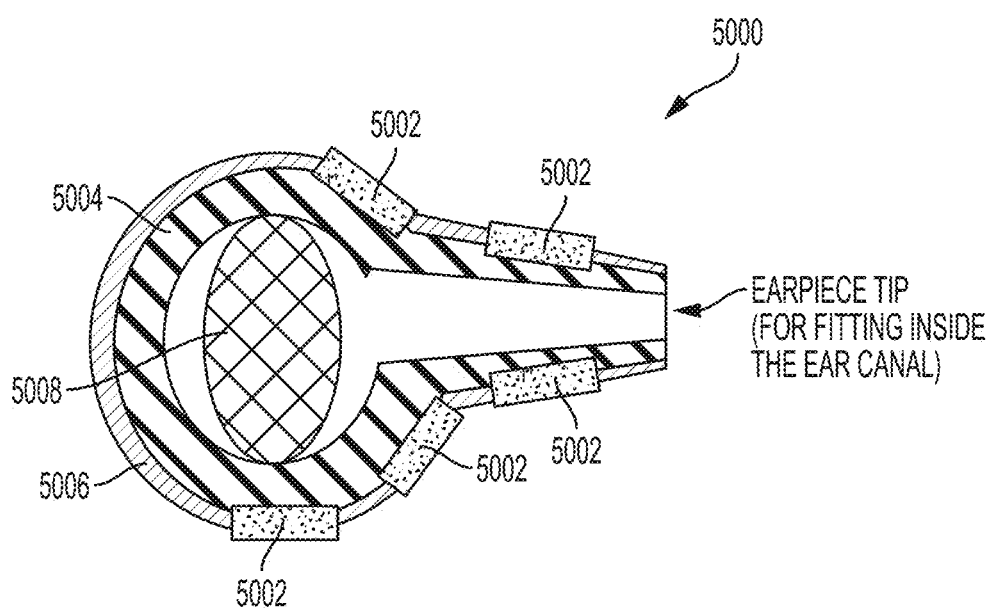
FIG. 28 is a cross-sectional view of an earpiece having multiple optomechanical sensor modules integrated therein, according to some embodiments of the present invention.

FIG. 28 depicts how embodiments of the present invention may be integrated into an earpiece 5000. Though only one optomechanical sensor module may be required for generating clean PPG information, multiple optomechanical sensor modules 5002 are shown at various locations of the earpiece 5000, representing potentially good locations for coupling both physiological and motion information between the ear and the module. The optomechanical sensor modules may be either internal or external optomechanical embodiments, or combinations of both, as described earlier. The illustrated earpiece 5000 includes a housing 5004 surrounded, at least partially, by a cover 5006, and a speaker driver 5008 within the housing 5004.

The combinational stimulation-sensor system of FIGS. 24, 25, and 29, comprising a sensor module 2202 and blood flow stimulator(s) 2204, 2206, 2208, may further comprise at least one biometric temperature sensor 2220, exposed to the skin, to collect thermal data from the illuminated region of the body for estimating the temperature of the skin, blood, or other tissue in proximity to the blood flow stimulator. The biometric temperature sensor 2220 is configured to be proximal to a blood flow stimulator (e.g., 2204, 2206, 2208) and in thermal communication with the skin of the user. Such a sensor 2220 may comprise a biometric temperature sensing element coupled to a skin interface thermal conductor. As a specific example, such a sensor may comprise a temperature-sensing IC (integrated circuit) coupled to an exposed metallic contact (the skin interface thermal conductor), such that the exposed metal contact, when in contact with the skin of the user, transfers thermal energy to the sensing element for generating an electrical signal comprising skin temperature information. Numerous wearable skin temperature sensing configurations are well known to those skilled in the art, and various types of thermal sensing elements—an IC, thermistor, thermocouple, IR sensor, RTD (resistance temperature detector), or the like—may be employed along with various thermal conductors.

In the illustrated system 4000 of FIG. 27, the blood flow stimulator 4014 comprises a thermal generator and biometric temperature sensor 4016 worn proximal to the skin, as described above. The system 4000 may be employed towards temperature-dependent sensing of blood and tissue (i.e., skin, muscle, etc.) which is interrogated by both light from optical emitter(s) of the sensor module 4000 (e.g., sensor module 2202 of FIGS. 24, 25, 29) and thermal energy from skin interface element(s) of one or more blood flow stimulators 4014. In combination with a processor, the system 4000 can be used to actively control stimulation as well as to actively characterize biometric information from the blood or tissue.

The thermal information collected by the biometric temperature sensor 4016 may be processed by a processor to: 1) estimate the temperature of the skin, blood, or tissue that is being illuminated by the optical emitter of a PPG sensor module, and 2) gauge the thermal dosage applied to the skin by the blood flow stimulator 4014, providing feedback for active control of the thermal energy dosage. For example, an algorithm executed by the processor may process the thermal energy information to determine if the dosage is higher or lower than a determined threshold. In such case, the processor may then communicate information to the controlling electronics that the intensity of the blood flow stimulation is to be reduced or increased accordingly. Such a configuration may help prevent burning of the skin while assuring that enough thermal energy is supplied to generate sufficient blood perfusion in the illuminated body region.

Additionally, a stimulation-sensor system+biometric temperature sensor, according to embodiments of the present invention, may also be applied towards temperature-dependent biometric characterization. For example, with supporting analog and/or digital control electronics/circuitry, light generated by an optomechanical sensor module (e.g., sensor module 2202 of FIGS. 24, 25, 29) may be time-synchronized with a thermal blood flow stimulator to execute temperature-dependent biometric analysis of the blood, skin, or tissue via temperature-dependent optical absorption, scattering, polarization, and/or luminescence. Namely, since the interaction between light and biological materials may change with changes in temperature, analyzing the PPG signal from the system 4000 during multiple skin, blood, or tissue temperatures can be used to identify the presence and concentration of skin, blood, and tissue constituents.

As a specific example, the intensity vs. optical wavelength characteristics of biological luminescence of a body region, typically induced by illuminating the body region with optical wavelengths between 200 nm and 490 nm, is known to depend on the temperature of the body region, and this temperature dependence may be different for differing luminescent species. Thus, by controlling the localized body temperature over set ranges and recording luminescence intensity over those set temperature ranges—or even more so by recording optical excitation wavelength-dependent luminescence intensity over those temperature ranges—and then analyzing these wavelength-dependent luminescence intensities in context of biological luminescence models, constituents of the localized excitation region may be characterized.

Figure 30:
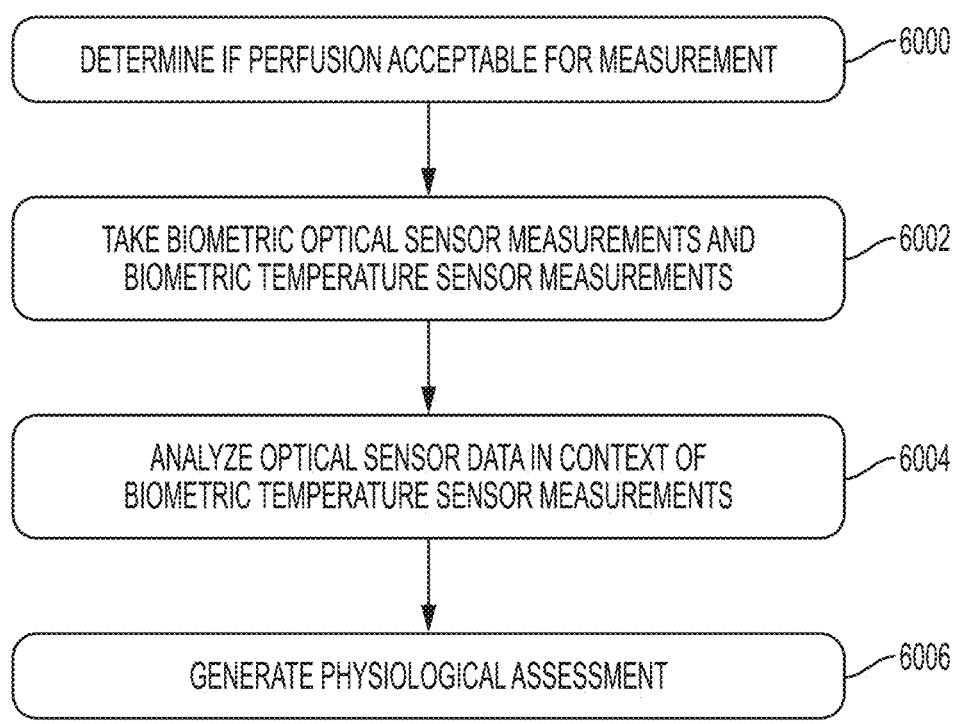
FIGS. 30-32 are flowcharts of operations for generating physiological assessments of a subject, according to some embodiments of the present invention.

Referring to FIG. 30, in one embodiment, the system 4000 of FIG. 27, for example, may be applied towards generating physiological assessments by: 1) first determining if the blood perfusion level is acceptable for measurement (Block 6000), such as via the method described above with respect to FIG. 23, 2) taking measurements of both biometric optical sensor data and biometric temperature sensor data (Block 6002), 3) analyzing the optical sensor data in context of the temperature sensor information (Block 6004), and 4) generating a physiological assessment based on the analysis of this data (Block 6006). This method is particularly well-suited for collecting PPG optical scatter data with changes in the temperature of an illuminated region. Key functional benefits of this methodology include: 1) power savings may be achieved by executing PPG analysis only when the subject's perfusion status is acceptable, and 2) reducing PPG analysis errors (such as PPG-based blood pressure measurement errors, for example) by collecting PPG data only when the subject's perfusion status is acceptable.

Figure 31:
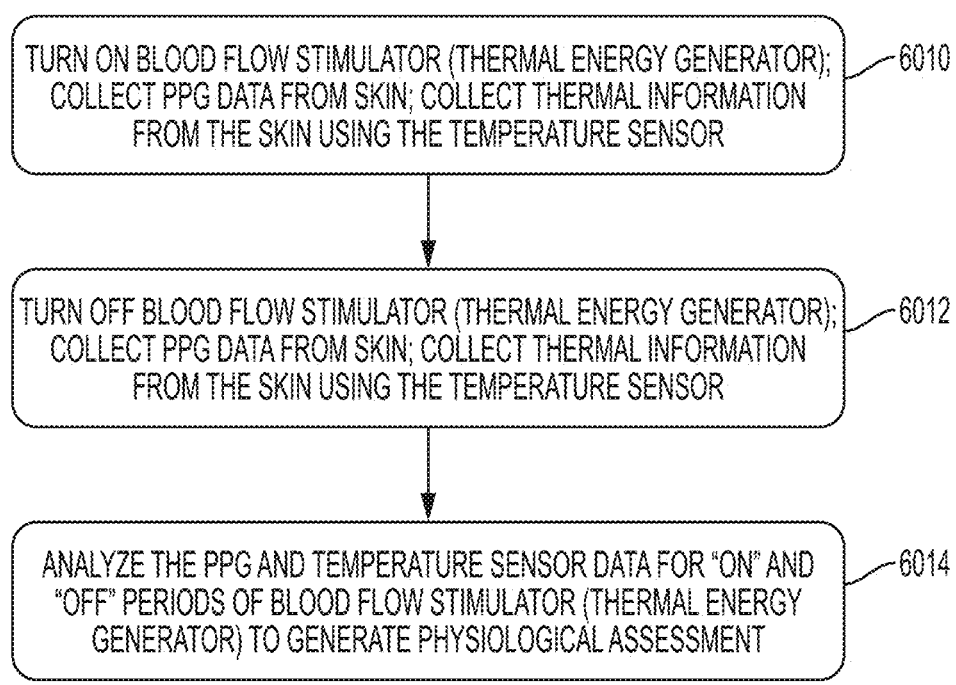

In another embodiment, the temperature control of the body region of interest (the skin and associated blood vessels, blood, etc.) may be more deliberate once viable perfusion status is determined, as shown in FIG. 31. In the method illustrated in FIG. 31, the blood flow stimulator—in this case a thermal energy generator—is turned on and off for certain periods of time; during these periods of time, sensor readings are collected and stored (in memory) from both the biometric optical and temperature sensors (Blocks 6010, 6012). If the PPG sensor module (comprising the optical emitter(s) and detector(s)) is configured to generate light at multiple wavelengths, optical sensor data at each wavelength may be stored for each on/off cycle of thermal energy generation. This may be achieved by cycling through each individual wavelength in time at a set duty cycle or by utilizing an optical detector configured to selectively detect light over a plurality of individual wavelength ranges, as described in U.S. Pat. Nos. 8,251,903 and 8,700,111, the contents of which are incorporated herein by reference in their entireties. The PPG and temperature sensor data is analyzed for "on" and "off" periods of the blood flow stimulator (e.g., a thermal energy generator) to generate a physiological assessment (Block 6014).

As an example of a type of physiological assessment, hemodynamic assessments may be generated by processing the PPG data from both "on" and "off" cycles of the blood flow stimulator (thermal energy generator). As a specific example, the intensity of PPG peaks (i.e., the amplitude of the PPG waveform of one or more blood flow pulses) may be compared for both "on" and "off" cycles, and the ratio of the amplitude of PPG intensity during "on" cycles vs. "off" cycles can be used to assess how sensitive a subject's blood flow dynamics may with respect to ambient temperature or various forms of body temperature.

Figure 32:
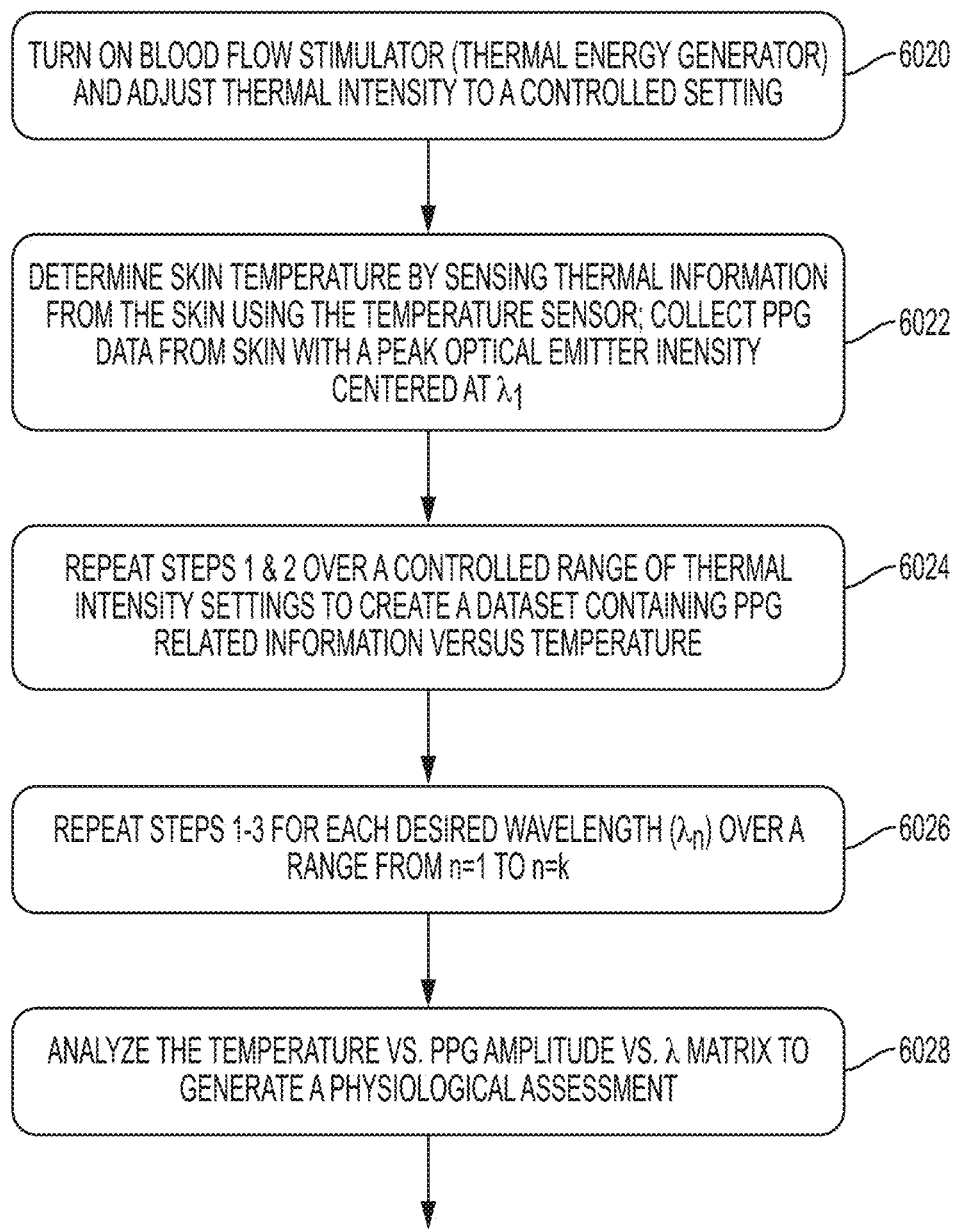

According to another embodiment of the present invention illustrated in FIG. 32, thermal energy generator intensity of a blood flow stimulator may be adjusted to various settings such that a matrix of optical sensor signal intensities over a range of temperatures (and over a range of optical wavelengths if multiwavelength emitters are employed) may be generated. This matrix may then be used to generate physiological assessments based on a biological model.

For example, according to the method illustrated in FIG. 32, a blood flow stimulator (e.g., a thermal energy generator) is turned on and thermal intensity is adjusted to a controlled setting (Block 6020). Skin temperature is determined by sensing thermal information from the skin using the temperature sensor, and collecting PPG data from the skin with a peak optical emitter intensity centered at $\lambda_1$ (Block 6022). The steps of Blocks 6020 and 6022 are repeated over a controlled range of thermal intensity settings to create a dataset containing PPG related information versus temperature (Block 6024). The steps of Blocks 6020, 6022 and 6024 are then repeated for each desired wavelength ($\lambda_n$) over a range from n=1 to n=k (Block 6026). The temperature vs. PPG amplitude vs. $\lambda$ matrix is then analyzed to generate a physiological assessment for the subject (Block 6028).

Figure 33:
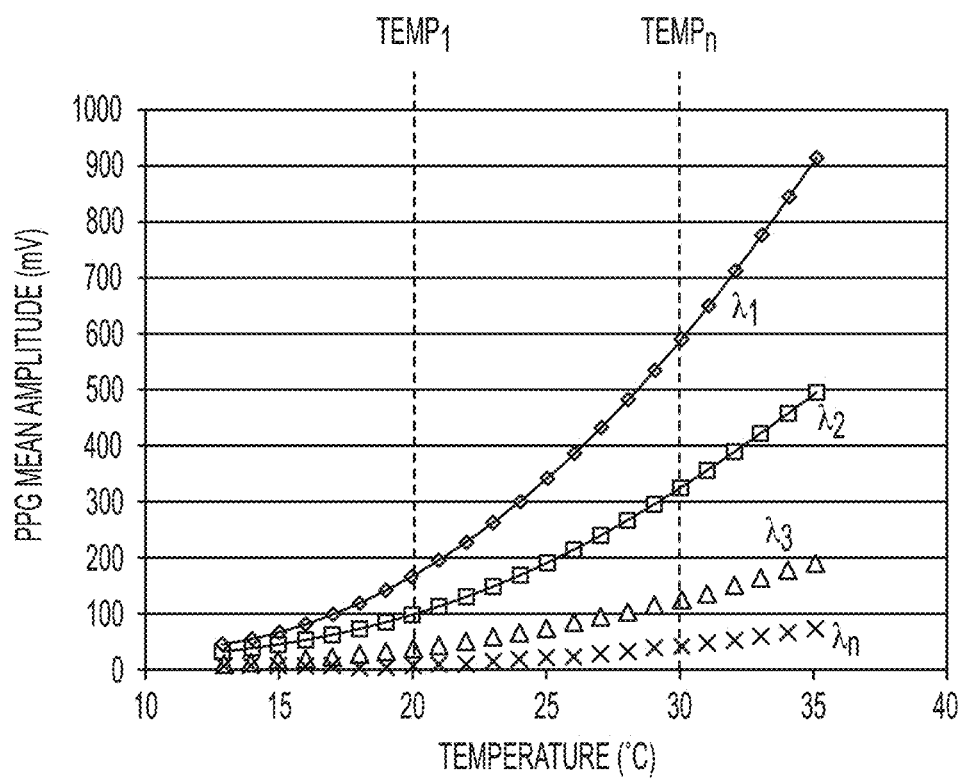
FIG. 33 is a graph of optical scatter (PPG) signal intensity and bioluminescence signal intensity vs. measured skin temperature for multiple optical excitation wavelengths, according to some embodiments of the present invention.

An example of how the method of FIG. 32 may be applied is presented in FIG. 33, showing a plot of optical scatter (PPG) signal intensity & bioluminescence signal intensity vs. measured skin temperature for multiple optical excitation wavelengths ($\lambda_1$, $\lambda_2$, $\lambda_3$, $\lambda_n$) Two exemplary temperatures, $Temp_1$ and $Temp_n$, are presented on the plot, showing how a matrix of optical intensity—optical($Temp_n,\lambda_n$)—may be generated, such that this matrix may be applied towards generating a physiological assessment based on a biological model. Although the collected optical energy detected by an optical sensor may comprise optical scatter or optical luminescence information from multiple blood, skin, or tissue constituents, having optical sensor data from multiple optical wavelengths at multiple temperatures helps provide enough data to characterize "n" constituents with "n" unknowns, as with multi-wavelength pulse oximetry.

Figure 34:
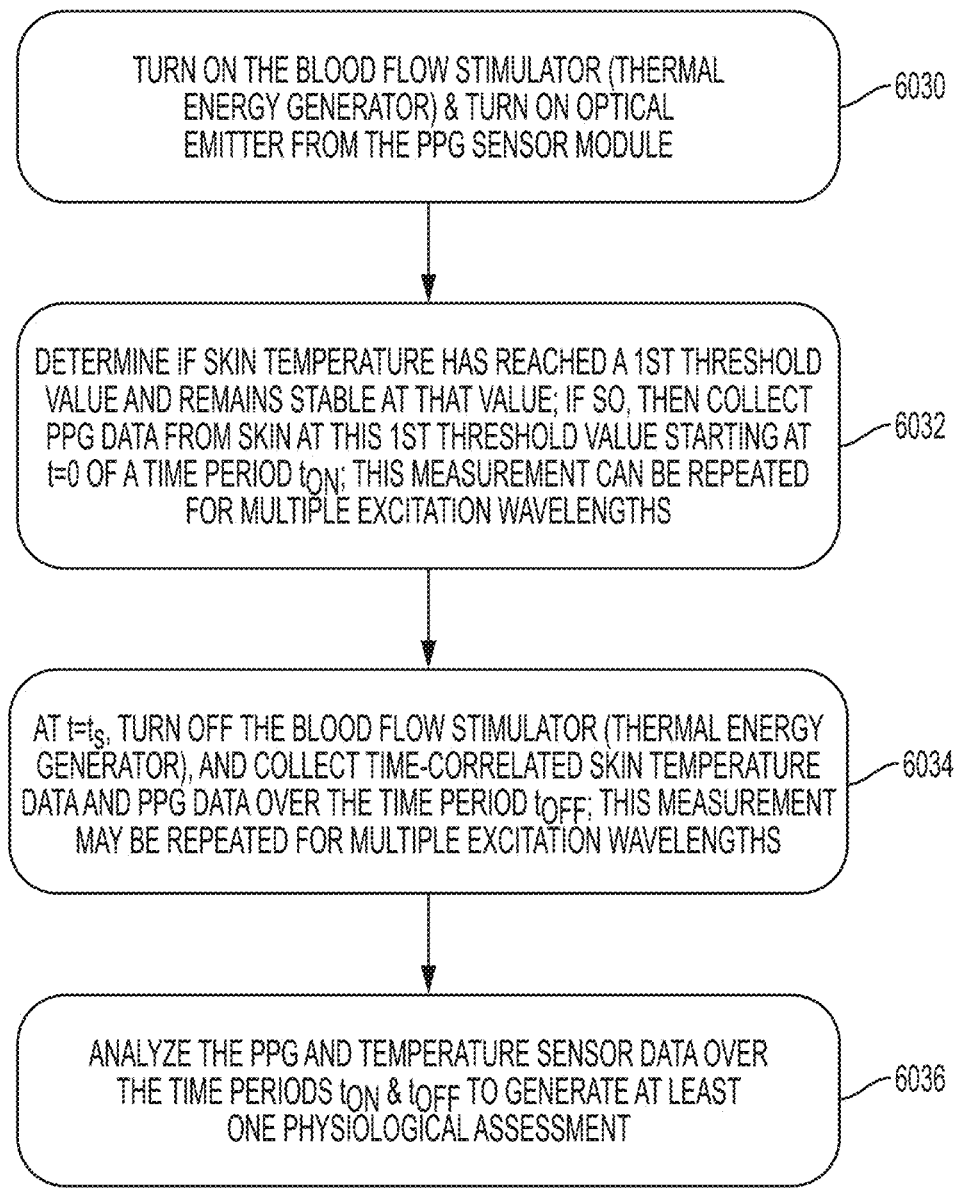
FIG. 34 is a flowchart of operations for generating physiological assessments of a subject, according to some embodiments of the present invention.

For the case where luminescent blood, skin, or tissue constituents are of interest, the method illustrated in FIG. 34 may be employed to generate a matrix of temperature-dependent optical intensities over time—optical ($Temp_n,\lambda_n,t_n$)—over an optical scattering time period $t_{scatt}$ and an optical luminescence period $t_{lum}$. For example, as illustrated in FIG. 34, a blood flow stimulator (e.g., a thermal energy generator) is turned on and an optical emitter of a PPG sensor module is turned on (Block 6030). A determination is made if skin temperature has reached a first threshold value and remains stable at that value and, if so, then PPG data is collected from skin at this first threshold value starting at t=0 of a time period $t_{on}$ (Block 6032). This measurement can be repeated for multiple excitation wavelengths. At time $t=t_s$, the blood flow stimulator (e.g., a thermal energy generator) is turned off and time-correlated skin temperature data and PPG data is collected over the time period $t_{off}$ (Block 6034). This measurement may be repeated for multiple excitation wavelengths. The PPG and temperature sensor data is analyzed over the time periods $t_{on}$ and $t_{off}$ to generate at least one physiological assessment for the subject (Block 6036).

It should be noted that although the $\lambda$ value in FIG. 34 represents the peak optical excitation wavelength—$\lambda_{excit}$—the optical luminescence collected may be at multiple luminescence wavelengths—$\lambda_{lum}$—for a given $\lambda_{excit}$ if a multi-wavelength optical detector is utilized in the PPG sensor module, as described above. An advantage of the method of FIG. 34 is that data may be collected for both PPG optical scatter and bioluminescence, and the characteristic temperature dependence of both optical properties may be collected and analyzed to generate physiological assessments.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of removing motion artifacts from a biometric signal generated by a sensor module worn by a subject, wherein the sensor module includes at least one optical emitter and at least one optical detector, the method comprising:
   directing light from the at least one optical emitter:
      at a first light guide along a first optical pathway, the first light guide configured to cause the light directed along the first optical pathway to enter into a body of the subject; and
      at a second light guide along a second optical pathway, the second light guide configured to cause the light directed along the second optical pathway to be reflected from a skin surface of subject;
   detecting light that has entered the body of the subject along the first optical pathway from the body of the subject and generating a first signal comprising subject physiological information via the at least one optical detector;
   detecting light reflected by the skin surface of the subject along the second optical pathway and generating a second signal comprising subject motion information via the at least one optical detector; and
   processing the first and second signals to remove motion artifacts from the first signal using the subject motion information.

2. The method of claim 1, wherein the at least one optical emitter comprises first and second optical emitters, and wherein the method comprises directing light from the first optical emitter into the body of the subject via the first optical pathway, and directing light from the second optical emitter at the body along the second optical pathway.

3. The method of claim 1, wherein the at least one optical detector comprises first and second optical detectors, and wherein the method comprises detecting light from the body of the subject and generating a first signal comprising subject physiological information via the first optical detector, and detecting light reflected by the skin surface and generating a second signal comprising subject motion information via the second optical detector.

4. The method of claim 1, wherein the first and second optical pathways are optically isolated from each other.

5. The method of claim 1, wherein the first optical pathway is configured such that light therefrom is directed towards the body at a first angle, wherein the second optical pathway is configured such that light therefrom is directed towards the body at a second angle different from the first angle, wherein the first angle encourages absorption of light from the first optical pathway by the body, and wherein the second angle discourages absorption of light from the second optical pathway by the body.

6. A device for sensing physiological and body motion information, the device comprising:
   at least one optical emitter configured to emit light along at least two light pathways;
   a first light guide configured to direct light along a first pathway that, wherein one pathway is configured to sense body motion information by sensing light scattered from a skin surface of the body, and wherein; and
   a second light guide configured to direct light along a second pathway that at another pathway is configured to sense physiological information by sensing light that has entered the body and scattered from the body by blood flow;
   a detector configured to:
      detect light along the first pathway that is reflected by the skin surface of the subject and generate a first signal comprising subject motion information; and
      detect light along the second pathway from the body of the subject and generating a second signal comprising subject physiological information; and
   a processor configured to process the first and second signals to determine a physiological parameter of a user.

7. The device of claim 6, wherein the device is a wearable device.

8. The device of claim 6, wherein the device is configured to be positioned at or within an ear of the subject.

9. The device of claim 6, wherein the device is configured to be secured to an appendage of the subject, integrated within a wearable device, integrated within clothing worn by the subject or a combination thereof.

* * * * *